US009243038B2

(12) United States Patent
Liu et al.

(10) Patent No.: US 9,243,038 B2
(45) Date of Patent: Jan. 26, 2016

(54) MACROCYCLIC INSULIN-DEGRADING ENZYME (IDE) INHIBITORS AND USES THEREOF

(75) Inventors: David R. Liu, Lexington, MA (US); Juan Pablo Maianti, Cambridge, MA (US); Alan Saghatelian, Somerville, MA (US); Ralph E. Kleiner, New York, NY (US)

(73) Assignee: President and Fellows of Harvard College, Cambridge, MA (US)

( * ) Notice: Subject to any disclaimer, the term of this patent is extended or adjusted under 35 U.S.C. 154(b) by 0 days.

(21) Appl. No.: 14/130,336

(22) PCT Filed: Jun. 29, 2012

(86) PCT No.: PCT/US2012/044977
§ 371 (c)(1),
(2), (4) Date: Mar. 3, 2014

(65) Prior Publication Data
US 2014/0213515 A1 Jul. 31, 2014

Related U.S. Application Data

(60) Provisional application No. 61/503,646, filed on Jul. 1, 2011.

(51) Int. Cl.
*C07K 14/00* (2006.01)
*C07K 1/00* (2006.01)
*C07K 7/54* (2006.01)
*A61K 31/395* (2006.01)
*C07K 5/02* (2006.01)
*A61K 38/00* (2006.01)

(52) U.S. Cl.
CPC ............... *C07K 7/54* (2013.01); *A61K 31/395* (2013.01); *C07K 5/0215* (2013.01); *A61K 38/00* (2013.01)

(58) Field of Classification Search
None
See application file for complete search history.

(56) References Cited

U.S. PATENT DOCUMENTS

| 2002/0068301 | A1 | 6/2002 | Lai et al. |
| 2004/0067503 | A1 | 4/2004 | Tan et al. |
| 2006/0025566 | A1 | 2/2006 | Hoveyda et al. |
| 2008/0139456 | A1 | 6/2008 | Burke et al. |
| 2008/0242598 | A1 | 10/2008 | Fairlie et al. |
| 2010/0105601 | A2 | 4/2010 | Brady et al. |
| 2013/0178429 | A1 | 7/2013 | Liu et al. |

FOREIGN PATENT DOCUMENTS

| WO | WO 2004/016767 A2 | 2/2004 |
| WO | WO 2007/016441 A1 | 2/2007 |
| WO | WO 2008/156701 A2 | 12/2008 |
| WO | WO 2012/016186 A1 | 2/2012 |
| WO | WO 2013/006451 A2 | 1/2013 |

OTHER PUBLICATIONS

Ettmayer P. et al. J. Med. Chem. (2004) 47(10), pp. 2393-2404.*
Singh, Yashveer et al, "Recent Trends in Targeted Anticancer Prodrug and Conjugate," DesignCurr Med Chem. 2008 ; 15(18): 1802-1826.*
Muller, Christa E. "Prodrug Approaches for Enhancing the Bioavailability of Drugs with Low Solubility," Chemistry & Biodiversity, vol. 6 (2009), pp. 2071-2083.*
Beaumont, et, al "Design of Ester Prodrugs to Enhance Oral Absorption of Poorly Permeable Compounds: Challenges to the Discovery Scientist," Current Drug Metabolism, 2003, 4, 461-485.*
Han, H.-K.. AAPS Pharmsci. (2000) 2(1), Article 6, pp. 1-11.*
Testa Prodrug research: futile or fertile? Biochemical Pharmacology (2004) 2097-2106.*
International Search Report and Written Opinion for Application No. PCT/US2011/045966, mailed Dec. 16, 2011.
International Preliminary Report on Patentability for Application No. PCT/US2011/045966, mailed Feb. 7, 2013.
International Search Report and Written Opinion for Application No. PCT/US2012/044977, mailed Dec. 6, 2012.
International Preliminary Report on Patentability for Application No. PCT/US2012/044977, mailed Jan. 16, 2014.
PubChem CID 46938796. Nov. 15, 2010. [Retrieved from the internet Dec. 2, 2011:http://pubchem.ncbi.nim.nih.gov/summary/summary.cgi?cid=46938796&loc=ec_rcs].
Abdul-Hay et al., Optimization of Peptide Hydroxamate Inhibitors of Insulin-Degrading Enzyme Reveals Marked Substrate-Selectivity. J Med Chem 2013;56(6):2246-2255. doi:10.1021/jm301280p. Epub Mar. 15, 2013.
Becker et al., Insulysin and pitrilysin: insulin-degrading enzymes of mammals and bacteria. Methods Enzymol. 1995;248:693-703.
Bednarek et al., Selective high affinity peptide antagonist of alpha melanotropin action at human melanocortin recept or 4: their synthesis and biological evaluation in vitro. J Med Chem. 2001;44:3665-72.
Bennett et al., Degradation of amylin by insulin-degrading enzyme. J Biol Chem. Nov. 24, 2000;275(47):36621-5.
Bennett et al., Degradation of relaxin family peptides by insulin-degrading enzyme. Ann N Y Acad Sci. Apr. 2009;1160:38-41. doi:10.1111/j.1749-6632.2008.03782.x.
Berge et al., Pharmaceutical salts. J Pharm Sci. Jan. 1977;66(1):1-19.
Brudno et al., An in vitro translation, selection and amplification system for peptide nucleic acids. Nat Chem Biol. Feb. 2010;6(2):148-55. doi: 10.1038/nchembio.280. Epub Dec. 27, 2009.

(Continued)

*Primary Examiner* — Thomas S Heard
(74) *Attorney, Agent, or Firm* — Wolf, Greenfield & Sacks, P.C.

(57) ABSTRACT

Macrocyclic compounds that specifically inhibit insulin degrading enzyme (IDE) are provided. Pharmaceutically acceptable salts, solvates, hydrates, stereoisomers, polymorphs, tautomers, isotopically enriched forms, and prodrugs of the macrocyclic IDE inhibitors are also described. Pharmaceutical compositions are also provided. In vivo and in vitro methods of using the IDE inhibitor, and pharmaceutical compositions comprising the IDE inhibitor, for example, for the inhibition of IDE in a subject exhibiting aberrant IDE activity, impaired insulin signaling, or insulin resistance, for example, a subject having diabetes, are also provided.

24 Claims, 19 Drawing Sheets

(56) References Cited

OTHER PUBLICATIONS

Carrasquillo et al., Concordant association of insulin degrading enzyme gene (IDE) variants with IDE mRNA, Abeta, and Alzheimer's disease. PLoS One. Jan. 19, 2010;5(1):e8764.

Ciaccio et al., Somatostatin: a novel substrate and a modulator of insulin-degrading enzyme activity. J Mol Biol. Feb. 2009 6;385(5):1556-67. doi:10.1016/j.jmb.2008.11.025. Epub Nov. 25, 2008.

Clark et al., Design, synthesis and selection of DNA-encoded small-molecule libraries. Nat Chem Biol. Sep. 2009;5(9):647-54. doi:10.1038/nchembio.211. Epub Aug. 2, 2009. Erratum in: Nat Chem Biol. Oct. 2009;5(10):772.

Coan et al., Stoichiometry and physical chemistry of promiscuous aggregate-based inhibitors. J Am Chem Soc. Jul. 23, 2008;130(29):9606-12. doi:10.1021/ja802977h. Epub Jun. 28, 2008.

Driggers et al., the exploration of macrocycles for drug discovery—an underexploited structural class. Nat Rev Drug Discov. Jul. 2008;7(7):608-24. doi: 10.1038/nrd2590.

Drucker., the biology of incretin hormones. Cell Metab. Mar. 2006;3(3):153-65.

Duckworth et al., Insulin degradation: progress and potential. Endocr Rev. Oct. 1998;19(5):608-24.

Duckworth et al., Insulin and glucagon degradation by the same enzyme. Diabetes. Jun. 1974;23(6):536-43.

Farris et al., Insulin-degrading enzyme regulates the levels of insulin, amyloid beta-protein, and the beta-amyloid precursor protein intracellular domain in vivo. Proc Natl Acad Sci U S A. Apr. 1, 2003;100(7):4162-7. Epub Mar. 12, 2003.

Forster et al., Programming peptidomimetic syntheses by translating genetic codes designed de novo. Proc Natl Acad Sci U S A. May 27, 2003;100(11):6353-7. Epub May 16, 2003.

Gartner et al. DNA-templated organic synthesis and selection of a library of macrocycles. Science. Sep. 10, 2004;305(5690):1601-5. Epub Aug 19, 2004.

Gartner et al., Expanding the reaction scope of DNA-templated synthesis. Angew Chem Int Ed Engl. May 17, 2002;41(10):1796-800.

Gartner et al., Multistep small-molecule synthesis programmed by DNA templates. J Am Chem Soc. Sep. 4, 2002;124(35):10304-6.

Gartner et al., The generality of DNA-templated synthesis as a basis for evolving non-natural small molecules. J Am Chem Soc. Jul. 18, 2001;123(28):6961-3.

Gedulin et al., Role of endogenous amylin in glucagon secretion and gastric emptying in rats demonstrated with the selective antagonist, AC187. Regul Pept. Dec. 10, 2006;137(3):121-7. Epub Aug. 17, 2006.

Georghiou et al., Highly specific, bisubstrate-competitive Src inhibitors from DNA-templated macrocycles. Nat Chem Biol. Feb. 19, 2012;8(4):366-74. doi: 10.1038/nchembio.792.

Gu et al., Quantitative trait loci near the insulin-degrading enzyme (IDE) gene contribute to variation in plasma insulin levels. Diabetes. Aug. 2004;53(8):2137-42.

Guo et al., Molecular basis for the recognition and cleavages of IGF-II, TGF-alpha, and amylin by human insulin-degrading enzyme. J Mol Biol. Jan. 2010 15;395(2):430-43. oi:10.1016/j.jmb.2009.10.072. Epub Nov 5, 2009.

Halpin et al., DNA display I. Sequence-encoded routing of DNA populations. PLoS Biology. Jul. 2004; 2(7):1015-21.

Halpin et al., DNA display II. Genetic manipulation of combinatorial chemistry libraries for small-molecule evolution. PLoS Biology. Jul. 2004; 2(7):1022-30.

Halpin et al., DNA display III. Solid-phase organic synthesis on unprotected DNA. PLoS Biology. Jul. 2004; 2(7):1031-8.

Hamel et al., Identification of the cleavage sites of transforming growth factor alpha by insulin-degrading enzymes. Biochim Biophys Acta. Apr. 4, 1997;1338(2):207-14.

Hollander et al., Effect of pramlintide on weight in overweight and obese insulin-treated type 2 diabetes patients. Obes Res. Apr. 2004;12(4):661-8.

Hruby et al., Synthesis of oligopeptide and peptidomimetic libraries. Curr Opin Chem Biol. Jun. 1997;1(1):114-9.

Kanan et al., Reaction discovery enabled by DNA-templated synthesis and in vitro selection. Nature. Sep. 30, 2004;431(7008):545-9.

Kim et al., Peptidomics approach to elucidate the proteolytic regulation of bioactive peptides. Proc Natl Acad Sci U S A. May 29, 2012;109(22):8523-7. Epub May 14, 2012.

Kleiner et al., DNA-templated polymerization of side-chain-functionalized peptide nucleic acid aldehydes. J Am Chem Soc. Apr. 9, 2008;130(14):4646-59. Epub Mar 15, 2008.

Kleiner et al., In vitro selection of a DNA-templated small-molecule library reveals a class of macrocyclic kinase inhibitors. J Am Chem Soc. Aug. 25, 2010;132(33):11779-91.

Kleiner et al., In vitro selection of a DNA-templated small-molecule library reveals a class of macrocyclic kinase inhibitors. J Am Chem Soc. Aug. 25, 2010;132(33):11779-91. Supporting Information. 36 pages.

Kleiner et al., Small-molecule discovery from DNA-encoded chemical libraries. Chem Soc Rev. Dec. 2011;40(12):5707-17. Epub Jun. 14, 2011.

Kolterman et al., Reduction of postprandial hyperglycemia in subjects with IDDM by intravenous infusion of AC137, a human amylin analogue. Diabetes Care. Aug. 1998;18(8):1179-82.

Kurochkin et al., Alzheimer's beta-amyloid peptide specifically interacts with and is degraded by insulin degrading enzyme. Febs Lett. May 23, 1994;345(1):33-7.

Kwon et al., Quantitative comparison of the relative cell permeability of cyclic and linear peptides. Chem Biol. Jun. 2007;14(6):671-7.

Lee et al., Metabolic manifestations of insulin deficiency do not occur without glucagon action. Proc Natl Acad Sci U S A. Sep. 11, 2012;109(37):14972-6. doi: 10.1073/pnas.1205983109. Epub Aug. 13, 2012.

Leissring et al., Designed inhibitors of insulin-degrading enzyme regulate the catabolism and activity of insulin. PLoS One. May 7, 2010;5(5):e10504. doi: 10.1371/journal.pone.0010504.

Li et al., DNA-templated organic synthesis: nature's strategy for controlling chemical reactivity applied to synthetic molecules. Angew Chem Int Ed Engl. Sep. 20, 2004;43(37):4848-70.

Liu et al., Synthesis and screening of a cyclic peptide library: Discovery of small molecule ligands against human prolactin receptor. Bioord Med Chem Lett. 2009;17:1026-33. doi:10.1016/j.bmc.2008.01.015. Epub Jan. 13, 2008.

Llovera et al., The catalytic domain of insulin-degrading enzyme forms a denaturant-resistant complex with amyloid beta peptide: implications for Alzheimer disease pathogenesis. J Biol Chem. Jun. 20, 2008;283(25):17039-48. doi: 10.1074/jbc.M706316200. Epub Apr. 14, 2008.

Malito et al., Molecular bases for the recognition of short peptide substrates and cysteine-directed modifications of human insulin-degrading enzyme. Biochemistry. Dec. 2, 2008;47(48):12822-34. doi: 10.1021/bi801192h.

Manolopoulou et al., Molecular basis of catalytic chamber-assisted unfolding and cleavage of human insulin by human insulin-degrading enzyme. J Biol Chem. May 22, 2009;284(21):14177-88. doi:10.1074/jbc.M900068200. Epub Mar. 25, 2009.

Miller et al., Amyloid-beta peptide levels in brain are inversely correlated with insulysin activity levels in vivo. Proc Natl Acad Sci U S A. May 13, 2003;100(10):6221-6. Epub May 5, 2003.

Mirsky et al, Effect of insulinase-inhibitor on hypoglycemic action of insulin. Science. Sep. 23, 1995;122(3169):559-60.

Mirsky et al., The inactivation of insulin by tissue extracts; the distribution and properties of insulin inactivating extracts. Arch Biochem. Jan. 1949;20(1):1-9.

Misbin et al., Inhibition of insulin degradation by insulin-like growth factors. Endocrinology. Oct. 1983;113(4):1525-7.

Qiu et al., Insulin-degrading enzyme regulates extracellular levels of amyloid beta-protein by degradation. J Biol Chem. Dec. 4, 1998;273(49):32730-8.

Riddle et al., Emerging therapies mimicking the effects of amylin and glucagon-like peptide 1. Diabetes Care. Feb. 2006;29(2):435-49.

Rosenbaum et al., Efficient and sequence-specific DNA-templated polymerization of peptide nucleic acid aldehydes. J Am Chem Soc. Nov. 19, 2003;125(46):13924-5.

(56) References Cited

OTHER PUBLICATIONS

Rozenman et al., Development and initial application of a hybridization-independent, DNA-encoded reaction discovery system compatible with organic solvents. J Am Chem Soc. Dec. 5, 2007;129(48):14933-8. Epub Nov. 10, 2007.

Safavi et al., Identification of gamma-endorphin-generating enzyme as insulin-degrading enzyme. Biochemistry. Nov. 12, 1996;35(45):14318-25.

Scheuermann et al., DNA-encoded chemical libraries for the discovery of MMP-3 inhibitors. Bioconjug Chem. Mar. 2008;19(3):778-85. Epub Feb. 7, 2008.

Shen et al., Structures of human insulin-degrading enzyme reveal a new substrate recognition mechanism. Nature. Oct. 19, 2006;443(7113):870-4. Epub Oct. 11, 2006.

Snyder et al., Ordered multistep synthesis in a single solution directed by DNA templates. Angew Chem Int Ed Engl. Dec. 1, 2005;44(45):7379-82.

Trebbien et al., Neutral endopeptidase 24.11 is important for the degradation of both endogenous and exogenous glucagon in anesthetized pigs. Am J Physiol Endocrinol Metab. Sep. 2004;287(3):E431-8. Epub May 4, 2004.

Tse et al., Translation of DNA into a library of 13,000 synthetic small-molecule macrocycles suitable for in vitro selection. J Am Chem Soc. Nov. 19, 2008;130(46):15611-26. doi: 10.1021/ja805649f. Epub Oct. 29, 2008.

Tse et al., Translation of DNA into a library of 13,000 synthetic small-molecule macrocycles suitable for in vitro selection. J Am Chem Soc. Nov. 19, 2008;130(46):15611-26. Epub Oct. 29, 2008, supporting information.

Unger et al., Glucagonocentric restructuring of diabetes: a pathophysiologic and therapeutic makeover. J Clin Invest. Jan. 3, 2012;122(1):4-12. doi: 10.1172/JCI60016. Epub Jan. 3, 2012.

Zhang et al., In vitro degradation of insulin-like peptide 3 by insulin-degrading enzyme. Protein J. Feb. 2010;29(2):93-8. doi:10.1007/s10930-009-9226-8.

Extended European Search Report for European Application No. EP 12807710.4, mailed Jan. 5, 2015.

* cited by examiner

| compound | C4-diamide Linker | IC$_{50}$ (µM) |
|---|---|---|
| 6a | *cis*-olefin (maleamide) | >10 |
| 6b | *trans*-olefin (fumaramide) | 0.06 |
| 6c | reduced (succinamide) | 0.57 |

| compound | "A" building block | IC$_{50}$ (µM) |
|---|---|---|
| 7 | D-phenylalanine | >10 |
| 8 | D-4-benzyl-Phe | 0.06 |

| compound | "B" building block | IC$_{50}$ (μM) |
|---|---|---|
| 9 | phenylalanine | 6.0 |
| 10 | norisoleucine | 1.5 |
| 11 | leucine | 2.1 |
| 12 | alanine | >10 |

| compound | "C" building block | IC$_{50}$ (μM) |
|---|---|---|
| 13 | alanine | 0.06 |
| 14 | D-alanine | >20 |
| 15 | serine | 0.06 |
| 16 | 2-methylalanine | 0.37 |
| 17 | glycine | 0.50 |
| 18 | (none / skipped) | >20 |
| 19 | phenylalanine | 3.2 |
| 20 | lysine | 0.065 |
| 21 | glutamate | 0.085 |
| 22 | phenylalanine | 3.2 |
| 23 | (none / skipped) | >20 |

| compound | "D" scaffold block | IC$_{50}$ (µM) |
|---|---|---|
| 24 | D-lysine amide | 7.0 |
| 25 | ornithine amide | 5.0 |
| 26 | D-lysine acid | 0.054 |
| 27 | lysine, αN-ethyl amide | 0.06 |
| 28 | lysine, αN-TEG-biotin | 0.08 |
| 29 | lysine, αN-TEG-fluorescein | 0.10 |

MACROCYCLIC INSULIN-DEGRADING ENZYME (IDE) INHIBITORS AND USES THEREOF

RELATED APPLICATION

The present invention is a national stage filing under 35 U.S.C. §371 of international PCT application, PCT/US2012/044977, filed Jun. 29, 2012, entitled "Macrocyclic Insulin-Degrading Enzyme (IDE) Inhibitors and Uses Thereof," which claims priority under 35 U.S.C. §119(e) to U.S. provisional patent application, U.S. Ser. No. 61/503,646, filed Jul. 1, 2011, entitled "Macrocyclic Insulin-Degrading Enzyme (IDE) Inhibitors," the entire contents of each of which are incorporated herein by reference.

GOVERNMENT SUPPORT

This invention was made with U.S. Government support under grant R01 GM065865 awarded by the National Institutes of Health. The U.S. Government has certain rights in this invention.

BACKGROUND OF THE INVENTION

Insulin Degrading Enzyme (IDE), also referred to as insulysin or insulin protease, is a 110 kDa zinc-binding protease of the M16A metalloprotease subfamily. IDE was first identified by its ability to degrade the β chain of insulin and has since been shown to target additional substrates, including the pathophysiologically important peptide β-amyloid, the signaling peptides glucagon, TGF-alpha, β-endorphin, and atrial natriuric peptide. While IDE is the main protease responsible for insulin degradation, most other IDE substrates are known to be targeted and degraded by other proteases as well.

Despite great interest in pharmacological targeting of IDE, the enzyme has remained an elusive target. The only known series of IDE-targeted inhibitors to date are peptide hydroxamic acids, e.g., Ii1 (Inhibitor of IDE1, see Formula (Ii1) below, and, e.g., Leissring et al. (2010), Designed Inhibitors of Insulin-Degrading Enzyme Regulate the Catabolism and Activity of Insulin. *PLoS ONE* 5(5): e10504).

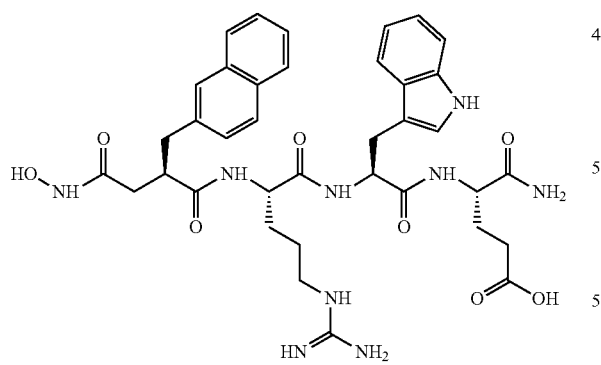

Ii1

One important application for IDE inhibitors is the treatment of diabetes. The term diabetes refers to a group of endocrinological disorders that are characterized by impaired insulin signaling or insulin resistance. Conventional therapeutic approaches for diabetic patients aim to enhance insulin signaling, for example, by administration of exogenous insulin, by stimulating the generation and secretion of endogenous insulin, or by activating downstream targets of the insulin receptor (IR) signaling cascade. IDE inhibitors open another therapeutic avenue to improve insulin signaling by inhibiting IDE-mediated insulin catabolism.

Even though IDE and its involvement in insulin catabolism has been known for several decades, the development of small-molecule inhibitors of IDE has been surprisingly difficult. As a result, there is need for the development of clinically useful IDE inhibitors.

SUMMARY OF THE INVENTION

Macrocycle libraries suitable for in vitro selection can be generated based on DNA-templated synthetic methods. The preparation and characterization of a 13,824-membered DNA-templated macrocycle library and the in vitro selection of kinase inhibitory macrocycles from that library are described in international PCT application, PCT/US2011/045966, entitled "Macrocyclic Kinase Inhibitors and Uses Thereof," filed Jul. 29, 2011, published as WO/2012/016186, and in Kleiner et al., "In Vitro Selection of a DNA-Templated Macrocycle Library Reveals a Class of Macrocyclic Kinase Inhibitors." *J. Am. Chem. Soc.* 132, 11779-11791 (2010), the entire contents of each of which are incorporated herein by reference.

Macrocycles are particularly attractive candidates for the discovery of biologically active small molecules because their rigid scaffolds can decrease the entropic cost of target binding and limit access to non-binding conformations, resulting in higher affinity and greater binding specificity than their corresponding linear counterparts. In addition, macrocyclic peptide-like structures can offer advantages in vitro and in vivo over their linear analogs since they can possess higher bioavailability, membrane permeability, and for resistance to degradation in vivo.

This disclosure describes the discovery and characterization of macrocyclic molecules, also referred to herein as macrocycles, compounds, macrocyclic compounds, or macrocyclic inhibitors, that potently and specifically inhibit IDE. In vitro assays revealed that the macrocycles provided herein inhibit IDE with $IC_{50}$ values as low as 50 nM, and that IDE inhibition is specific, as related enzymes, e.g., related zinc-metalloproteases neurolysin (NLN), thimet oligopeptidase (THOP 1), and neprilysin (NEP) are not significantly inhibited by the macrocycles provided herein.

The present disclosure provides macrocyclic IDE inhibitors. In some embodiments, the present disclosure provides macrocyclic IDE inhibitors of Formula (S):

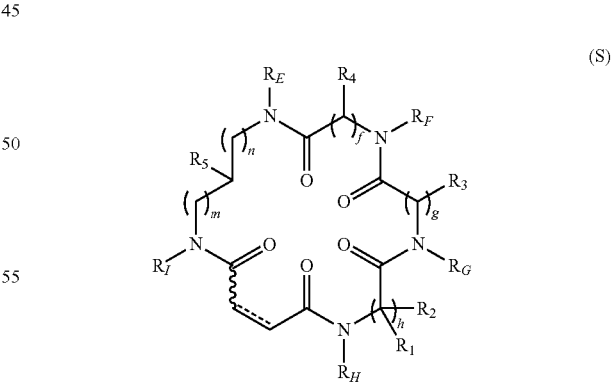

(S)

and pharmaceutically acceptable salts, solvates, hydrates, stereoisomers, polymorphs, tautomers, isotopically enriched forms, and prodrugs thereof; wherein:

n is 0 or an integer between 1-4, inclusive;
m is 0 an integer between 1-4, inclusive;
f is an integer between 1-3, inclusive;
g is an integer between 1-3, inclusive;

h is an integer between 1-3, inclusive;

------ is a single or double C—C bond, wherein when ------ is a double C—C bond, then ⁓ indicates that the adjacent C—C double bond is in the cis or trans configuration;

each instance of $R_1$ is independently hydrogen; halogen; substituted or unsubstituted aliphatic; substituted or unsubstituted heteroaliphatic; substituted or unsubstituted aryl; substituted or unsubstituted heteroaryl; acyl; —$OR_A$; —$N(R_A)_2$; —$SR_A$; =O; —CN; —$NO_2$; —SCN; —$SOR_A$; or —$SO_2R_A$; wherein each occurrence of $R_A$ is independently hydrogen; a protecting group; substituted or unsubstituted aliphatic; substituted or unsubstituted heteroaliphatic; acyl; substituted or unsubstituted aryl; or substituted or unsubstituted heteroaryl;

each instance of $R_2$ is independently hydrogen; halogen; substituted or unsubstituted aliphatic; substituted or unsubstituted heteroaliphatic; substituted or unsubstituted aryl; substituted or unsubstituted heteroaryl; acyl; —$OR_B$; —$N(R_B)_2$; —$SR_B$; =O; —CN; —$NO_2$; —SCN; —$SOR_B$; or —$SO_2R_B$; wherein each occurrence of $R_B$ independently hydrogen; a protecting group; substituted or unsubstituted aliphatic; substituted or unsubstituted heteroaliphatic; acyl; substituted or unsubstituted aryl; or substituted or unsubstituted heteroaryl;

each instance of $R_3$ is independently hydrogen; halogen; substituted or unsubstituted aliphatic; substituted or unsubstituted heteroaliphatic; substituted or unsubstituted aryl; substituted or unsubstituted heteroaryl; acyl; —$OR_C$; —$N(R_C)_2$; —$SR_C$; =O; —CN; —$NO_2$; —SCN; —$SOR_C$; or —$SO_2R_C$; wherein each occurrence of $R_C$ is independently hydrogen; a protecting group; substituted or unsubstituted aliphatic; substituted or unsubstituted heteroaliphatic; acyl; substituted or unsubstituted aryl; or substituted or unsubstituted heteroaryl;

each instance of $R_4$ is independently hydrogen; halogen; substituted or unsubstituted aliphatic; substituted or unsubstituted heteroaliphatic; substituted or unsubstituted aryl; substituted or unsubstituted heteroaryl; acyl; —$OR_D$; —$N(R_D)_2$; —$SR_C$; =O; —CN; —$NO_2$; —SCN; —$SOR_D$; or —$SO_2R_D$; wherein each occurrence of $R_D$ is independently hydrogen; a protecting group; substituted or unsubstituted aliphatic; substituted or unsubstituted heteroaliphatic; acyl; substituted or unsubstituted aryl; or substituted or unsubstituted heteroaryl;

$R_5$ is substituted or unsubstituted aliphatic; substituted or unsubstituted heteroaliphatic; substituted or unsubstituted aryl; substituted or unsubstituted heteroaryl; substituted or unsubstituted amino; C(=O)N($R_J$)_2; CO(=O)$R_J$; or —C(=O)$SR_J$, or $CH_2C$(=O)N($R_J$)_2, wherein each occurrence of $R_J$ is independently hydrogen; a protecting group; substituted or unsubstituted aliphatic; substituted or unsubstituted heteroaliphatic; substituted or unsubstituted acyl; substituted or unsubstituted aryl; or substituted or unsubstituted heteroaryl; or two $R_D$ groups are joined to form a substituted or unsubstituted heterocyclic group; optionally wherein $R^4$ further comprises a label, resin, or therapeutic agent attached thereto; and each instance of $R_E$, $R_F$, $R_G$, $R_H$, and $R_I$ is independently hydrogen; acyl; a nitrogen protecting group; substituted or unsubstituted aliphatic; substituted or unsubstituted heteroaliphatic; substituted or unsubstituted aryl; substituted or unsubstituted heteroaryl; substitute or unsubstituted hydroxyl; substituted or unsubstituted thiol; substituted or unsubstituted amino; or halogen; optionally wherein an $R_4$ group and $R_E$ are joined to form a substituted or unsubstituted heterocyclic ring; an $R_3$ group and $R_G$ are joined to form a substituted or unsubstituted heterocyclic ring; and/or an $R_1$ or $R_2$ group and $R_H$ are joined to form a substituted or unsubstituted heterocyclic ring.

In one aspect, the present invention provides macrocyclic IDE inhibitors. The IDE inhibitors described herein are typically of the Formula (I):

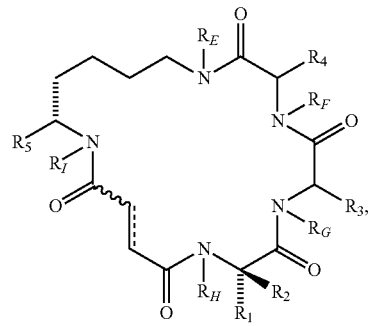

(I)

or pharmaceutically acceptable salts, solvates, hydrates, stereoisomers, polymorphs, tautomers, isotopically enriched forms, and prodrugs thereof, wherein:

------ is a single or double C—C bond, wherein when ------ is a double C—C bond, then ⁓ indicates that the adjacent C—C double bond is in the cis or trans configuration;

$R_1$ is hydrogen; halogen; substituted or unsubstituted aliphatic; substituted or unsubstituted heteroaliphatic; substituted or unsubstituted aryl; substituted or unsubstituted heteroaryl; substituted or unsubstituted acyl; —$OR_A$; —$N(R_A)_2$; —$SR_A$; =O; —CN; —$NO_2$; —SCN; —$SOR_A$; or —$SO_2R_A$; wherein each occurrence of $R_A$ is independently hydrogen; a protecting group; substituted or unsubstituted aliphatic; substituted or unsubstituted heteroaliphatic; substituted or unsubstituted acyl; substituted or unsubstituted aryl; or substituted or unsubstituted heteroaryl;

$R_2$ is hydrogen; halogen; substituted or unsubstituted aliphatic; substituted or unsubstituted heteroaliphatic; substituted or unsubstituted aryl; substituted or unsubstituted heteroaryl; substituted or unsubstituted acyl; —$OR_B$; —$N(R_B)_2$; —$SR_B$; =O; —CN; —$NO_2$; —SCN; —$SOR_B$; or —$SO_2R_B$; wherein each occurrence of $R_B$ independently hydrogen; a protecting group; substituted or unsubstituted aliphatic; substituted or unsubstituted heteroaliphatic; substituted or unsubstituted acyl; substituted or unsubstituted aryl; or substituted or unsubstituted heteroaryl;

$R_3$ is hydrogen; halogen; substituted or unsubstituted aliphatic; substituted or unsubstituted heteroaliphatic; substituted or unsubstituted aryl; substituted or unsubstituted heteroaryl; substituted or unsubstituted acyl; —$OR_C$; —$N(R_C)_y$; —$SR_C$; =O; —CN; —$NO_2$; —SCN; —$SOR_C$; or —$SO_2R_C$; wherein y is 0, or an integer between 1-2, inclusive, and wherein each occurrence of $R_C$ is independently hydrogen; a protecting group; substituted or unsubstituted aliphatic; substituted or unsubstituted heteroaliphatic; substituted or unsubstituted acyl; substituted or unsubstituted aryl; or substituted or unsubstituted heteroaryl;

$R_4$ is hydrogen; halogen; substituted or unsubstituted aliphatic; substituted or unsubstituted heteroaliphatic; substituted or unsubstituted aryl; substituted or unsubstituted heteroaryl; substituted or unsubstituted acyl; —$OR_C$; —$N(R_D)_y$; —$SR_C$; =O; —CN; —$NO_2$; —SCN; —$SOR_D$; or —$SO_2R_D$; wherein y is 0, or an integer between 1-2, inclusive, and wherein each occurrence of $R_D$ is independently hydrogen; a protecting group; substituted or unsubstituted aliphatic; substituted or unsubstituted heteroaliphatic; substituted or unsubstituted acyl; substituted or unsubstituted aryl; or substituted or unsubstituted heteroaryl $R_5$ is substituted or unsubstituted aliphatic; substituted or unsubstituted heteroaliphatic; substituted or unsubstituted aryl; substituted or unsubstituted heteroaryl; substituted or unsubstituted amino; $C(=O)N(R_J)_2$; $-CO(=O)R_J$; or $-C(=O)SR_J$, or $CH_2C(=O)N(R_J)_2$, wherein each occurrence of $R_J$ is independently hydrogen; a protecting group; substituted or unsubstituted aliphatic; substituted or unsubstituted heteroaliphatic; substituted or unsubstituted acyl; substituted or unsubstituted aryl; or substituted or unsubstituted heteroaryl; or two $R_D$ groups are joined to form a substituted or unsubstituted heterocyclic group; optionally wherein $R^4$ further comprises a label, resin, or therapeutic agent attached thereto; and each instance of $R_E$, $R_F$, $R_G$, $R_H$, and $R_J$ is independently hydrogen; substituted or unsubstituted acyl; a nitrogen protecting group; substituted or unsubstituted aliphatic; substituted or unsubstituted heteroaliphatic; substituted or unsubstituted aryl; substituted or unsubstituted heteroaryl; substitute or unsubstituted hydroxyl; substituted or unsubstituted thiol; substituted or unsubstituted amino; or halogen; optionally wherein an $R_4$ group and $R_F$ are joined to form a substituted or unsubstituted heterocyclic ring; an $R_3$ group and $R_G$ are joined to form a substituted or unsubstituted heterocyclic ring; and/or an $R_1$ or $R_2$ group and $R_H$ are joined to form a substituted or unsubstituted heterocyclic ring. In some embodiments, $R_E$, $R_F$, $R_G$, $R_H$, and $R_J$ are all H.

In some embodiments, the macrocyclic IDE inhibitors are of Formula (II):

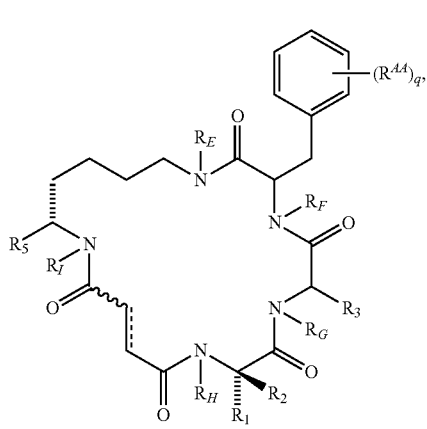

(II)

or pharmaceutically acceptable salts, solvates, hydrates, stereoisomers, polymorphs, tautomers, isotopically enriched forms, and prodrugs thereof,
wherein:
  q is 0 or an integer between 1 and 5, inclusive;
  ------ is a single or double C—C bond, wherein when
  ------ is a double C—C bond, then ∿∿ indicates that the adjacent C—C double bond is in a cis or trans configuration; and
  each instance of $R_1$, $R_2$, $R_3$, $R_5$, $R_E$, $R_F$, $R_G$, $R_H$, and $R_J$ is independently as defined in Formula (I);
  each instance of $R^{AA}$ is independently halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, $-OR^{43}$, $-N(R^{44})_2$, $-SR^{43}$, $-C(=O)R^{43}$, $-CO(=O)R^{43}$, $-C(=O)SR^{43}$, $-C(=O)N(R^{44})_2$, $-OC(=O)R^{43}$, $-OCO(=O)R^{43}$, $-OC(=O)SR^{43}$, $-OC(=O)N(R^{44})_2$, $-NR^{44}C(=O)R^{44}$, $-NR^{44}CO(=O)R^{43}$, $-NR^{44}C(=O)SR^{43}$, $-NR^{44}C(=O)N(R^{44})_2$, $-SC(=O)R^{43}$, $-SC(=O)OR^{43}$, $-SC(=O)SR^{43}$, $-SC(=O)N(R^{44})_2$, $-C(=NR^{44})R^{43}$, $-C(=NR^{44})OR^{43}$, $-C(=NR^{44})SR^{43}$, $-C(=NR^{44})N(R^{44})_2$, $-OC(=NR^{44})R^{43}$, $-OC(=NR^{44})OR^{43}$, $-OC(=NR^{44})SR^{43}$, $-OC(=NR^{44})N(R^{44})_2$, $-NR^{44}C(=NR^{44})R^{42}$, $-NR^{44}C(=NR^{44})OR^{43}$, $-NR^{44}C(=NR^{44})SR^{43}$, $-NR^{44}C(=NR^{44})N(R^{44})_2$, $-SC(=NR^{43})R^{43}$, $-SC(=NR^{44})OR^{43}$, $-SC(=NR^{44})SR^{43}$, $-SC(=NR^{44})N(R^{44})_2$, $-C(=S)R^{43}$, $-C(=S)OR^{43}$, $-C(=S)SR^{43}$, $-C(=S)N(R^{44})_2$, $-OC(=S)R^{43}$, $-OC(=S)OR^{43}$, $-OC(=S)SR^{43}$, $-OC(=S)N(R^{44})_2$, $-NR^{44}C(=S)R^{44}$, $-NR^{44}C(=S)OR^{43}$, $-NR^{44}C(=S)SR^{43}$, $-NR^{44}C(=S)N(R^{44})_2$, $-SC(=S)R^{43}$, $-SC(=S)OR^{43}$, $-SC(=S)SR^{43}$, $-SC(=S)N(R^{44})_2$, $-S(=O)R^{43}$, $-SO_2R^{43}$, $-NR^{44}SO_2R^{43}$, $-SO_2N(R^{44})_2$, $-N_3$, $-CN$, $-SCN$, and $-NO_2$, wherein each occurrence of $R^{43}$ is independently hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl; and each occurrence of $R^{44}$ is independently hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, or a nitrogen protecting group, or two $R^{44}$ groups are joined to form a substituted or unsubstituted heterocyclic ring.

In some embodiments, the macrocyclic IDE inhibitors are of Formula (III):

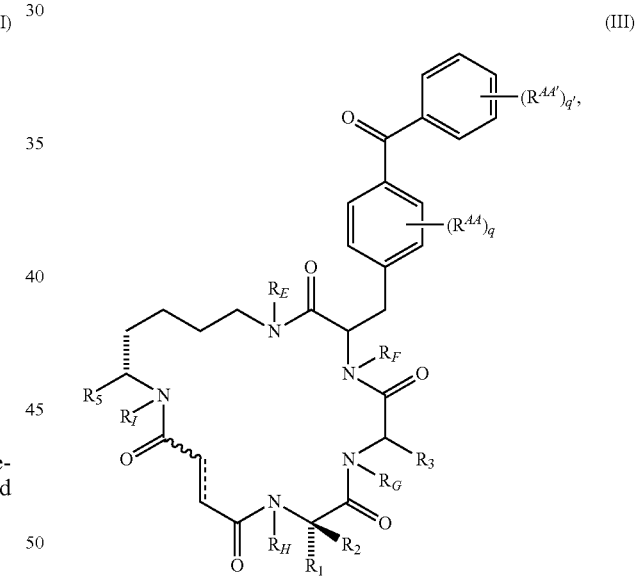

(III)

or pharmaceutically acceptable salts, solvates, hydrates, stereoisomers, polymorphs, tautomers, isotopically enriched forms, and prodrugs thereof,
wherein:
  q is 0 or an integer between 1 and 5, inclusive;
  q' is 0 or an integer between 1 and 5, inclusive;
  ------ is a single or double C—C bond, wherein when
  ------ is a double C—C bond, then ∿∿ indicates that the adjacent C—C double bond is in the cis or trans configuration;
  each instance of $R_1$, $R_2$, $R_3$, $R_5$, $R_E$, $R_F$, $R_G$, $R_H$, and $R_J$ is independently as defined in Formula (I);
  each instance of $R^{AA}$ is independently halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —OR$^{A3}$, —N(R$^{A4}$)$_2$, —SR$^{A3}$, —C(=O)R$^{A3}$, —CO(=O)R$^{A3}$, —C(=O)SR$^{A3}$, —C(=O)N(R$^{A4}$)$_2$, —OC(=O)R$^{A3}$, —OCO(=O)R$^{A3}$, —OC(=O)SR$^{A3}$, —OC(=O)N(R$^{A4}$)$_2$, —NR$^{A4}$C(=O)R$^{A4}$, —NR$^{A4}$CO(=O)R$^{A3}$, —NR$^{A4}$C(=O)SR$^{A3}$, —NR$^{A4}$C(=O)N(R$^{A4}$)$_2$, —SC(=O)R$^{A3}$, —SC(=O)R$^{A3}$, —SC(=O)SR$^{A3}$, —SC(=O)N(R$^{A4}$)$_2$, —C(=NR$^{A4}$)R$^{A3}$, —C(=NR$^{A4}$)OR$^{A3}$, —C(=NR$^{A4}$)SR$^{A3}$, —C(=NR$^{A4}$)N(R$^{A4}$)$_2$, —OC(=NR$^{A4}$)R$^{A3}$, —OC(=NR$^{A4}$)OR$^{A3}$, —OC(=NR$^{A4}$)SR$^{A3}$, —OC(=NR$^{A4}$)N(R$^{A4}$)$_2$, —NR$^{A4}$C(=NR$^{A4}$)R$^{A2}$, —NR$^{A4}$C(=NR$^{A4}$)OR$^{A3}$, —NR$^{A4}$C(=NR$^{A4}$)SR$^{A3}$, —NR$^{A4}$C(=NR$^{A4}$)N(R$^{A4}$)$_2$, —SC(=NR$^{A4}$)R$^{A3}$, —SC(=NR$^{A4}$)OR$^{A3}$, —SC(=NR$^{A4}$)SR$^{A3}$, —SC(=NR$^{A4}$)N(R$^{A4}$)$_2$, —C(=S)R$^{A3}$, —C(=S)OR$^{A3}$, —C(=S)SR$^{A3}$, —C(=S)N(R$^{A4}$)$_2$, —OC(=S)R$^{A3}$, —OC(=S)OR$^{A3}$, —OC(=S)SR$^{A3}$, —OC(=S)N(R$^{A4}$)$_2$, —NR$^{A4}$C(=S)R$^{A4}$, —NR$^{A4}$C(=S)OR$^{A3}$, —NR$^{A4}$C(=S)SR$^{A3}$, —NR$^{A4}$C(=S)N(R$^{A4}$)$_2$, —SC(=S)R$^{A3}$, —SC(=S)OR$^{A3}$, —SC(=S)SR$^{A3}$, —SC(=S)N(R$^{A4}$)$_2$, —S(=O)R$^{A3}$, —SO$_2$R$^{A3}$, —NR$^{A4}$SO$_2$R$^{A3}$, —SO$_2$N(R$^{A4}$)$_2$, —N$_3$, —CN, —SCN, and —NO$_2$, wherein each occurrence of R$^{A3}$ is independently hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl; and each occurrence of R$^{A4}$ is independently hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, or a nitrogen protecting group, or two R$^{A4}$ groups are joined to form a substituted or unsubstituted heterocyclic ring;

each instance of R$^{A4'}$ is independently halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —OR$^{A'}$, —N(R$^{A4'}$)$_2$, —SR$^{A3'}$, —C(=O)R$^{A3'}$, —CO(=O)R$^{A3'}$, —C(=O)SR$^{A3'}$, —C(=O)N(R$^{A4'}$)$_2$, —OC(=O)R$^{A3'}$, —OCO(=O)R$^{A3'}$, —OC(=O)SR$^{A3'}$, —OC(=O)N(R$^{A4'}$)$_2$, —NR$^{A4'}$C(=O)R$^{A4'}$, —NR$^{A4'}$CO(=O)R$^{A3'}$, —NR$^{A4'}$C(=O)SR$^{A3'}$, —NR$^{A4'}$C(=O)N(R$^{A4'}$)$_2$, —SC(=O)R$^{A3'}$, —SC(=O)OR$^{A3'}$, —SC(=O)SR$^{A3'}$, —SC(=O)N(R$^{A4'}$)$_2$, —C(=NR$^{A4'}$)R$^{A3'}$, —C(=NR$^{A4'}$)OR$^{A3'}$, —C(=NR$^{A4'}$)SR$^{A3'}$, —C(=NR$^{A4'}$)N(R$^{A4'}$)$_2$, —OC(=NR$^{A4'}$)R$^{A3'}$, —OC(=NR$^{A4'}$)OR$^{A3'}$, —OC(=NR$^{A4'}$)SR$^{A3'}$, —OC(=NR$^{A4'}$)N(R$^{A4'}$)$_2$, —NR$^{A4'}$C(=NR$^{A4'}$)R$^{A3'}$, —NR$^{A4'}$C(=NR$^{A4'}$)OR$^{A3'}$, —NR$^{A4'}$C(=NR$^{A4'}$)SR$^{A3'}$, —NR$^{A4'}$C(=NR$^{A4'}$)N(R$^{A4'}$)$_2$, —SC(=NR$^{A4'}$)R$^{A3'}$, —SC(=NR$^{A4'}$)OR$^{A3'}$, —SC(=NR$^{A4'}$)SR$^{A3'}$, —SC(=NR$^{A4'}$)N(R$^{A4'}$)$_2$, —C(=S)R$^{A3'}$, —C(=S)OR$^{A3'}$, —C(=S)SR$^{A3'}$, —C(=S)N(R$^{A4'}$)$_2$, —OC(=S)R$^{A3'}$, —OC(=S)OR$^{A3'}$, —OC(=S)SR$^{A3'}$, —OC(=S)N(R$^{A4'}$)$_2$, —NR$^{A4'}$C(=S)R$^{A4'}$, —NR$^{A4'}$C(=S)OR$^{A3'}$, —NR$^{A4'}$(=S)SR$^{A3'}$, —NR$^{A4'}$C(=S)N(R$^{A4'}$)$_2$, —SC(=S)R$^{A3'}$, —SC(=S)OR$^{A3'}$, —SC(=S)SR$^{A3'}$, —SC(=S)N(R$^{A4'}$)$_2$, —S(=O)R$^{A3'}$, —SO$_2$R$^{A3'}$, —NR$^{A4'}$SO$_2$R$^{A3'}$, —SO$_2$N(R$^{A4'}$)$_2$, —N$_3$, —CN, —SCN, and —NO$_2$, wherein each occurrence of R$^{A3'}$ is independently hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl; and each occurrence of R$^{A4'}$ is independently hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, or a nitrogen protecting group, or two R$^{A4'}$ groups are joined to form a substituted or unsubstituted heterocyclic ring.

In some embodiments, the macrocyclic IDE inhibitors provided herein are of Formula (IV):

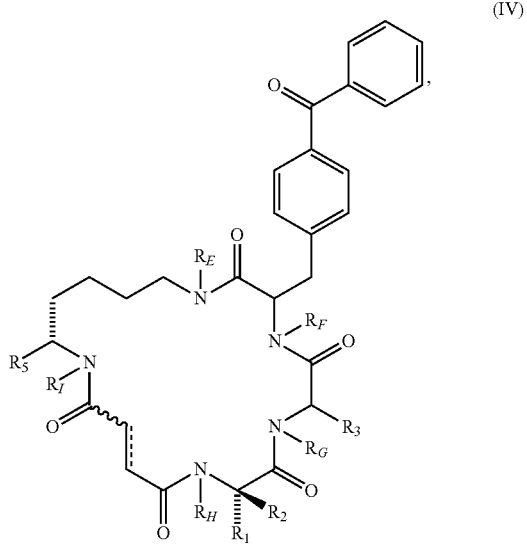

(IV)

or pharmaceutically acceptable salts, solvates, hydrates, stereoisomers, polymorphs, tautomers, isotopically enriched forms, and prodrugs thereof, wherein each instance of R$_1$, R$_2$, R$_3$, R$_5$, R$_E$, R$_F$, R$_G$, R$_H$, and R$_I$ is independently as defined in Formula (I). In certain embodiments of Formula (IV), R$_1$ represents —H, —CH$_3$, —CH$_2$—CH$_2$—C(=O)—NH$_2$, —CH$_2$—CH$_2$—CH$_2$—NH—C(=NH)—NH$_2$, —(CH$_2$)$_p$-cyclohexyl, —(CH$_2$)$_p$-cyclopentyl, —(CH$_2$)$_p$-cyclobutyl, —(CH$_2$)$_p$-cyclopropyl, —(CH$_2$)$_p$-phenyl, halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —OR$^K$, —N(R$^L$)$_2$, —SR$^K$, —C(=O)R$^K$, —C(=O)OR$^K$, —C(=O)SR$^K$, —C(=O)N(R$^L$)$_2$, —OC(=O)R$^K$, —OC(=O)OR$^K$, —OC(=O)SR$^K$, —OC(=O)N(R$^L$)$_2$, —NR$^L$C(=O)R$^L$, —NR$^L$C(=O)OR$^K$, —NR$^L$C(=O)SR$^K$, —NR$^L$C(=O)N(R$^L$)$_2$, —SC(=O)R$^K$, —SC(=O)OR$^K$, —SC(=O)SR$^K$, —SC(=O)N(R$^L$)$_2$, —C(=NR$^L$)R$^K$, —C(=NR$^L$)OR$^K$, —C(=NR$^L$)SR$^K$, —C(=NR$^L$)N(R$^L$)$_2$, —OC(=NR$^L$)R$^K$, —OC(=NR$^L$)OR$^K$, —OC(=NR$^L$)SR$^K$, —OC(=NR$^L$)N(R$^L$)$_2$, —NR$^L$C(=NR$^L$)R$^{A3}$, —NR$^L$C(=NR$^L$)OR$^K$, —NR$^L$C(=NR$^L$)SR$^K$, —NR$^L$C(=NR$^L$)N(R$^L$)$_2$, —SC(=NR$^L$)R$^K$, —SC(=NR$^L$)OR$^K$, —SC(=NR$^L$)SR$^K$, —SC(=NR$^L$)N(R$^L$)$_2$, —C(=S)R$^K$, —C(=S)OR$^K$, —C(=S)SR$^K$, —C(=S)N(R$^L$)$_2$, —OC(=S)R$^K$, —OC(=S)OR$^K$, —OC(=S)SR$^K$, —OC(=S)N(R$^L$)$_2$, —NR$^L$C(=S)R$^L$, —NR$^L$C(=S)OR$^K$, —NR$^L$C(=S)SR$^K$, —NR$^L$C(=S)N(R$^L$)$_2$, —SC(=S)R$^K$, —SC(=S)OR$^K$, —SC(=S)SR$^K$, —SC(=S)N(R$^L$)$_2$, —S(=O)R$^K$, —SO$_2$R$^K$, —NR$^L$SO$_2$R$^K$, —SO$_2$N(R$^L$)$_2$, —N$_3$, —CN, —SCN, and —NO$_2$, wherein each occurrence of R$^K$ is independently hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl; and each occurrence of $R^L$ is independently hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl; in linear or cyclic form; or a nitrogen protecting group; and each occurrence of p is independently 0 or an integer between 1 and 10 inclusive;

$R_2$ represents —H or $(CH_2)_q$—$CH_3$, wherein q is 0 or an integer between 1 and 10 inclusive;

$R_3$ represents $(CH_2)_r$-cyclohexyl, —$(CH_2)_r$-cyclopentyl, —$(CH_2)_r$-cyclobutyl, —$(CH_2)_r$-cyclopropyl, —$(CH_2)_r$-phenyl, or $(CH_2)_r$—$R_z$, wherein r is independently 0 or an integer between 1 and 10 inclusive, and wherein $R_z$ is hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl; either in linear or cyclic form;

$R_5$ represents C(=O)$NH_2$, or $CH_2$—C(=O)$NH_2$; and

----- is a double C—C bond, in either the cis or trans configuration.

In some embodiments, the IDE inhibitory compounds provided herein are of formula (V):

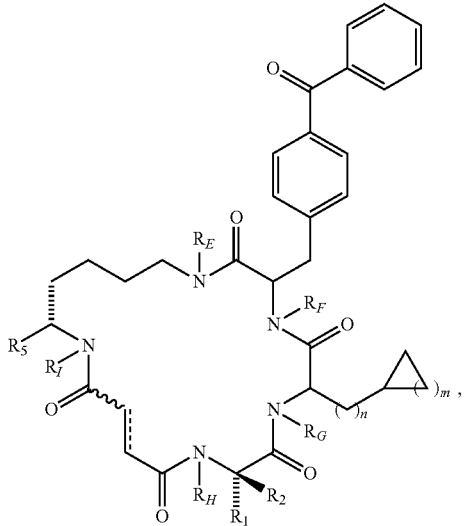

(V)

or pharmaceutically acceptable salts, solvates, hydrates, stereoisomers, polymorphs, tautomers, isotopically enriched forms, and prodrugs thereof, wherein each instance of $R_1$, $R_2$, $R_5$, $R_E$, $R_F$, $R_G$, $R_H$, and $R_I$ are as defined in Formula (I). In certain embodiments of Formula (V), $R_1$ represents —H, —$CH_3$, —$CH_2$—$CH_2$—C(=O)—$NH_2$, —$CH_2$—$CH_2$—$CH_2$—NH—C(=NH)—$NH_2$, —$(CH_2)_p$-cyclohexyl, —$(CH_2)_p$-cyclopentyl, —$(CH_2)_p$-cyclobutyl, —$(CH_2)_p$-cyclopropyl, —$(CH_2)_p$-phenyl, halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —$OR^K$, —$N(R^L)_2$, —$SR^K$, —C(=O)$R^K$, —C(=O)$OR^K$, —C(=O)$SR^K$, —C(=O)$N(R^L)_2$, —OC(=O)$R^K$, —OC(=O)$OR^K$, —OC(=O)$SR^K$, —OC(=O)$N(R^L)_2$, —$NR^L$C(=O)$R^L$, —$NR^L$C(=O)$OR^K$, —$NR^L$C(=O)$SR^K$, —$NR^L$C(=O)$N(R^L)_2$, —SC(=O)$R^K$, —SC(=O)$OR^K$, —SC(=O)$SR^K$, —SC(=O)$N(R^L)_2$, —C(=$NR^L$)$R^K$, —C(=$NR^L$)$OR^K$, —C(=$NR^L$)$SR^K$, —C(=$NR^L$)$N(R^L)_2$, —OC(=$NR^L$)$R^K$, —OC(=$NR^L$)$OR^K$, —OC(=$NR^L$)$SR^K$, —OC(=$NR^L$)$N(R^L)_2$, —$NR^L$C(=$NR^L$)$R^{43}$, —$NR^L$C(=$NR^L$)$OR^K$, —$NR^L$C(=$NR^L$)$SR^K$, —$NR^L$C(=$NR^L$)$N(R^L)_2$, —SC(=$NR^L$)$R^K$, —SC(=$NR^L$)$OR^K$, —SC(=$NR^L$)$SR^K$, —SC(=$NR^L$)$N(R^L)_2$, —C(=S)$R^K$, —C(=S)$OR^K$, —C(=S)$SR^K$, —C(=S)$N(R^L)_2$, —OC(=S)$R^K$, —OC(=S)$OR^K$, —OC(=S)$SR^K$, —OC(=S)$N(R^L)_2$, —$NR^L$C(=S)$R^L$, —$NR^L$C(=S)$OR^K$, —$NR^L$C(=S)$SR^K$, —$NR^L$C(=S)$N(R^L)_2$, —SC(=S)$R^K$, —SC(=S)$OR^K$, —SC(=S)$SR^K$, —SC(=S)$N(R^L)_2$, —S(=O)$R^K$, —$SO_2R^K$, —$NR^L SO_2R^K$, —$SO_2N(R^L)_2$, —$N_3$, —CN, —SCN, and —$NO_2$, wherein each occurrence of $R^K$ is independently hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl; and each occurrence of $R^L$ is independently hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl; in linear or cyclic form; or a nitrogen protecting group; and each occurrence of p is independently 0 or an integer between 1 and 10 inclusive;

$R_2$ represents —H or $(CH_2)_q$—$CH_3$, wherein q is 0 or an integer between 1 and 10 inclusive;

$R_5$ represents C(=O)$NH_2$, or $CH_2$—C(=O)$NH_2$; and wherein n is 0 or an integer between 1 and 10 inclusive,
m is an integer between 1 and 5 inclusive; and ----- is a double C—C bond, in either the cis or trans configuration.

In some embodiments, the macrocyclic IDE inhibitors provided herein are trans-olefins of formula (V), as provided by formula (VI):

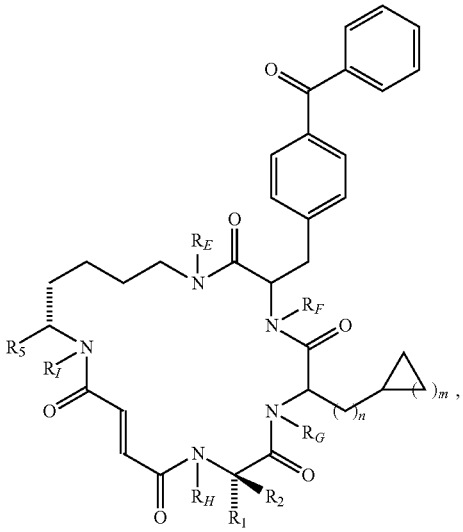

(VI)

or pharmaceutically acceptable salts, solvates, hydrates, stereoisomers, polymorphs, tautomers, isotopically enriched forms, and prodrugs thereof, wherein each instance of $R_1$, $R_2$, $R_E$, $R_F$, $R_G$, $R_H$, and $R_I$ are as defined in Formula (I). In certain embodiments of Formula (VI), $R_1$ represents —H, —$CH_3$, —$CH_2$—$CH_2$—C(=O)—$NH_2$, —$CH_2$—$CH_2$—$CH_2$—NH—C(=NH)—$NH_2$, —$(CH_2)_p$-cyclohexyl, —$(CH_2)_p$-cyclopentyl, —$(CH_2)_p$-cyclobutyl, —$(CH_2)_p$-cyclopropyl, —$(CH_2)_p$-phenyl, halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —OR$^K$, —N(R$^L$)$_2$, SR$^K$, —C(=O)R$^K$, —C(=O)OR$^K$, —C(=O)SR$^K$, —C(=O)N(R$^L$)$_2$, —OC(=O)R$^K$, —OC(=O)OR$^K$, —OC(=O)SR$^K$, —OC(=O)N(R$^L$)$_2$, —NR$^L$C(=O)R$^L$, —NR$^L$C(=O)OR$^K$, —NR$^L$C(=O)SR$^K$, —NR$^L$C(=O)N(R$^L$)$_2$, —SC(=O)R$^K$, —SC(=O)OR$^K$, —SC(=O)SR$^K$, —SC(=O)N(R$^L$)$_2$, —C(=NR$^L$)R$_K$, —C(=NR$^L$)OR$^K$, —C(=NR$^L$)SR$^K$, —C(=NR$^L$)N(R$^L$)$_2$, —OC(=NR$^L$)R$^K$, —OC(=NR$^L$)OR$^K$, —OC(=NR$^L$)SR$^K$, —OC(=NR$^L$)N(R$^L$)$_2$, —NR$^L$C(=NR$^L$)R$^{43}$, —NR$^L$C(=NR$^L$)OR$^K$, NR$^L$C(=NR$^L$)SR$^K$, NR$^L$C(=NR$^L$)N(R$^L$)$_2$, —SC(=NR$^L$)R$^{43}$, —SC(=NR$^L$)OR$^K$, —SC(=NR$^L$)SR$^K$, —SC(=NR$^L$)N(R$^L$)$_2$, —C(=S)R$^K$, —C(=S)OR$^K$, —C(=S)SR$^K$, —C(=S)N(R$^L$)$_2$, —OC(=S)R$^K$, —OC(=S)OR$^K$, —OC(=S)SR$^K$, —OC(=S)N(R$^L$)$_2$, —NR$^L$C(=S)R$^L$, —NR$^L$C(=S)OR$^K$, —NR$^L$C(=S)SR$^K$, —NR$^L$C(=S)N(R$^L$)$_2$, —SC(=S)R$^K$, —SC(=S)OR$^K$, —SC(=S)SR$^K$, —SC(=S)N(R$^L$)$_2$, —S(=O)R$^K$, —SO$_2$R$^K$, —NR$^L$SO$_2$R$^K$, —SO$_2$N(R$^L$)$_2$, —N$_3$, —CN, —SCN, and —NO$_2$, wherein each occurrence of R$^K$ is independently hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl; and each occurrence of R$^L$ is independently hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl; in linear or cyclic form; or a nitrogen protecting group; and each occurrence of p is independently 0 or an integer between 1 and 10 inclusive;

R$_2$ represents —H or —(CH$_2$)$_q$—CH$_3$, wherein q is 0 or an integer between 1 and 10 inclusive;

R$_5$ represents C(=O)NH$_2$, or CH$_2$—C(=O)NH$_2$; and wherein n is 0 or an integer between 1 and 10 inclusive, m is an integer between 1 and 5 inclusive; and ------ is a double C—C bond, in either the cis or trans configuration.

In some embodiments, the macrocyclic IDE inhibitors provided herein are of Formula (VII):

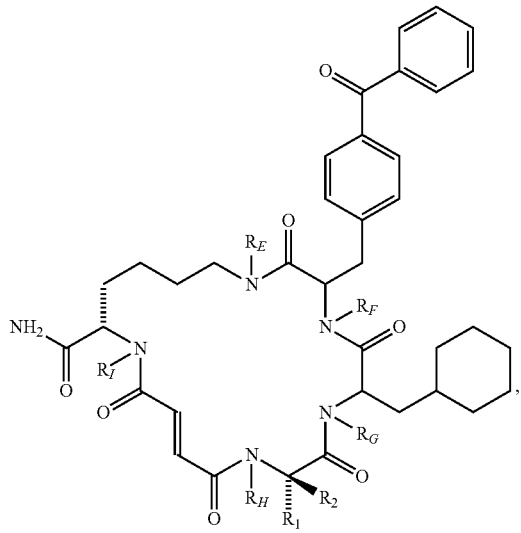

(VII)

or pharmaceutically acceptable salts, solvates, hydrates, stereoisomers, polymorphs, tautomers, isotopically enriched forms, and prodrugs thereof, wherein each instance of R$_1$, R$_2$, R$_E$, R$_F$, R$_G$, R$_H$, and R$_I$ are as defined in Formula (I). In certain embodiments of Formula (VII), R$_1$ represents —H, —CH$_3$, —CH$_2$—CH$_2$—C(=O)—NH$_2$, —CH$_2$—CH$_2$—CH$_2$—NH—C(=NH)—NH$_2$, —(CH$_2$)$_p$-cyclohexyl, —(CH$_2$)$_p$-cyclopentyl, —(CH$_2$)$_p$-cyclobutyl, —(CH$_2$)$_p$-cyclopropyl, —(CH$_2$)$_p$-phenyl, halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —OR$^K$, —N(R$^L$)$_2$, —SR$^K$, —C(=O)R$^K$, —C(=O)OR$^K$, —C(=O)SR$^K$, —C(=O)N(R$^L$)$_2$, —OC(=O)R$^K$, —OC(=O)OR$^K$, —OC(=O)SR$^K$, —OC(=O)N(R$^L$)$_2$, —NR$^L$C(=O)R$^L$, —NR$^L$C(=O)OR$^K$, —NR$^L$C(=O)SR$^K$, —NR$^L$C(=O)N(R$^L$)$_2$, —SC(=O)R$^K$, —SC(=O)OR$^K$, —SC(=O)SR$^K$, —SC(=O)N(R$^L$)$_2$, —C(=NR$^L$)R$^K$, —C(=NR$^L$)OR$^K$, —C(=NR$^L$)SR$^K$, —C(=NR$^L$)N(R$^L$)$_2$, —OC(=NR$^L$)R$^K$, —OC(=NR$^L$)OR$^K$, —OC(=NR$^L$)SR$^K$, —OC(=NR$^L$)N(R$^L$)$_2$, —NR$^L$C(=NR$^L$)R$^{43}$, —NR$^L$C(=NR$^L$)OR$^K$, —NR$^L$C(=NR$^L$)SR$^K$, —NR$^L$C(=NR$^L$)N(R$^L$)$_2$, —SC(=NR$^L$)R$^K$, —SC(=NR$^L$)OR$^K$, —SC(=NR$^L$)SR$^K$, —SC(=NR$^L$)N(R$^L$)$_2$, —C(=S)R$^K$, —C(=S)OR$^K$, —C(=S)SR$^K$, —C(=S)N(R$^L$)$_2$, —OC(=S)R$^K$, —OC(=S)OR$^K$, —OC(=S)SR$^K$, —OC(=S)N(R$^L$)$_2$, —NR$^L$C(=S)R$^L$, —NR$^L$C(=S)OR$^K$, —NR$^L$C(=S)SR$^K$, —NR$^L$C(=S)N(R$^L$)$_2$, —SC(=S)R$^K$, —SC(=S)OR$^K$, —SC(=S)SR$^K$, —SC(=S)N(R$^L$)$_2$, —S(=O)R$^K$, —SO$_2$R$^K$, —NR$^L$SO$_2$R$^K$, —SO$_2$N(R$^L$)$_2$, —N$_3$, —CN, —SCN, and —NO$_2$, wherein each occurrence of R$^K$ is independently hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl; and each occurrence of R$^L$ is independently hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl; in linear or cyclic form; or a nitrogen protecting group; and each occurrence of p is independently 0 or an integer between 1 and 10 inclusive;

R$_2$ represents —H or (CH$_2$)$_q$—CH$_3$, wherein q is 0 or an integer between 1 and 10 inclusive;

R$_5$ represents C(=O)NH$_2$, or CH$_2$—C(=O)NH$_2$; and

------ is a double C—C bond, in either the cis or trans configuration.

The macrocyclic IDE inhibitors provided herein are useful for treating disease as well as for basic research applications. The macrocyclic IDE inhibitors as provided herein are useful for inhibiting IDE activity in vitro or in vivo, for example, in order to increase the stability of insulin in a cell culture or in a subject, e.g., to increase the half-life of insulin in a cell culture or subject. Inhibitors of IDE as provided herein can be used to increase insulin signaling in a subject. For example, IDE inhibitors as provided herein are useful for inhibiting IDE activity in a subject having impaired insulin signaling or exhibiting insulin resistance, for example, a subject having diabetes. IDE inhibitors provided herein are also useful for inhibiting IDE activity in a subject having an aberrant (e.g., lower than normal) level of an IDE substrate other than or in addition to insulin, e.g., of glucagon, amylin, calcitonin-gene related peptide (CGRP), amyloid beta-peptide, TGF-alpha, β-endorphin, somatostatin, or atrial natriuric peptide. According to some aspects of this invention, the IDE inhibitory compounds and methods of their use are useful for inhibiting IDE-mediated insulin catabolism in a subject, for example, in order to ameliorate one or more symptoms of diabetes in a subject. According to some aspects of this invention, the IDE inhibitory compounds and methods of their use are useful for inhibiting IDE-mediated insulin, glucagon, amylin, calcitonin-gene related peptide (CGRP), amyloid beta-peptide, TGF-alpha, β-endorphin, somatostatin, and/or atrial natriuric peptide catabolism in a subject, for example, in order to ameliorate one or more symptoms of a disease or disorder associated with an underabundance of one or more of these IDE substrates.

This disclosure provides in vivo and in vitro methods of inhibiting IDE using the inhibitors described herein. For example, some aspects of the invention provide therapeutic methods using IDE inhibitors in the clinic, e.g., in the context of inhibiting IDE activity in patients having impaired insulin signaling or diabetes. In some embodiments, therapeutic methods using IDE inhibitors in patients having a disease or disorder caused by or associated with an aberrant half-life of a substrate of IDE, or treatable by modulation of the half-life of a substrate of IDE are provided. For example, in some embodiments, the present invention provides therapeutic methods of using IDE inhibitors in patients having an elevated blood pressure or hypertension related to an aberrant level of calcitonin-gene related peptide (CGRP), a potent vasodilator and IDE substrate (see PNAS 2012, 109 (22), 8523-7, the entire contents of which are incorporated herein by reference). Accordingly, the IDE inhibitors provided herein are useful for the modulation of blood pressure and/or the treatment of hypertension.

The IDE inhibitors disclosed herein are believed to not only represent the first examples of synthetic peptidic macrocycles that inhibit IDE, but also the first specific IDE inhibitors, opening the door to targeted therapeutic intervention in patients exhibiting an undesired level of IDE activity or in patients exhibiting impaired insulin signaling or insulin resistance, for example, in patients having diabetes, metabolic syndrome, impaired insulin signaling, or patients having a disease or disorder caused by or associated with an aberrant half-life of a substrate of IDE, or treatable by modulation of the half-life of a substrate of IDE.

Some aspects of this invention provide pharmaceutical compositions comprising a macrocyclic IDE inhibitor described herein, or a pharmaceutically acceptable salt, solvate, hydrate, stereoisomer, polymorph, tautomer, isotopically enriched form, or prodrug thereof, in an amount effective to inhibit IDE in a subject. In some embodiments, the composition further comprises a pharmaceutically acceptable carrier.

Some embodiments provide an in vitro method of inhibiting the activity of an insulin degrading enzyme (IDE) comprising contacting an IDE with a macrocyclic IDE inhibitor described herein, or a pharmaceutically acceptable salt, solvate, hydrate, stereoisomer, polymorph, tautomer, isotopically enriched form, or prodrug thereof. Some embodiments provide an in vivo method of inhibiting the activity of an insulin degrading enzyme (IDE) comprising contacting an IDE with a macrocyclic IDE inhibitor described herein, or a pharmaceutically acceptable salt, solvate, hydrate, stereoisomer, polymorph, tautomer, isotopically enriched form, or prodrug thereof. In some embodiments, the contacting results in the inhibition of the IDE activity to less than about 50%, less than about 25%, less than about 20%, less than about 10%, less than about 9%, less than about 8%, less than about 7%, less than about 6%, less than about 5%, less than about 4%, less than about 3%, less than about 2%, less than about 1%, less than about 0.1%, less than about 0.01%, or less than about 0.001% of the IDE activity as compared to the activity in the absence of the macrocyclic IDE inhibitor or the composition. The in vivo methods of inhibiting the activity of IDE typically include contacting the IDE with the macrocyclic IDE inhibitor, the pharmaceutically acceptable salt, solvate, hydrate, stereoisomer, polymorph, tautomer, isotopically enriched form, or prodrug thereof, or the composition in a subject. In some embodiments, the subject exhibits impaired insulin signaling or insulin resistance. In some embodiments, the subject has diabetes. In some embodiments, the subject has a disease or disorder that is caused by or associated with an aberrant half-life of a substrate of IDE (e.g., insulin, glucagon, amylin, calcitonin-gene related peptide (CGRP), amyloid beta-peptide, TGF-alpha, β-endorphin, somatostatin, and/or atrial natriuric peptide), or that is treatable by modulation of the half-life of a substrate of IDE. In some embodiments, the contacting comprises administering the compound or the composition to the subject. In some embodiments, the macrocyclic IDE inhibitor or composition is administered in an amount effective to reduce an IDE activity in the subject to less than about 50%, less than about 25%, less than about 20%, less than about 10%, less than about 9%, less than about 8%, less than about 7%, less than about 6%, less than about 5%, less than about 4%, less than about 3%, less than about 2%, less than about 1%, less than about 0.1%, less than about 0.01%, or less than about 0.001% of the IDE activity as compared to the IDE activity in the absence of the compound, the salt thereof, or the composition. In some embodiments, the IDE activity is plasma IDE activity and/or pancreas IDE activity. In some embodiments, the IDE activity is liver IDE activity and/or kidney IDE activity. In some embodiments, the IDE activity is IDE activity in a tissue where IDE is expressed. In some embodiments, the IDE activity is IDE activity in a tissue where catabolism of an IDE substrate takes place. In some embodiments, the IDE activity is IDE activity in a tissue that is reactive to an IDE substrate, e.g., an insulin-reactive tissue, a glucagon-reactive tissue, and so on. In some embodiments, the subject is a mammal. In some embodiments, the subject is a human.

Some aspects of this invention provide a method of treating a disease, disorder, or condition associated with aberrant IDE activity, impaired insulin signaling, or insulin resistance. In some embodiments, the method comprises administering a therapeutically effective amount of a macrocyclic IDE inhibitor described herein, or a pharmaceutically acceptable salt, solvate, hydrate, stereoisomer, polymorph, tautomer, isotopically enriched form, or prodrug thereof, or a pharmaceutical composition comprising the IDE inhibitor. In some embodiments, the subject exhibits an undesirable IDE activity, an undesirable level of IDE activity, or an undesirable level of a product of a reaction mediated by IDE catalytic activity. In some embodiments, the subject exhibits impaired insulin signaling or insulin resistance. In some embodiments, the macrocyclic IDE inhibitor, or the pharmaceutically acceptable salt, solvate, hydrate, stereoisomer, polymorph, tautomer, isotopically enriched form, or prodrug thereof, or the pharmaceutical composition, is administered to the subject based on the subject exhibiting an undesirable level of IDE activity or an undesirable level of a product of a reaction mediated by IDE catalytic activity. In some embodiments, the macrocyclic IDE inhibitor, or the pharmaceutically acceptable salt, solvate, hydrate, stereoisomer, polymorph, tautomer, isotopically enriched form, or prodrug thereof, or the pharmaceutical composition is administered to the subject based on the subject exhibiting impaired insulin signaling or insulin resistance. In some embodiments, the aberrant IDE activity, or the impaired insulin signaling, is a pathological level of IDE activity, a pathological level of insulin signaling impairment, respectively. In some embodiments, the subject exhibits or has been diagnosed with diabetes. In some embodiments, the subject exhibits or has been diagnosed with metabolic syndrome. In some embodiments, the subject exhibits, has been diagnosed with, or is at risk of developing Alzheimer's Disease.

Other advantages, features, and uses of the invention will be apparent from the detailed description of certain non-limiting embodiments; the drawings, the examples; and the claims.

BRIEF DESCRIPTION OF THE DRAWINGS

FIG. 2. In vitro selection of the DNA-templated macrocycle library against IDE. a) Plot of enrichment vs. abundance for two independent selections of the library against IDE. b) Structures of enriched macrocycles. Numbering corresponds to that used in FIG. 2a.

DEFINITIONS

Chemical Definitions

Figure 1:
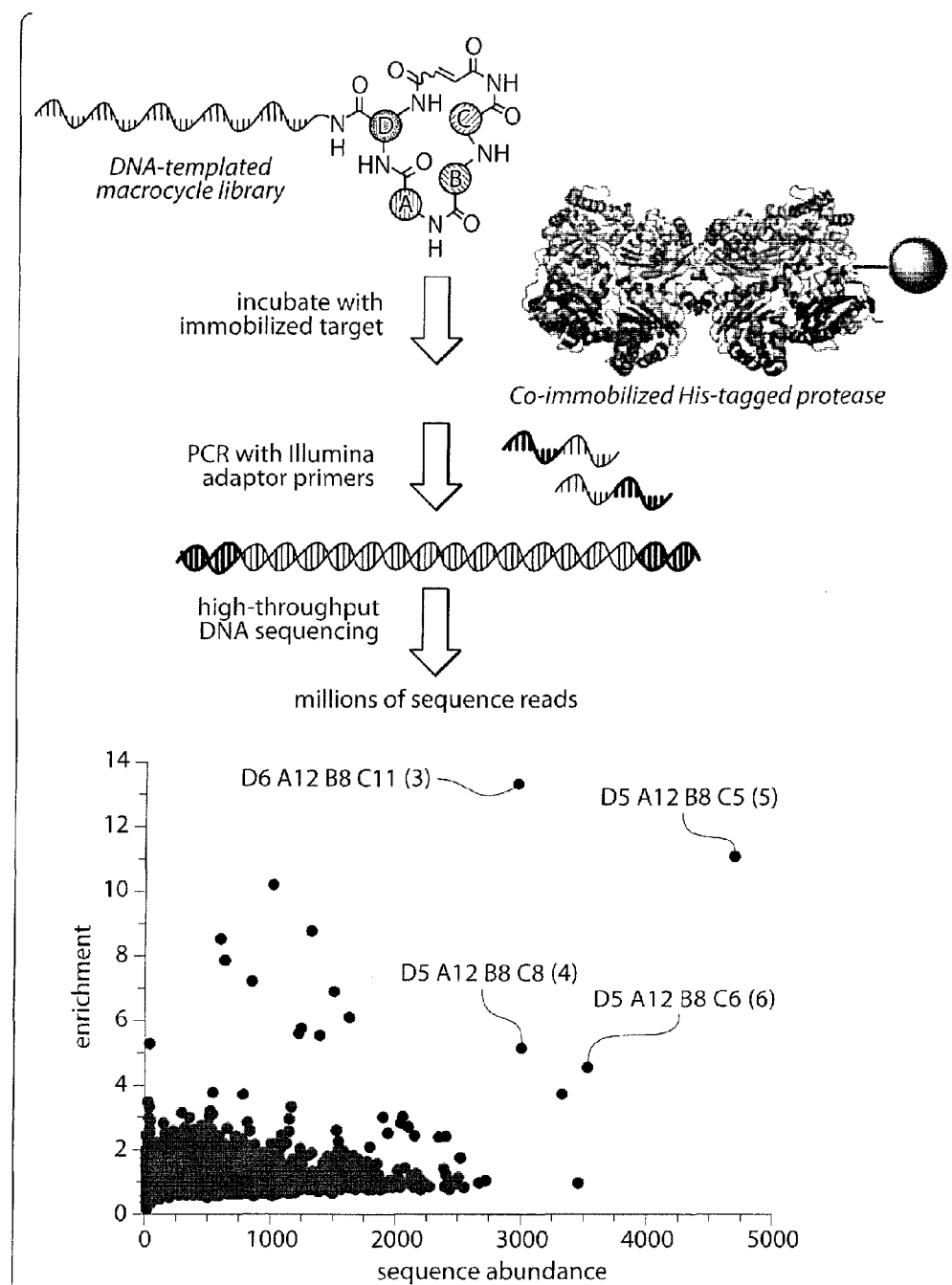
FIG. 1. Overview of in vitro selection of a DNA-templated library against an immobilized protein target.

Definitions of specific functional groups and chemical terms are described in more detail below. For purposes of this invention, the chemical elements are identified in accordance with the Periodic Table of the Elements, CAS version, *Handbook of Chemistry and Physics*, 75th Ed., inside cover, and specific functional groups are generally defined as described therein. Additionally, general principles of organic chemistry, as well as specific functional moieties and reactivity, are described in *Organic Chemistry*, Thomas Sorrell, University Science Books, Sausalito, 1999; Smith and March, *March's Advanced Organic Chemistry*, 5th Edition, John Wiley & Sons, Inc., New York, 2001; Larock, *Comprehensive Organic Transformations*, VCH Publishers, Inc., New York, 1989; and Carruthers, *Some Modern Methods of Organic Synthesis*, 3rd Edition, Cambridge University Press, Cambridge, 1987. The entire contents of each references cited in this paragraph are incorporated by reference.

Compounds described herein can comprise one or more asymmetric centers, and thus can exist in various isomeric forms, e.g., enantiomers and/or diastereomers. For example, the compounds described herein can be in the form of an individual enantiomer, diastereomer or geometric isomer, or can be in the form of a mixture of stereoisomers, including racemic mixtures and mixtures enriched in one or more stereoisomer. Isomers can be isolated from mixtures by methods known to those skilled in the art, including chiral high pressure liquid chromatography (HPLC) and the formation and crystallization of chiral salts; or preferred isomers can be prepared by asymmetric syntheses. See, for example, Jacques et al., *Enantiomers, Racemates and Resolutions* (Wiley Interscience, New York, 1981); Wilen et al., *Tetrahedron* 33:2725 (1977); Eliel, *Stereochemistry of Carbon Compounds* (McGraw Hill, NY, 1962); and Wilen, *Tables of Resolving Agents and Optical Resolutions*, p. 268 (E. L. Eliel, Ed., Univ. of Notre Dame Press, Notre Dame, Ind. 1972). The invention additionally encompasses compounds described herein as individual isomers substantially free of other isomers, and alternatively, as mixtures of various isomers.

Where an isomer/enantiomer is preferred, it may, in some embodiments, be provided substantially free of the corresponding enantiomer and may also be referred to as "optically enriched." "Optically enriched," as used herein, means that the compound is made up of a significantly greater proportion of one enantiomer. In certain embodiments, the compound of the present invention is made up of at least about 90% by weight of a preferred enantiomer. In other embodiments the compound is made up of at least about 95%, 98%, or 99% by weight of a preferred enantiomer. Preferred enantiomers may be isolated from racemic mixtures by any method known to those skilled in the art, including chiral high pressure liquid chromatography (HPLC) and the formation and crystallization of chiral salts or prepared by asymmetric syntheses. See, for example, Jacques et al., *Enantiomers, Racemates and Resolutions* (Wiley Interscience, New York, 1981); Wilen et al., *Tetrahedron* 33:2725 (1977); Eliel, *Stereochemistry of Carbon Compounds* (McGrawHill, NY, 1962); Wilen, *Tables of Resolving Agents and Optical Resolutions*, p. 268 (E. L. Eliel, Ed., Univ. of Notre Dame Press, Notre Dame, Ind. 1972).

When a range of values is listed, it is intended to encompass each value and sub-range within the range. For example "$C_{1-6}$ alkyl" is intended to encompass, $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$ alkyl.

The term "aliphatic," as used herein, includes both saturated and unsaturated, straight chain (i.e., unbranched), branched, acyclic, and cyclic (i.e., carbocyclic) hydrocarbons, which are optionally substituted with one or more functional groups. It is understood from the above description that the term "aliphatic," whether preceded by the terms substituted or unsubstituted, and unless otherwise specified, encompasses "cyclic or acyclic" and "branched or unbranched" groups. As will be appreciated by one of ordinary skill in the art, "aliphatic" is intended herein to include, but is not limited to, alkyl, alkenyl, alkynyl, and carbocyclyl (cycloalkyl, cycloalkenyl, and cycloalkynyl) moieties. In certain embodiments, as used herein, "aliphatic" is used to indicate those aliphatic groups (cyclic, acyclic, substituted, unsubstituted, branched or unbranched) having 1-20 carbon atoms. Unless otherwise specified, each instance of an aliphatic group is independently unsubstituted or substituted with one or more substituents, as valency permits, and which results in a stable compound. Exemplary substituents are further described herein.

The term "alkyl" refers to a radical of a straight-chain or branched saturated hydrocarbon group having from 1 to 20 carbon atoms ("$C_{1-20}$ alkyl"). In some embodiments, an alkyl group has 1 to 10 carbon atoms ("$C_{1-10}$ alkyl"). In some embodiments, an alkyl group has 1 to 9 carbon atoms ("$C_{1-9}$ alkyl"). In some embodiments, an alkyl group has 1 to 8 carbon atoms ("$C_{1-8}$ alkyl"). In some embodiments, an alkyl group has 1 to 7 carbon atoms ("$C_{1-7}$ alkyl"). In some embodiments, an alkyl group has 1 to 6 carbon atoms ("$C_{1-6}$ alkyl"). In some embodiments, an alkyl group has 1 to 5 carbon atoms ("$C_{1-5}$ alkyl"). In some embodiments, an alkyl group has 1 to 4 carbon atoms ("$C_{1-4}$ alkyl"). In some embodiments, an alkyl group has 1 to 3 carbon atoms ("$C_{1-3}$ alkyl"). In some embodiments, an alkyl group has 1 to 2 carbon atoms ("$C_{1-2}$ alkyl"). In some embodiments, an alkyl group has 1 carbon atom ("$C_1$ alkyl"). In some embodiments, an alkyl group has 2 to 6 carbon atoms ("$C_{2-6}$ alkyl"). Examples of $C_{1-6}$ alkyl groups include methyl ($C_1$), ethyl ($C_2$), n-propyl ($C_3$), isopropyl ($C_3$), n-butyl ($C_4$), tert-butyl ($C_4$), sec-butyl ($C_4$), iso-butyl ($C_4$), n-pentyl ($C_5$), 3-pentanyl ($C_5$), amyl ($C_5$), neopentyl ($C_5$), 3-methyl-2-butanyl ($C_5$), tertiary amyl ($C_5$), n-hexyl ($C_6$), and the like, which may bear one or more substituents. Additional examples of alkyl groups include n-heptyl ($C_7$), n-octyl ($C_8$) and the like, which may bear one or more substituents. Unless otherwise specified, each instance of an alkyl group is independently unsubstituted or substituted with one or more substituents, as valency permits, and which results in a stable compound. Exemplary substituents are further described herein.

The term "perhaloalkyl" is a substituted alkyl group as defined herein wherein all of the hydrogen atoms are independently replaced by a halogen, e.g., fluoro, bromo, chloro, or iodo. In some embodiments, the alkyl moiety has 1 to 8 carbon atoms ("$C_{1-8}$ perhaloalkyl"). In some embodiments, the alkyl moiety has 1 to 6 carbon atoms ("$C_{1-6}$ perhaloalkyl"). In some embodiments, the alkyl moiety has 1 to 4 carbon atoms ("$C_{1-4}$ perhaloalkyl"). In some embodiments, the alkyl moiety has 1 to 3 carbon atoms ("$C_{1-3}$ perhaloalkyl"). In some embodiments, the alkyl moiety has 1 to 2 carbon atoms ("$C_{1-2}$ perhaloalkyl"). In some embodiments, all of the hydrogen atoms are replaced with fluoro. In some embodiments, all of the hydrogen atoms are replaced with chloro. Examples of perhaloalkyl groups include —$CF_3$, —$CF_2CF_3$, —$CF_2CF_2CF_3$, —$CCl_3$, —$CFCl_2$, —$CF_2Cl$, and the like.

The term "alkenyl" refers to a radical of a straight-chain or branched hydrocarbon group having from 2 to 20 carbon atoms, one or more carbon-carbon double bonds, and no triple bonds ("$C_{2-20}$ alkenyl"). In some embodiments, an alkenyl group has 2 to 10 carbon atoms ("$C_{2-10}$ alkenyl"). In some embodiments, an alkenyl group has 2 to 9 carbon atoms ("$C_{2-9}$ alkenyl"). In some embodiments, an alkenyl group has 2 to 8 carbon atoms ("$C_{2-8}$ alkenyl"). In some embodiments, an alkenyl group has 2 to 7 carbon atoms ("$C_{2-7}$ alkenyl"). In some embodiments, an alkenyl group has 2 to 6 carbon atoms ("$C_{2-6}$ alkenyl"). In some embodiments, an alkenyl group has 2 to 5 carbon atoms ("$C_{2-5}$ alkenyl"). In some embodiments, an alkenyl group has 2 to 4 carbon atoms ("$C_{2-4}$ alkenyl"). In some embodiments, an alkenyl group has 2 to 3 carbon atoms ("$C_{2-3}$ alkenyl"). In some embodiments, an alkenyl group has 2 carbon atoms ("$C_2$ alkenyl"). The one or more carbon-carbon double bonds can be internal (such as in 2-butenyl) or terminal (such as in 1 Examples of $C_{2-4}$ alkenyl groups include ethenyl ($C_2$), 1-propenyl ($C_3$), 2-propenyl ($C_3$), 1-butenyl ($C_4$), 2-butenyl ($C_4$), butadienyl ($C_4$), and the like, which may bear one or more substituents. Examples of $C_{2-6}$ alkenyl groups include the aforementioned $C_{2-4}$ alkenyl groups as well as pentenyl ($C_5$), pentadienyl ($C_5$), hexenyl ($C_6$), and the like, which may bear one or more substituents. Additional examples of alkenyl include heptenyl ($C_7$), octenyl ($C_8$), octatrienyl ($C_8$), and the like, which may bear one or more substituents. Unless otherwise specified, each instance of an alkenyl group is independently unsubstituted or substituted with one or more substituents, as valency permits, and which results in a stable compound. Exemplary substituents are further described herein.

The term "alkynyl" refers to a radical of a straight-chain or branched hydrocarbon group having from 2 to 20 carbon atoms, one or more carbon-carbon triple bonds, and optionally one or more double bonds ("$C_{2-20}$ alkynyl"). In some embodiments, an alkynyl group has 2 to 10 carbon atoms ("$C_{2-10}$ alkynyl"). In some embodiments, an alkynyl group has 2 to 9 carbon atoms ("$C_{2-9}$ alkynyl"). In some embodiments, an alkynyl group has 2 to 8 carbon atoms ("$C_{2-8}$ alkynyl"). In some embodiments, an alkynyl group has 2 to 7 carbon atoms ("$C_{2-7}$ alkynyl"). In some embodiments, an alkynyl group has 2 to 6 carbon atoms ("$C_{2-6}$ alkynyl"). In some embodiments, an alkynyl group has 2 to 5 carbon atoms ("$C_{2-5}$ alkynyl"). In some embodiments, an alkynyl group has 2 to 4 carbon atoms ("$C_{2-4}$ alkynyl"). In some embodiments, an alkynyl group has 2 to 3 carbon atoms ("$C_{2-3}$ alkynyl"). In some embodiments, an alkynyl group has 2 carbon atoms ("$C_2$ alkynyl"). The one or more carbon-carbon triple bonds can be internal (such as in 2-butynyl) or terminal (such as in 1 Examples of $C_{2-4}$ alkynyl groups include, without limitation, ethynyl ($C_2$), 1 ($C_3$), 2-propynyl ($C_3$), 1-butynyl ($C_4$), 2-butynyl ($C_4$), and the like, which may bear one or more substituents. Examples of $C_{2-6}$ alkenyl groups include the aforementioned $C_{2-4}$ alkynyl groups as well as pentynyl ($C_5$), hexynyl ($C_6$), and the like, which may bear one or more substituents. Additional examples of alkynyl include heptynyl ($C_7$), octynyl ($C_8$), and the like, which may bear one or more substituents. Unless otherwise specified, each instance of an alkynyl group is independently unsubstituted or substituted with one or more substituents, as valency permits, and which results in a stable compound. Exemplary substituents are further described herein.

The term "carbocyclyl" or "carbocyclic" refers to a radical of a nonaromatic cyclic hydrocarbon group having from 3 to 10 ring carbon atoms ("$C_{3-10}$ carbocyclyl") and zero heteroatoms in the nonaromatic ring system. In some embodiments, a carbocyclyl group has 3 to 8 ring carbon atoms ("$C_{3-8}$ carbocyclyl"). In some embodiments, a carbocyclyl group has 3 to 6 ring carbon atoms ("$C_{3-6}$ carbocyclyl"). In some embodiments, a carbocyclyl group has 3 to 6 ring carbon atoms ("$C_{3-6}$ carbocyclyl"). In some embodiments, a carbocyclyl group has 5 to 10 ring carbon atoms ("$C_{5-10}$ carbocyclyl"). Exemplary $C_{3-6}$ h explicitly herein. cyclobutyl ($C_4$), cyclobutenyl ($C_4$), cyclopentyl ($C_5$), cyclopentenyl ($C_5$), cyclohexyl ($C_6$), cyclohexenyl ($C_6$), cyclohexadienyl ($C_6$), and the like. Exemplary $C_{3-8}$ carbocyclyl groups include, without limitation, the aforementioned $C_{3-6}$ carbocyclyl groups as well as cycloheptyl ($C_7$), cycloheptenyl ($C_7$), cycloheptadienyl ($C_7$), cycloheptatrienyl ($C_7$), cyclooctyl ($C_8$), cyclooctenyl ($C_8$), bicyclo[2.2.1]heptanyl ($C_7$), bicyclo[2.2.2]octanyl ($C_8$), and the like. Exemplary $C_{3-10}$ carbocyclyl groups include, without limitation, the aforementioned $C_{3-8}$ carbocyclyl groups as well as cyclononyl ($C_9$), cyclononenyl ($C_9$), cyclodecyl ($C_{10}$), cyclodecenyl ($C_{10}$), octahydro-1H-indenyl ($C_9$), decahydronaphthalenyl ($C_{10}$), spiro[4.5]decanyl ($C_{10}$), and the like. As the foregoing examples illustrate, in certain embodiments, the carbocyclyl group is either monocyclic ("monocyclic carbocyclyl") or contain a fused, bridged or spiro ring system such as a bicyclic system ("bicyclic carbocyclyl") and can be saturated or can be partially unsaturated. "Carbocyclyl" also includes ring systems wherein the carbocyclyl ring, as defined herein, is fused with one or more aryl or heteroaryl groups wherein the point of attachment is on the carbocyclyl ring, and in such instances, the number of carbons continue to designate the number of carbons in the carbocyclic ring system. Unless otherwise specified, each instance of a carbocyclyl group is independently unsubstituted or substituted with one or more substituents, as valency permits, and which results in a stable compound. Exemplary substituents are further described herein.

In some embodiments, "carbocyclyl" is a monocyclic, saturated carbocyclyl group having from 3 to 10 ring carbon atoms ("$C_{3-10}$ cycloalkyl"). In some embodiments, a cycloalkyl group has 3 to 8 ring carbon atoms ("$C_{3-8}$ cycloalkyl"). In some embodiments, a cycloalkyl group has 3 to 6 ring carbon atoms ("$C_{3-6}$ cycloalkyl"). In some embodiments, a cycloalkyl group has 5 to 6 ring carbon atoms ("$C_{5-6}$ cycloalkyl"). In some embodiments, a cycloalkyl group has 5 to 10 ring carbon atoms ("$C_{5-10}$ cycloalkyl"). Examples of $C_{5-6}$ cycloalkyl groups include cyclopentyl ($C_5$) and cyclohexyl ($C_5$). Examples of $C_{3-6}$ cycloalkyl groups include the aforementioned $C_{5-6}$ cycloalkyl groups as well as cyclopropyl ($C_3$) and cyclobutyl ($C_4$). Examples of $C_{3-8}$ cycloalkyl groups include the aforementioned $C_{3-6}$ cycloalkyl groups as well as cycloheptyl ($C_7$) and cyclooctyl ($C_8$). Unless otherwise specified, each instance of a cycloalkyl group is independently unsubstituted or substituted with one or more substituents, as valency permits, and which results in a stable compound. Exemplary substituents are further described herein.

The term "heteroaliphatic," as used herein, refers to an aliphatic moiety, as defined herein, which includes both saturated and unsaturated, nonaromatic, straight chain (i.e., unbranched), branched, acyclic or cyclic (i.e., heterocyclic) groups which are optionally substituted with one or more substituents, and which contain one or more oxygen, sulfur, nitrogen, phosphorus, or silicon atoms, e.g., in place of carbon atoms. It is understood from the above description that the term "heteroaliphatic," whether preceded by the terms substituted or unsubstituted, and unless otherwise specified, encompasses "cyclic or acyclic" and "branched or unbranched" groups. It is also understood, similar to aliphatic, that "heteroaliphatic" is intended to encompass heteroalkyl, heteroalkenyl, heteroalkynyl, and heterocyclic (heterocycloalkyl, heterocycloalkenyl, and heterocycloalkynyl) moieties. The terms "heteroalkyl," "heteroalkenyl," and "heteroalkynyl" are defined similarly, i.e., respectively refer to an alkyl, alkenyl, and alkynyl group, as defined herein, which are optionally substituted with one or more substituents, and which contain one or more oxygen, sulfur, nitrogen, phosphorus, or silicon atoms, e.g., in place of carbon atoms. Unless otherwise specified, each instance of a heteroaliphatic group is independently unsubstituted or substituted with one or more substituents, as valency permits, and which results in a stable compound. Exemplary substituents are further described herein.

The term "heterocyclic," "heterocycles," or "heterocyclyl," as used herein, refers to a cyclic heteroaliphatic group. A heterocyclic group refers to a nonaromatic, partially unsaturated or fully saturated, 3- to 10-membered ring system, which includes single rings of 3 to 8 atoms in size, and bi- and tri-cyclic ring systems which may include aromatic five- or six-membered aryl or heteroaryl groups fused to a nonaromatic ring. These heterocyclic rings include those having from one to four heteroatoms independently selected from oxygen, sulfur, and nitrogen, in which the nitrogen and sulfur heteroatoms may optionally be oxidized and the nitrogen heteroatom may optionally be quaternized. In certain embodiments, the term heterocyclic refers to a nonaromatic 5-, 6-, or 7-membered ring or polycyclic group wherein at least one ring atom is a heteroatom selected from O, S, and N (wherein the nitrogen and sulfur heteroatoms may be optionally oxidized), and the remaining ring atoms are carbon, the radical being joined to the rest of the molecule via any of the ring atoms. Heterocycyl groups include, but are not limited to, a bi or tricyclic group, comprising fused five, six, or seven-membered rings having between one and three heteroatoms independently selected from the oxygen, sulfur, and nitrogen, wherein (i) each 5-membered ring has 0 to 2 double bonds, each 6-membered ring has 0 to 2 double bonds, and each 7-membered ring has 0 to 3 double bonds, (ii) the nitrogen and sulfur heteroatoms may be optionally oxidized, (iii) the nitrogen heteroatom may optionally be quaternized, and (iv) any of the above heterocyclic rings may be fused to an aryl or heteroaryl ring. In the instance of ring fusion, it is understood that "heterocyclyl" refers to a ring system wherein the heterocyclyl ring, as defined herein, is fused with one or more carbocyclyl groups wherein the point of attachment is either on the carbocyclyl or heterocyclyl ring, or ring systems wherein the heterocyclyl ring, as defined herein, is fused with one or more aryl or heteroaryl groups, wherein the point of attachment is on the heterocyclyl ring, and in such instances, the number of ring members continue to designate the number of ring members in the heterocyclyl ring system. Unless otherwise specified, each instance of a heterocyclyl group is independently unsubstituted or substituted with one or more substituents, as valency permits, and which results in a stable compound. Exemplary substituents are further described herein.

In some embodiments, a heterocyclyl group is a 5- to 10-membered non aromatic ring system having ring carbon atoms and 1-4 ring heteroatoms, wherein each heteroatom is independently selected from nitrogen, oxygen, and sulfur ("5- to 10-membered heterocyclyl"). In some embodiments, a heterocyclyl group is a 5- to 8-membered non aromatic ring system having ring carbon atoms and 1-4 ring heteroatoms, wherein each heteroatom is independently selected from nitrogen, oxygen, and sulfur ("5- to 8-membered heterocyclyl"). In some embodiments, a heterocyclyl group is a 5- to 6-membered non aromatic ring system having ring carbon atoms and 1-4 ring heteroatoms, wherein each heteroatom is independently selected from nitrogen, oxygen, and sulfur ("5- to 6-membered heterocyclyl"). In some embodiments, the 5-6 membered heterocyclyl has 1-3 ring heteroatoms selected from nitrogen, oxygen, and sulfur. In some embodiments, the 5- to 6-membered heterocyclyl has 1-2 ring heteroatoms selected from nitrogen, oxygen, and sulfur. In some embodiments, the 5-6 membered heterocyclyl has one ring heteroatom selected from nitrogen, oxygen, and sulfur.

Exemplary 3-membered heterocyclyl groups containing one heteroatom include, without limitation, azirdinyl, oxiranyl, thiorenyl. Exemplary 4-membered heterocyclyl groups containing one heteroatom include, without limitation, azetidinyl, oxetanyl and thietanyl. Exemplary 5-membered heterocyclyl groups containing one heteroatom include, without limitation, tetrahydrofuranyl, dihydrofuranyl, tetrahydrothiophenyl, dihydrothiophenyl, pyrrolidinyl, dihydropyrrolyl and pyrrolyl-2,5 Exemplary 5-membered heterocyclyl groups containing two heteroatoms include, without limitation, dioxolanyl, oxasulfuranyl, disulfuranyl, and oxazolidin-2-one. Exemplary 5-membered heterocyclyl groups containing three heteroatoms include, without limitation, triazolinyl, oxadiazolinyl, and thiadiazolinyl. Exemplary 6-membered heterocyclyl groups containing one heteroatom include, without limitation, piperidinyl, tetrahydropyranyl, dihydropyridinyl, and thianyl. Exemplary 6-membered heterocyclyl groups containing two heteroatoms include, without limitation, piperazinyl, morpholinyl, dithianyl, dioxanyl. Exemplary 6-membered heterocyclyl groups containing two heteroatoms include, without limitation, triazinanyl. Exemplary 7-membered heterocyclyl groups containing one heteroatom include, without limitation, azepanyl, oxepanyl and thiepanyl. Exemplary 8-membered heterocyclyl groups containing one heteroatom include, without limitation, azocanyl, oxecanyl and thiocanyl. Exemplary 5-membered heterocyclyl groups fused to a $C_6$ aryl ring (also referred to herein as a 5,6-bicyclic heterocyclic ring) include, without limitation, indolinyl, isoindolinyl, dihydrobenzofuranyl, dihydrobenzothienyl, benzoxazolinonyl, and the like. Exemplary 6-membered heterocyclyl groups fused to an aryl ring (also referred to herein as a 6,6-bicyclic heterocyclic ring) include, without limitation, tetrahydroquinolinyl, tetrahydroisoquinolinyl, and the like.

The term "aryl" refers to a radical of a monocyclic or polycyclic (e.g., bicyclic or tricyclic) 4n+2 aromatic ring system (e.g., having 6, 10, or 14 π electrons shared in a cyclic array) having 6-14 ring carbon atoms and zero heteroatoms provided in the aromatic ring system ("$C_{6-14}$ aryl"). In some embodiments, an aryl group has six ring carbon atoms ("$C_6$ aryl"; e.g., phenyl). In some embodiments, an aryl group has ten ring carbon atoms ("$C_{10}$ aryl"; e.g., naphthyl such as 1-naphthyl and 2-naphthyl). In some embodiments, an aryl group has fourteen ring carbon atoms ("$C_{14}$ aryl"; e.g., anthracyl). "Aryl" also includes ring systems wherein the aryl ring, as defined herein, is fused with one or more carbocyclyl or heterocyclyl groups wherein the radical or point of attachment is on the aryl ring, and in such instances, the number of carbon atoms continue to designate the number of carbon atoms in the aryl ring system. Unless otherwise specified, each instance of an aryl group is independently unsubstituted or substituted with one or more substituents, as valency permits, and which results in a stable compound. Exemplary substituents are further described herein.

The term "heteroaryl" refers to a radical of a 5-10 membered monocyclic or bicyclic 4n+2 aromatic ring system (e.g., having 6 or 10 π electrons shared in a cyclic array) having ring carbon atoms and 1-4 ring heteroatoms provided in the aromatic ring system, wherein each heteroatom is independently selected from nitrogen, oxygen and sulfur ("5-10 membered heteroaryl"). In heteroaryl groups that contain one or more nitrogen atoms, the point of attachment can be a carbon or nitrogen atom, as valency permits. Heteroaryl bicyclic ring systems can include one or more heteroatoms in one or both rings. "Heteroaryl" includes ring systems wherein the heteroaryl ring, as defined herein, is fused with one or more carbocyclyl or heterocyclyl groups wherein the point of attachment is on the heteroaryl ring, and in such instances, the number of ring members continue to designate the number of ring members in the heteroaryl ring system. "Heteroaryl" also includes ring systems wherein the heteroaryl ring, as defined herein, is fused with one or more aryl groups wherein the point of attachment is either on the aryl or heteroaryl ring, and in such instances, the number of ring members designates the number of ring members in the fused (aryl/heteroaryl) ring system. Bicyclic heteroaryl groups wherein one ring does not contain a heteroatom (e.g., indolyl, quinolinyl, carbazolyl, and the like) the point of attachment can be on either ring, i.e., either the ring bearing a heteroatom (e.g., 2-indolyl) or the ring that does not contain a heteroatom (e.g., 5-indolyl). Unless otherwise specified, each instance of a heteroaryl group is independently unsubstituted or substituted with one or more substituents, as valency permits, and which results in a stable compound. Exemplary substituents are further described herein.

In some embodiments, a heteroaryl group is a 5-10 membered aromatic ring system having ring carbon atoms and 1-4 ring heteroatoms provided in the aromatic ring system, wherein each heteroatom is independently selected from nitrogen, oxygen, and sulfur ("5-10 membered heteroaryl"). In some embodiments, a heteroaryl group is a 5-8 membered aromatic ring system having ring carbon atoms and 1-4 ring heteroatoms provided in the aromatic ring system, wherein each heteroatom is independently selected from nitrogen, oxygen, and sulfur ("5-8 membered heteroaryl"). In some embodiments, a heteroaryl group is a 5-6 membered aromatic ring system having ring carbon atoms and 1-4 ring heteroatoms provided in the aromatic ring system, wherein each heteroatom is independently selected from nitrogen, oxygen, and sulfur ("5-6 membered heteroaryl"). In some embodiments, the 5-6 membered heteroaryl has 1-3 ring heteroatoms selected from nitrogen, oxygen, and sulfur. In some embodiments, the 5-6 membered heteroaryl has 1-2 ring heteroatoms selected from nitrogen, oxygen, and sulfur. In some embodiments, the 5-6 membered heteroaryl has 1 ring heteroatom selected from nitrogen, oxygen, and sulfur. Unless otherwise specified, each instance of a heteroaryl group is independently optionally substituted, i.e., unsubstituted ("unsubstituted heteroaryl") or substituted ("substituted heteroaryl") with one or more substituents. In certain embodiments, the heteroaryl group is unsubstituted 5-14 membered heteroaryl. In certain embodiments, the heteroaryl group is substituted 5-14 membered heteroaryl.

Exemplary 5-membered heteroaryl groups containing one heteroatom include, without limitation, pyrrolyl, furanyl and thiophenyl. Exemplary 5-membered heteroaryl groups containing two heteroatoms include, without limitation, imidazolyl, pyrazolyl, oxazolyl, isoxazolyl, thiazolyl, and isothiazolyl. Exemplary 5-membered heteroaryl groups containing three heteroatoms include, without limitation, triazolyl, oxadiazolyl, and thiadiazolyl. Exemplary 5-membered heteroaryl groups containing four heteroatoms include, without limitation, tetrazolyl. Exemplary 6-membered heteroaryl groups containing one heteroatom include, without limitation, pyridinyl. Exemplary 6-membered heteroaryl groups containing two heteroatoms include, without limitation, pyridazinyl, pyrimidinyl, and pyrazinyl. Exemplary 6-membered heteroaryl groups containing three or four heteroatoms include, without limitation, triazinyl and tetrazinyl, respectively. Exemplary 7-membered heteroaryl groups containing one heteroatom include, without limitation, azepinyl, oxepinyl, and thiepinyl. Exemplary 5,6-bicyclic heteroaryl groups include, without limitation, indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, and purinyl. Exemplary 6,6-bicyclic heteroaryl groups include, without limitation, naphthyridinyl, pteridinyl, quinolinyl, isoquinolinyl, cinnolinyl, quinoxalinyl, phthalazinyl, and quinazolinyl.

The term "acyl," as used herein, refers to a group having the general formula —C(=O)R$^{X5}$, —CO(=O)R$^{X5}$, —C(=O)SR$^{X5}$, —C(=O)N(R$^{X6}$)$_2$, —C(=NR$^{X6}$)R$^{X1}$, C(=NR$^{X6}$)OR$^{X5}$, —C(=NR$^{X6}$)SR$^{X5}$, —C(=NR$^{X6}$)N(R$^{X6}$)$_2$, —C(=S)R$^{X5}$, —C(=S)OR$^{X5}$, —C(=S)SR$^{X5}$, and —C(=S)N(R$^{X6}$)$_2$, wherein each occurrence of R$^{X5}$ is independently hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl; and each occurrence of R$^{X6}$ is independently hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, or a nitrogen protecting group, or two R$^{X6}$ groups are joined to form an substituted or unsubstituted heterocyclic ring.

The term "oxo," as used herein, refers to a group of the formula (=O).

The term "thiooxo," as used herein, refers to a group of the formula (=S).

Aliphatic (alkyl, alkenyl, alkynyl, carbocyclyl), heteroaliphatic (heteroalkyl, heteroalkenyl, heteroalkynyl, heterocyclyl), aryl, and heteroaryl groups, as defined herein, are optionally substituted. "Optionally substituted" refers to a group which may be substituted or unsubstituted. In general, the term "substituted" means that at least one hydrogen present on a group (e.g., a carbon or nitrogen atom) is replaced with a permissible substituent, e.g., a substituent which upon substitution results in a stable moiety or compound, e.g., a compound which does not spontaneously undergo transformation such as by a rearrangement, cyclization, elimination, or other reaction, and preferably possess stability sufficient to allow manufacture, and which maintains its integrity for a sufficient period of time to be useful for the purposes detailed herein. Unless otherwise indicated, a "substituted" group has a substituent at one or more substitutable positions of the group, and when more than one position in any given structure is substituted, the substituent is either the same or different at each position. The term "substituted" is contemplated to include substitution with all permissible substituents of organic compounds, any of the substituents described herein that results in the formation of a stable compound. The present invention contemplates any and all such combinations in order to arrive at a stable compound. For purposes of this invention, heteroatoms may have hydrogen substituents and/or any substituent as described herein which satisfy the valencies of the heteroatom and results in the formation of a stable moiety.

Exemplary substituents include, but are not limited to, any of the substituents described herein, that result in the formation of a stable moiety (e.g., aliphatic, alkyl, alkenyl, alkynyl, heteroaliphatic, heterocyclic, aryl, heteroaryl, acyl, oxo, imino, thiooxo, cyano, isocyano, amino, azido, nitro, hydroxyl, thiol, halo, and combinations thereof, e.g., aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted). Other exemplary substituents are further described herein.

Exemplary carbon atom substituents include, but are not limited to, halogen, —CN, —NO$_2$, —N$_3$, —SO$_2$H, —SO$_3$H, —OH, —OR$^{aa}$, —ON(R$^{bb}$)$_2$, —NH$_4$, —NH(R$^{bb}$), —N(R$^{bb}$)$_2$, —N(R$^{bb}$)$_3$$^+$X$^-$, —N(OR$^{cc}$)R$^{bb}$, —SH, —SR$^{aa}$, —SSR$^{cc}$, —SCN, —NCS, —C(=O)R$^{aa}$, —CO$_2$H, —CHO, —C(OR$^{cc}$)$_2$, —CO$_2$R$^{aa}$, —OC(=O)R$^{aa}$, —OCO$_2$R$^{aa}$, —C(=O)N(R$^{bb}$)$_2$, —OC(=O)N(R$^{bb}$)$_2$, —NR$^{bb}$C(=O)R$^{aa}$, —NR$^{bb}$CO$_2$R$^{aa}$, —NR$^{bb}$C(=O)N(R$^{bb}$)$_2$, —C(=NR$^{bb}$)R$^{aa}$, —C(=NR$^{bb}$)OR$^{aa}$, —OC(=NR$^{bb}$)R$^{aa}$, —OC(=NR$^{bb}$)OR$^{aa}$, —C(=NR$^{bb}$)N(R$^{bb}$)$_2$, —OC(=NR$^{bb}$)N(R$^{bb}$)$_2$, —NR$^{bb}$C(=NR$^{bb}$)N(R$^{bb}$)$_2$, —C(=O)NR$^{bb}$SO$_2$R$^{aa}$, —NR$^{bb}$SO$_2$R$^{aa}$, —SO$_2$N(R$^{bb}$)$_2$, —SO$_2$R$^{aa}$, —SO$_2$OR$^{aa}$, —OSO$_2$R$^{aa}$, —S(=O)R$^{aa}$, —OS(=O)R$^{aa}$, —Si(R$^{aa}$)$_3$, —OSi(R$^{aa}$)$_3$ —C(=S)N(R$^{bb}$)$_2$, —C(=O)SR$^{aa}$, —C(=S)SR$^{aa}$, —SC(=S)SR$^{aa}$, —SC(=O)SR$^{aa}$, —OC(=O)SR$^{aa}$, —SC(=O)R$^{aa}$, —SC(=O)R$^{aa}$, —P(=O)$_2$R$^{aa}$, —OP(=O)$_2$R$^{aa}$, —P(=O)(R$^{aa}$)$_2$, —OP(=O)(R$^{aa}$)$_2$, —OP(=O)(OR$^{cc}$)$_2$, —P(=O)$_2$N(R$^{bb}$)$_2$, —OP(=O)$_2$N(R$^{bb}$)$_2$, —P(=O)(NR$^{bb}$)$_2$, —OP(=O)(NR$^{bb}$)$_2$, —NR$^{bb}$P(=O)(OR$^{cc}$)$_2$, —NR$^{bb}$P(=O)(NR$^{bb}$)$_2$, —P(R$^{cc}$)$_2$, —P(R$^{cc}$)$_3$, —OP(R$^{cc}$)$_2$, —OP(R$^{cc}$)$_3$, —B(R$^{aa}$)$_2$, —B(OR$^{cc}$)$_2$, —BR$^{aa}$(OR$^{cc}$), C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, wherein each alkyl, alkenyl, alkynyl, carbocyclyl, heterocyclyl, aryl, and heteroaryl is independently substituted with 0, 1, 2, 3, 4, or 5 R$^{dd}$ groups;

or two geminal hydrogens on a carbon atom are replaced with the group =O, =S, =NN(R$^{bb}$)$_2$, =NNR$^{bb}$C(=O)R$^{aa}$, =NNR$^{bb}$C(=O)R$^{aa}$, =NNR$^{bb}$S(O)$_2$R$^{aa}$, =NR$^{bb}$, or =NOR$^{cc}$;

each instance of R$^{aa}$ is, independently, selected from C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two R$^{aa}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups;

each instance of R$^{bb}$ is, independently, selected from hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{cc}$)OR$^{aa}$, —C(=NR$^{cc}$)N(R$^{cc}$)$_2$, SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)$_2$R$^{aa}$, —P(=O)(R$^{aa}$)$_2$, —P(=O)$_2$N(R$^{cc}$)$_2$, —P(=O)(NR$^{cc}$)$_2$, C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two R$^{bb}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups;

each instance of R$^{cc}$ is, independently, selected from hydrogen, C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two R$^{cc}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups;

each instance of R$^{dd}$ is, independently, selected from halogen, —CN, —NO$_2$, —N$_3$, —SO$_2$H, —SO$_3$H, —OH, —OR$^{ee}$, —ON(R$^{ff}$)$_2$, —N(R$^{ff}$)$_2$, —N(R$^{ff}$)$_3$$^+$X$^-$, —N(OR$^{ee}$)R$^{ff}$, —SH, —SR$^{ee}$, —SSR$^{ee}$, —C(=O)R$^{ee}$, —CO$_2$H, —CO$_2$R$^{ee}$, —OC(=O)R$^{ee}$, —OCO$_2$R$^{ee}$, —C(=O)N(R$^{ff}$)$_2$, —OC(=O)N(R$^{ff}$)$_2$, —NR$^{ff}$C(=O)R$^{ee}$, —NR$^{ff}$CO$_2$R$^{ee}$, —NR$^{ff}$C(=O)N(R$^{ff}$)$_2$, —C(=NR$^{ff}$)OR$^{ee}$, —OC(=NR$^{ff}$)R$^{ee}$, —OC(=NR$^{ff}$)OR$^{ee}$, —C(=NR$^{ff}$)N(R$^{ff}$)$_2$, —OC(=NR$^{ff}$)N $(R^{ff})_2$, —$NR^{ff}C(=NR^{ff})N(R^{ff})_2$, —$NR^{ff}SO_2R^{ee}$, —$SO_2N(R^{ff})_2$, —$SO_2R^{ee}$, —$SO_2OR^{ee}$, —$OSO_2R^{ee}$, —$S(=O)R^{ee}$, —$Si(R^{ee})_3$, —$OSi(R^{ee})_3$, —$C(=S)N(R^{ff})_2$, —$C(=O)SR^{ee}$, —$C(=S)SR^{ee}$, —$SC(=S)SR^{ee}$, —$P(=O)_2R^{ee}$, —$P(=O)(R^{ee})_2$, —$OP(=O)(R^{ee})_2$, —$OP(=O)(OR^{ee})_2$, $C_{1-6}$ alkyl, $C_{1-6}$ perhaloalkyl, $C_{2-6}$ alkenyl, $C_{2-6}$ alkynyl, $C_{3-10}$ carbocyclyl, 3-10 membered heterocyclyl, $C_{6-10}$ aryl, 5-10 membered heteroaryl, wherein each alkyl, alkenyl, alkynyl, carbocyclyl, heterocyclyl, aryl, and heteroaryl is independently substituted with 0, 1, 2, 3, 4, or 5 $R^{gg}$ groups, or two geminal $R^{dd}$ substituents can be joined to form =O or =S;

each instance of $R^{ee}$ is, independently, selected from $C_{1-6}$ alkyl, $C_{1-6}$ perhaloalkyl, $C_{2-6}$ alkenyl, $C_{2-6}$ alkynyl, $C_{3-10}$ carbocyclyl, $C_{6-10}$ aryl, 3-10 membered heterocyclyl, and 3-10 membered heteroaryl, wherein each alkyl, alkenyl, alkynyl, carbocyclyl, heterocyclyl, aryl, and heteroaryl is independently substituted with 0, 1, 2, 3, 4, or 5 $R^{gg}$ groups;

each instance of $R^{ff}$ is, independently, selected from hydrogen, $C_{1-6}$ alkyl, $C_{1-6}$ perhaloalkyl, $C_{2-6}$ alkenyl, $C_{2-6}$ alkynyl, $C_{3-10}$ carbocyclyl, 3-10 membered heterocyclyl, $C_{6-10}$ aryl and 5-10 membered heteroaryl, or two $R^{ff}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 $R^{gg}$ groups; and each instance of $R^{gg}$ is, independently, halogen, —CN, —$NO_2$, —$N_3$, —$SO_2H$, —$SO_3H$, —OH, —$OC_{1-6}$ alkyl, —$ON(C_{1-6}$ alkyl$)_2$, —$N(C_{1-6}$ alkyl$)_2$, —$N(C_{1-6}$ alkyl$)_3^+X^-$, —$NH(C_{1-6}$ alkyl$)_2^+X^-$, —$NH_2(C_{1-6}$ alkyl$)^+X^-$, —$NH_3^+X^-$, —$N(OC_{1-6}$ alkyl$)(C_{1-6}$ alkyl$)$, —$N(OH)(C_{1-6}$ alkyl$)$, —NH(OH), —SH, —$SC_{1-6}$ alkyl, —$SS(C_{1-6}$ alkyl$)$, —$C(=O)(C_{1-6}$ alkyl$)$, —$CO_2H$, —$CO_2(C_{1-6}$ alkyl$)$, —$OC(=O)(C_{1-6}$ alkyl$)$, —$OCO_2(C_{1-6}$ alkyl$)$, —$C(=O)NH_2$, —$C(=O)N(C_{1-6}$ alkyl$)_2$, —$OC(=O)NH(C_{1-6}$ alkyl$)$, —$NHC(=O)(C_{1-6}$ alkyl$)$, —$N(C_{1-6}$ alkyl$)C(=O)(C_{1-6}$ alkyl$)$, —$NHCO_2(C_{1-6}$ alkyl$)$, —$NHC(=O)N(C_{1-6}$ alkyl$)_2$, —$NHC(=O)NH(C_{1-6}$ alkyl$)$, —$NHC(=O)NH_2$, —$C(=NH)O(C_{1-6}$ alkyl$)$, —$OC(=NH)(C_{1-6}$ alkyl$)$, —$OC(=NH)OC_{1-6}$ alkyl, —$C(=NH)N(C_{1-6}$ alkyl$)_2$, —$C(=NH)NH(C_{1-6}$ alkyl$)$, —$C(=NH)NH_2$, —$OC(=NH)N(C_{1-6}$ alkyl$)_2$, —$OC(NH)NH(C_{1-6}$ alkyl$)$, —$OC(NH)NH_2$, —$NHC(NH)N(C_{1-6}$ alkyl$)_2$, —$NHC(=NH)NH_2$, —$NHSO_2 (C_{1-6}$ alkyl$)$, —$SO_2N(C_{1-6}$ alkyl$)_2$, —$SO_2NH(C_{1-6}$ alkyl$)$, —$SO_2NH_2$, —$SO_2C_{1-6}$ alkyl, —$SO_2OC_{1-6}$ alkyl, —$OSO_2C_{1-6}$ alkyl, —$SOC_{1-6}$ alkyl, —$Si(C_{1-6}$ alkyl$)_3$, —$OSi(C_{1-6}$ alkyl$)_3$-$C(=S)N(C_{1-6}$ alkyl$)$, $C(=S)NH(C_{1-6}$ alkyl$)$, $C(=S)NH_2$, —$C(=O)S(C_{1-6}$ alkyl$)$, —$C(=S)SC_{1-6}$ alkyl, —$SC(=S)SC_{1-6}$ alkyl, —$P(=O)_2(C_{1-6}$ alkyl$)$, —$P(=O)(C_{1-6}$ alkyl$)_2$, —$OP(=O)(C_{1-6}$ alkyl$)_2$, —$OP(=O)(OC_{1-6}$ alkyl$)_2$, $C_{1-6}$ alkyl, $C_{1-6}$ perhaloalkyl, $C_{2-6}$ alkenyl, $C_{2-6}$ alkynyl, $C_{3-10}$ carbocyclyl, $C_{6-10}$ aryl, 3-10 membered heterocyclyl, 5-10 membered heteroaryl; or two geminal $R^{gg}$ substituents can be joined to form =O or =S; wherein $X^-$ is a counterion.

A "counterion" or "anionic counterion" is a negatively charged group associated with a cationic quaternary amino group in order to maintain electronic neutrality. Exemplary counterions include halide ions (e.g., $F^-$, $Cl^-$, $Br^-$, $I^-$), $NO_3^-$, $ClO_4^-$, $OH^-$, $H_2PO_4^-$, $HSO_4^-$, sulfonate ions (e.g., methansulfonate, trifluoromethanesulfonate, p-toluenesulfonate, benzenesulfonate, 10-camphor sulfonate, naphthalene-2-sulfonate, naphthalene-1-sulfonic acid-5-sulfonate, ethan-1-sulfonic acid-2-sulfonate, and the like), and carboxylate ions (e.g., acetate, ethanoate, propanoate, benzoate, glycerate, lactate, tartrate, glycolate, succinate, maleate, fumarate, and the like).

"Halo" or "halogen" refers to fluorine (fluoro, —F), chlorine (chloro, —Cl), bromine (bromo, —Br), or iodine (iodo, —I).

As used herein, the term "unsubstituted hydroxyl" or "unsubstituted hydroxy" refers to the group —OH. The term "substituted hydroxyl" or "substituted hydroxyl," by extension, refers to a hydroxyl group wherein the oxygen atom directly attached to the parent molecule is substituted with a group other than hydrogen and includes groups selected from —$OR^{aa}$, —$ON(R^{bb})_2$, —$OC(=O)SR^{aa}$, —$OC(=O)R^{aa}$, —$OCO_2R^{aa}$, —$OC(=O)N(R^{bb})_2$, —$OC(=NR^{bb})R^{aa}$, —$OC(=NR^{bb})OR^{aa}$, —$OC(=NR^{bb})N(R^{bb})_2$, —$OS(=O)R^{aa}$, —$OSO_2R^{aa}$, —$OSi(R^{aa})_3$, —$OP(R^{cc})_2$, —$OP(R^{cc})_3$, —$OP(=O)_2R^{aa}$, —$OP(=O)(R^{aa})_2$, —$OP(=O)(OR^{cc})_2$, —$OP(=O)_2N(R^{bb})_2$, and —$OP(=O)(NR^{bb})_2$, wherein $R^{aa}$, $R^{bb}$, and $R^{cc}$ are as defined herein.

As used herein, the term "unsubstituted thiol" or "unsubstituted thio" refers to the group —SH. The term "substituted thiol" or "substituted thio," by extension, refers to a thiol group wherein the sulfur atom directly attached to the parent molecule is substituted with a group other than hydrogen, and includes groups selected from —$SR^{aa}$, —$S=SR^{cc}$, —$SC(=S)SR^{aa}$, —$SC(=O)SR^{aa}$, —$SC(=O)R^{aa}$, and —$SC(=O)R^{aa}$, wherein $R^{aa}$ and $R^{cc}$ are as defined herein.

As used herein, the term "unsubstituted amino" or "amino" refers to the group —$NH_2$. The term "substituted amino," by extension, refers to a monosubstituted, disubstituted, or trisubstituted amino group.

As used herein, the term "monosubstituted amino" refers to an amino group wherein the nitrogen atom directly attached to the parent molecule is substituted with one hydrogen and one group other than hydrogen. Exemplary monosubstituted amino groups include, but are not limited to, —$NH(R^{bb})$, —$NHC(=O)R^{aa}$, —$NHCO_2R^{aa}$, —$NHC(=O)N(R^{bb})_2$, —$NHC(=NR^{bb})N(R^{bb})_2$, —$NHSO_2R^{aa}$, —$NHP(=O)(OR^{cc})_2$, and —$NHP(=O)(NR^{bb})_2$, wherein $R^{aa}$, $R^{bb}$ and $R^{cc}$ are as defined herein, and wherein $R^{bb}$ of the group —NH($R^{bb}$) is not hydrogen.

As used herein, the term "disubstituted amino" refers to an amino group wherein the nitrogen atom directly attached to the parent molecule is substituted with two groups other than hydrogen. Exemplary disubstituted amino groups include, but are not limited to, —$N(R^{bb})_2$, —$NR^{bb}C(=O)R^{aa}$, —$NR^{bb}CO_2R^{aa}$, —$NR^{bb}C(=O)N(R^{bb})_2$, —$NR^{bb}C(=NR^{bb})N(R^{bb})_2$, —$NR^{bb}SO_2R^{aa}$, —$NR^{bb}P(=O)(OR^{cc})_2$, and —$NR^{bb}P(=O)(NR^{bb})_2$, wherein $R^{aa}$, $R^{bb}$, and $R^{cc}$ are as defined herein, with the proviso that the nitrogen atom directly attached to the parent molecule is not substituted with hydrogen.

As used herein, the term "trisubstituted amino" refers to an amino group wherein the nitrogen atom directly attached to the parent molecule is substituted with three groups. Exemplary trisubstituted amino groups include, but are not limited to, —$N(R^{bb})_3$ and —$N(R^{bb})_3^+X^-$, wherein $R^{bb}$ and $X^-$ are as defined herein, with the proviso that $R^{bb}$ is not H.

Nitrogen atoms can be substituted or unsubstituted as valency permits, and include primary, secondary, tertiary, and quarternary nitrogen atoms. Exemplary nitrogen atom substitutents include, but are not limited to, hydrogen, —OH, —$OR^{aa}$, —$N(R^{cc})_2$, —CN, —$C(=O)R^{aa}$, —$C(=O)N(R^{cc})_2$, —$CO_2R^{aa}$, —$SO_2R^{aa}$, —$C(=NR^{bb})R^{aa}$, —$C(=NR^{cc})OR^{aa}$, —$C(=NR^{cc})N(R^{cc})_2$, —$SO_2N(R^{cc})_2$, —$SO_2R^{cc}$, —$SO_2OR^{cc}$, —$SOR^{aa}$, —$C(=S)N(R^{cc})_2$, —$C(=O)SR^{cc}$, —$C(=S)SR^{cc}$, —$P(=O)_2R^{aa}$, —$P(=O)(R^{aa})_2$, —$P(=O)_2N(R^{cc})_2$, —$P(=O)(NR^{cc})_2$, $C_{1-10}$ alkyl, $C_{1-10}$ perhaloalkyl, $C_{2-10}$ alkenyl, $C_{2-10}$ alkynyl, $C_{3-10}$ carbocyclyl, 3-14 membered heterocyclyl, $C_{6-14}$ aryl, and 5-14 membered heteroaryl, or two $R^{cc}$ groups attached to a nitrogen atom are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 $R^{dd}$ groups, and wherein $R^{aa}$, $R^{bb}$, $R^{cc}$ and $R^{dd}$ are as defined herein.

The term "protecting group" as used herein, refers to a chemical modification of a functional group of a compound that prevents the functional group to take part in an undesired chemical reaction. Protecting groups play an important role in multi-step organic compound synthesis, and suitable protecting groups for various functional groups and chemical environments are well known in the art. Examples of protecting groups are nitrogen protecting groups, oxygen protecting groups, sulfur protecting groups, and carboxylic acid protecting groups are described in more detail herein.

In certain embodiments, the substituent present on a nitrogen atom is a nitrogen protecting group (also referred to as an amino protecting group). Nitrogen protecting groups include, but are not limited to, —OH, —OR$^{aa}$, —N(R$^{cc}$)$_2$, —C(=O) R$^{aa}$, —C(=O)N(R$^{cc}$)$_2$, —CO$_2$R$^{aa}$, —SO$_2$R$^{aa}$, —C(=NR$^{cc}$) R$^{aa}$, —C(=NR$^{cc}$)OR$^{aa}$, —C(=NR$^{cc}$)N(R$^{cc}$)$_2$, —SO$_2$N (R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, C$_{1-10}$ alkyl (e.g., aralkyl, heteroaralkyl), C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl groups, wherein each alkyl, alkenyl, alkynyl, carbocyclyl, heterocyclyl, aralkyl, aryl, and heteroaryl is independently substituted with 0, 1, 2, 3, 4, or 5 $R^{dd}$ groups, and wherein $R^{aa}$, $R^{bb}$, $R^{cc}$, and $R^{dd}$ are as defined herein. Nitrogen protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference.

Exemplary amide nitrogen protecting groups (e.g., —C(=O)R$^{aa}$) include, but are not limited to, formamide, acetamide, chloroacetamide, trichloroacetamide, trifluoroacetamide, phenylacetamide, 3-phenylpropanamide, picolinamide, 3-N-benzoylphenylalanyl derivative, benzamide, p-phenylbenzamide, o-nitrophenylacetamide, o-nitrophenoxyacetamide, acetoacetamide, (N'-dithiobenzyloxyacylamino)acetamide, 3-(p-hydroxyphenyl)propanamide, 3-(o nitrophenyl)propanamide, 2-methyl-2-(o-nitrophenoxy)propanamide, 2-methyl-2-(o phenylazophenoxy)propanamide, 4-chlorobutanamide, 3-methyl-3-nitrobutanamide, o-nitrocinnamide, N-acetylmethionine, o-nitrobenzamide, and o-(benzoyloxymethyl)benzamide.

Exemplary carbamate nitrogen protecting groups (e.g., —C(=O)R$^{aa}$) include, but are not limited to, methyl carbamate, ethyl carbamante, 9-fluorenylmethyl carbamate (Fmoc), 9-(2-sulfo)fluorenylmethyl carbamate, 9-(2,7-dibromo)fluoroenylmethyl carbamate, 2,7-di-t-butyl-[9-(10,10-dioxo-10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1 carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl)ethyl carbamate (Pyoc), 2-(N,N-dicyclohexylcarboxamido)ethyl carbamate, t-butyl carbamate (BOC), 1-carbamate (Adoc), vinyl carbamate (Voc), allyl carbamate (Alloc), 1-carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitrobenzyl carbamate, p-bromobenzyl carbamate, p-chlorobenzyl carbamate, 2,4-dichlorobenzyl carbamate, 4-carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianyl)]methyl carbamate (Dmoc), 4-carbamate (Mtpc), 2,4-dimethylthiophenyl carbamate (Bmpc), 2-carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl)methyl carbamate, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxyacylvinyl carbamate, o-(N,N-dimethylcarboxamido)benzyl carbamate, 1,1-dimethyl-3-(N,N-dimethylcarboxamido)propyl carbamate, 1,1-dimethylpropynyl carbamate, di(2-pyridyl)methyl carbamate, 2-furanylmethyl carbamate, 2-iodoethyl carbamate, isobornyl carbamate, isobutyl carbamate, isonicotinyl carbamate, p-(p'-methoxyphenylazo)benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl)ethyl carbamate, phenyl carbamate, p-(phenylazo)benzyl carbamate, 2,4,6-tri-t-butylphenyl carbamate, 4-(trimethylammonium)benzyl carbamate, and 2,4,6-trimethylbenzyl carbamate.

Exemplary sulfonamide nitrogen protecting groups (e.g., —S(=O)$_2$R$^{aa}$) include, but are not limited to, p-toluenesulfonamide (Ts), benzenesulfonamide, 2,3,6,-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), β-trimethylsilylethanesulfonamide (SES), 9-anthracenesulfonamide, 4-(4',8'-dimethoxynaphthylmethyl)benzenesulfonamide (DNMBS), benzylsulfonamide, trifluoromethylsulfonamide, and phenacylsulfonamide.

Other exemplary nitrogen protecting groups include, but are not limited to, phenothiazinyl-(10)-acyl derivative, N'-p-toluenesulfonylaminoacyl derivative, N'-phenylaminothioacyl derivative, N-benzoylphenylalanyl derivative, N-acetylmethionine derivative, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethylsilyl)ethoxy]methylamine (SEM), N-3-acetoxypropylamine, N-(1-isopropyl-4-nitro-2-oxo-3-pyroolin-3-yl)amine, quaternary ammonium salts, N-benzylamine, N-di(4-methoxyphenyl)methylamine, N-5-dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9- fluorenylmethyleneamine, N-ferrocenylmethylamino (Fcm), N-2-picolylamino N'-oxide, N-1,1-dimethylthiomethyleneamine, N-benzylideneamine, N-p-methoxybenzylideneamine, N-diphenylmethyleneamine, N-[(2-pyridyl)mesityl]methyleneamine, N—(N',N'-dimethylaminomethylene)amine, N,N'-isopropylidenediamine, N-p-nitrobenzylideneamine, N-salicylideneamine, N-5-chlorosalicylideneamine, N-(5-chloro-2-hydroxyphenyl)phenylmethyleneamine, N-cyclohexylideneamine, N-(5,5-dimethyl-3-oxo-1-cyclohexenyl)amine, N-borane derivative, N-diphenylborinic acid derivative, N-[phenyl(pentaacylchromium- or tungsten)acyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, and 3-nitropyridinesulfenamide (Npys).

In certain embodiments, the substituent present on an oxygen atom is an oxygen protecting group (also referred to as a hydroxyl protecting group). Oxygen protecting groups include, but are not limited to, —R$^{aa}$, —N(R$^{bb}$)$_2$, —C(=O)SR$^{aa}$, —C(=O)R$^{aa}$, —CO$_2$R$^{aa}$, —C(=O)N(R$^{bb}$)$_2$, —C(=NR$^{bb}$)R$^{aa}$, —C(=NR$^{bb}$)OR$^{aa}$, —C(=NR$^{bb}$)N(R$^{bb}$)$_2$, —S(=O)R$^{aa}$, —SO$_2$R$^{aa}$, —Si(R$^{aa}$)$_3$, —P(R$^{cc}$)$_2$, —P(R$^{cc}$)$_3$, —P(=O)$_2$R$^{aa}$, —P(=O)(R$^{aa}$)$_2$, —P(=O)(OR$^{cc}$)$_2$, —P(=O)$_2$N(R$^{bb}$)$_2$, and —P(=O)(NR$^{bb}$)$_2$, wherein R$^{aa}$, R$^{bb}$, and R$^{CC}$ are as defined herein. Oxygen protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference.

Exemplary oxygen protecting groups include, but are not limited to, methyl, methoxylmethyl (MOM), methylthiomethyl (MTM), t-butylthiomethyl, (phenyldimethylsilyl)methoxymethyl (SMOM), benzyloxymethyl (BOM), p-methoxybenzyloxymethyl (PMBM), (4-methoxyphenoxy)methyl (p-AOM), guaiacolmethyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethylsilyl)ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxide, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, benzyl (Bn), p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxido, diphenylmethyl, p,p'-dinitrobenzhydryl, 5-dibenzosuberyl, triphenylmethyl, a-naphthyldiphenylmethyl, p-methoxyphenyldiphenylmethyl, di(p-methoxyphenyl)phenylmethyl, tri(p-methoxyphenyl)methyl, 4-(4'-bromophenacyloxyphenyl)diphenylmethyl, 4,4',4''-tris(4,5-dichlorophthalimidophenyl)methyl, 4,4',4''-tris(levulinoyloxyphenyl)methyl, 4,4',4''-tris(benzoyloxyphenyl)methyl, 3-(imidazol-1-yl)bis(4',4''-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodisulfuran-2-yl, benzisothiazolyl S,S-dioxido, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS), tribenzylsilyl, tri-p-xylylsilyl, triphenylsilyl, diphenylmethylsilyl (DPMS), t-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate (mesitoate), alkyl methyl carbonate, 9-fluorenylmethyl carbonate (Fmoc), alkyl ethyl carbonate, alkyl 2,2,2-trichloroethyl carbonate (Troc), 2-(trimethylsilyl)ethyl carbonate (TMSEC), 2-(phenylsulfonyl) ethyl carbonate (Psec), 2-(triphenylphosphonio) ethyl carbonate (Peoc), alkyl isobutyl carbonate, alkyl vinyl carbonate alkyl allyl carbonate, alkyl p-nitrophenyl carbonate, alkyl benzyl carbonate, alkyl p-methoxybenzyl carbonate, alkyl 3,4-dimethoxybenzyl carbonate, alkyl o-nitrobenzyl carbonate, alkyl p-nitrobenzyl carbonate, alkyl S-benzyl thiocarbonate, 4-ethoxy-1-napthtyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy)ethyl, 4-(methylthiomethoxy)butyrate, 2-(methylthiomethoxymethyl)benzoate, 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate, o-(methoxyacyl)benzoate, a-naphthoate, nitrate, alkyl N,N,N',N'-tetramethylphosphorodiamidate, alkyl N-phenylcarbamate, borate, dimethylphosphinothioyl, alkyl 2,4-dinitrophenylsulfenate, sulfate, methanesulfonate (mesylate), benzylsulfonate, brosylate, and tosylate (Ts).

In certain embodiments, the substituent present on a sulfur atom is a sulfur protecting group (also referred to as a thiol protecting group). Sulfur protecting groups include, but are not limited to, —R$^{aa}$, —N(R$^{bb}$)$_2$, —C(=O)SR$^{aa}$, —C(=O)R$^{aa}$, —CO$_2$R$^{aa}$, —C(=O)N(R$^{bb}$)$_2$, —C(=NR$^{bb}$)R$^{aa}$, —C(=NR$^{bb}$)OR$^{aa}$, —C(=NR$^{bb}$)N(R$^{bb}$)$_2$, —S(=O)R$^{aa}$, —SO$_2$R$^{aa}$, —Si(R$^{aa}$)$_3$, —P(R$^{cc}$)$_2$, —P(R$^{cc}$)$_3$, —P(=O)$_2$R$^{aa}$, —P(=O)(R$^{aa}$)$_2$, —P(=O)(OR$^{cc}$)$_2$, —P(=O)$_2$N(R$^{bb}$)$_2$, and —P(=O)(NR$^{bb}$)$_2$, wherein R$^{aa}$, R$^{bb}$, and R$^{CC}$ are as defined herein. Sulfur protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference.

A "carboxylic acid protecting group" or "protected carboxylic acid," as used herein, are well known in the art and include those described in detail in Greene (1999). Examples of protected carboxylic acids further include, but are not limited to, silyl-, alkyl-, alkenyl-, aryl-, and arylalkyl-protected carboxylic acids. Examples of suitable silyl groups include trimethylsilyl, triethylsilyl, t-butyldimethylsilyl, t-butyldiphenylsilyl, triisopropylsilyl, and the like. Examples of suitable alkyl groups include methyl, benzyl, p-methoxybenzyl, 3,4-dimethoxybenzyl, trityl, t-butyl, tetrahydropyran-2-yl. Examples of suitable alkenyl groups include allyl. Examples of suitable aryl groups include optionally substituted phenyl, biphenyl, or naphthyl. Examples of suitable arylalkyl groups include optionally substituted benzyl (e.g., p-methoxybenzyl (MPM), 3,4-dimethoxybenzyl, O-nitrobenzyl, p-nitrobenzyl, p-halobenzyl, 2,6-dichlorobenzyl, p-cyanobenzyl), and 2- and 4-picolyl.

These and other exemplary substituents and protecting groups are described in more detail in the Detailed Description, Examples, Figures, and Claims. The invention is not intended to be limited in any manner by the above exemplary listing of substituents and protecting groups.

OTHER DEFINITIONS

As used herein, the term "pharmaceutically acceptable salt" refers to those salts which are, within the scope of sound medical judgment, suitable for use in humans and other animals without undue toxicity, irritation, immunological response, and are commensurate with a reasonable benefit/risk ratio. Pharmaceutically acceptable salts are well known in the art. For example, Berge et al. describe pharmaceutically acceptable salts in detail in *J. Pharmaceutical Sciences*, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate, and the like. Salts derived from appropriate bases include alkali metal, alkaline earth metal, ammonium and $N^+(C_{1-4}alkyl)_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate, and aryl sulfonate.

A "subject" to which administration is contemplated includes, but is not limited to, humans (i.e., a male or female of any age group, e.g., a pediatric subject (e.g, infant, child, adolescent) or adult subject (e.g., young adult, middle-aged adult, or senior adult)) and/or other non-human animals, for example, mammals (e.g., primates (e.g., cynomolgus monkeys, rhesus monkeys); commercially relevant mammals such as cattle, pigs, horses, sheep, goats, cats, and/or dogs), birds (e.g., commercially relevant birds such as chickens, ducks, geese, and/or turkeys), reptiles, amphibians, and fish. In certain embodiments, the non-human animal is a mammal. The non-human animal may be a male or female at any stage of development. A non-human animal may be a transgenic animal.

The terms "administer," "administering," or "administration," as used herein, refer to implanting, absorbing, ingesting, injecting, or inhaling a substance, for example, a compound or composition as described herein.

As used herein the term "inhibit" or "inhibition" in the context of enzymes, for example, in the context of IDE, refers to a reduction in the activity of the enzyme. In some embodiments, the term refers to a reduction of the level of enzyme activity, e.g., IDE activity, to a level that is statistically significantly lower than an initial level, which may, for example, be a baseline level of enzyme activity. In some embodiments, the term refers to a reduction of the level of enzyme activity, e.g., IDE activity, to a level that is less than 75%, less than 50%, less than 40%, less than 30%, less than 25%, less than 20%, less than 10%, less than 9%, less than 8%, less than 7%, less than 6%, less than 5%, less than 4%, less than 3%, less than 2%, less than 1%, less than 0.5%, less than 0.1%, less than 0.01%, less than 0.001%, or less than 0.0001% of an initial level, which may, for example, be a baseline level of enzyme activity.

As used herein, the term "insulin degrading enzyme" or "IDE" refers to an insulin-degrading enzyme. IDE enzymes (also referred to herein as IDE proteins) and their respective encoding RNA and DNA sequences according to some aspects of this invention include human IDE protein and encoding sequences, as well as, in some embodiments, IDE proteins and encoding sequences from other species, for example, from other mammals (e.g., IDE proteins and encoding sequences from mouse, rat, cat, dog, cattle, goat, sheep, pig, or primate), from other vertebrates, and from insects. In some embodiments, an IDE inhibitor provided herein is specific for an IDE from a species, e.g., for human IDE, mouse IDE, rat IDE, and so on. In some embodiment, an IDE provided herein inhibits IDEs from more than one species, e.g., human IDE and mouse IDE. In some embodiments, an IDE provided herein exhibits equipotent inhibition of IDEs from more than one species, e.g., equipotent inhibition of human and mouse IDEs. The term IDE further includes, in some embodiments, sequence variants and mutations (e.g., naturally occurring or synthetic IDE sequence variants or mutations), and different IDE isoforms. In some embodiments, the term IDE includes protein or encoding sequences that are homologous to an IDE protein or encoding sequence, for example, a protein or encoding sequence having at least 80%, at least 85%, at least 90%, at least 91%, at least 92%, at least 93%, at least 94%, at least 95%, at least 96%, at least 97%, at least 98%, at least 99%, or at least 99.5% sequence identity with an IDE sequence, for example, with an IDE sequence provided herein. In some embodiments, the term IDE refers to a protein exhibiting IDE activity, for example, a protein exhibiting insulin-targeted protease activity, or a nucleic acid sequence encoding such a protein. In some embodiments, the term IDE included proteins that exhibit at least 50%, at least 60%, at least 70%, at least 80%, at least 90%, at least 95%, or at least 100% insulin-targeting protease activity as compared to a known IDE protein or encoding sequence, for example, as compared to an IDE sequence provided herein. IDE protein and encoding gene sequences are well known to those of skill in the art, and exemplary protein sequences include, but are not limited to, the following sequences. Additional IDE sequences will be apparent to those of skill in the art, and the invention is not limited to the exemplary sequences provided herein.

>gi|155969707|ref|NP_004960.2|insulin-degrading enzyme isoform 1 [Homo sapiens]

(SEQ ID NO: 1)

MRYRLAWLLHPALPSTFRSVLGARLPPPERLCGFQKKTYSKMNNPAIKRIGNHITKSP

EDKREYRGLELANGIKVLLISDPTTDKSSAALDVHIGSLSDPPNIAGLSHFCEHMLFLG

TKKYPKENEYSQFLSEHAGSSNAFTSGEHTNYYFDVSHEHLEGALDRFAQFFLCPLF

DESCKDREVNAVDSEHEKNVMNDAWRLFQLEKATGNPKHPFSKFGTGNKYTLETR

PNQEGIDVRQELLKFHSAYYSSNLMAVCVLGRESLDDLTNLVVKLFSEVENKNVPLP

EFPEHPFQEEHLKQLYKIVPIKDIRNLYVTFPIPDLQKYYKSNPGHYLGHLIGHEGPGS

LLSELKSKGWVNTLVGGQKEGARGFMFFIINVDLTEEGLLHVEDIILHMFQYIQKLRA

EGPQEWVFQECKDLNAVAFRFKDKERPRGYTSKIAGILHYYPLEEVLTAEYLLEEFR

PDLIEMVLDKLRPENVRVAIVSKSFEGKTDRTEEWYGTQYKQEAIPDEVIKKWQNAD

LNGKFKLPTKNEFIPTNFEILPLEKEATPYPALIKDTAMSKLWFKQDDKFFLPKACLN

FEFFSPFAYVDPLHCNMAYLYELLKDSLNEYAYAAELAGLSYDLQNTIYGMYLSV

KGYNDKQPILLKKIIEKMATFEIDEKRFEIIKEAYMRSLNNFRAEQPHQHAMYYLRLL

MTEVAWTKDELKEALDDVTLPRLKAFIPQLLSRLHIEALLHGNITKQAALGIMQMVE

DTLIEHAHTKPLLPSQLVRYREVQLPDRGWFVYQQRNEVHNNCGIEIYYQTDMQSTS

ENMFLELFCQIISEPCFNTLRTKEQLGYIVFSGPRRANGIQGLRFIIQSEKPPHYLESRV

EAFLITMEKSIEDMTEEAFQKHIQALAIRRLDKPKKLSAECAKYWGEIISQQYNFDRD

NTEVAYLKTLTKEDIIKFYKEMLAVDAPRRHKVSVHVLAREMDSCPVVGEFPCQNDI

NLSQAPALPQPEVIQNMTEFKRGLPLFPLVKPHINFMAAKL

>gi|260099676|ref|NP_001159418.1|insulin-degrading enzyme isoform 2 [Homo sapiens]

(SEQ ID NO: 2)

MSKLWFKQDDKFFLPKACLNFEFFSPFAYVDPLHCNMAYLYELLKDSLNEYAYAA

ELAGLSYDLQNTIYGMYLSVKGYNDKQPILLKKIIEKMATFEIDEKRFEIIKEAYMRSL

NNFRAEQPHQHAMYYLRLLMTEVAWTKDELKEALDDVTLPRLKAFIPQLLSRLHIE

ALLHGNITKQAALGIMQMVEDTLIEHAHTKPLLPSQLVRYREVQLPDRGWFVYQQR

NEVHNNCGIEIYYQTDMQSTSENMFLELFCQIISEPCFNTLRTKEQLGYIVFSGPRRAN

GIQGLRFIIQSEKPPHYLESRVEAFLITMEKSIEDMTEEAFQKHIQALAIRRLDKPKKLS

AECAKYWGEIISQQYNFDRDNTEVAYLKTLTKEDIIKFYKEMLAVDAPRRHKVSVH

VLAREMDSCPVVGEFPCQNDINLSQAPALPQPEVIQNMTEFKRGLPLFPLVKPHINFM

AAKL

>gi|121583922|ref|NP_112419.2|insulin-degrading enzyme [Mus musculus]

(SEQ ID NO: 3)

MRNGLVWLLHPALPGTLRSILGARPPPAKRLCGFPKQTYSTMSNPAIQRIEDQIVKSP

EDKREYRGLELANGIKVLLISDPTTDKSSAALDVHIGSLSDPPNIPGLSHFCEHMLFLG

TKKYPKENEYSQFLSEHAGSSNAFTSGEHTNYYFDVSHEHLEGALDRFAQFFLCPLF

DASCKDREVNAVDSEHEKNVMNDAWRLFQLEKATGNPKHPFSKFGTGNKYTLETR

PNQEGIDVREELLKFHSTYYSSNLMAICVLGRESLDDLTNLVVKLFSEVENKNVPLPE

FPEHPFQEEHLRQLYKIVPIKDIRNLYVTFPIPDLQQYYKSNPGHYLGHLIGHEGPGSL

LSELKSKGWVNTLVGGQKEGARGFMFFIINVDLTEEGLLHVEDIILHMFQYIQKLRAE

GPQEWVFQECKDLNAVAFRFKDKERPRGYTSKIAGKLHYYPLNGVLTAEYLLEEFR

PDLIDMVLDKLRPENVRVAIVSKSFEGKTDRTEQWYGTQYKQEAIPEDIIQKWQNAD

-continued
```
LNGKFKLPTKNEFIPTNFEILSLEKDATPYPALIKDTAMSKLWFKQDDKFFLPKACLN

FEFFSPFAYVDPLHCNMAYLYLELLKDSLNEYAYAAELAGLSYDLQNTIYGMYLSV

KGYNDKQPILLKKITEKMATFEIDKKRFEIIKEAYMRSLNNFRAEQPHQHAMYYLRL

LMTEVAWTKDELKEALDDVTLPRLKAFIPQLLSRLHIEALLHGNITKQAALGVMQM

VEDTLIEHAHTKPLLPSQLVRYREVQLPDRGWFVYQQRNEVHNNCGIEIYYQTDMQ

STSENMFLELFCQIISEPCFNTLRTKEQLGYIVFSGPRRANGIQGLRFIIQSEKPPHYLES

RVEAFLITMEKAIEDMTEEAFQKHIQALAIRRLDKPKKLSAECAKYWGEIISQQYNYD

RDNIEVAYLKTLTKDDIIRFYQEMLAVDAPRRHKVSVHVLAREMDSCPVVGEFPSQN

DINLSEAPPLPQPEVIHNMTEFKRGLPLFPLVKPHINFMAAKL
```

As used herein, the terms "treatment," "treat," and "treating" refer to a clinical intervention aimed to reverse, alleviate, delay the onset of, or inhibit the progress of a disease or disorder, or one or more symptoms thereof, as described herein. As used herein, the terms "treatment," "treat," and "treating" refer to a clinical intervention aimed to reverse, alleviate, delay the onset of, or inhibit the progress of a disease or disorder, or one or more symptoms thereof, as described herein. In some embodiments, treatment may be administered after one or more symptoms have developed and/or after a disease has been diagnosed. In other embodiments, treatment may be administered in the absence of symptoms. For example, treatment may be administered to a susceptible individual prior to the onset of symptoms (e.g., in light of a history of symptoms and/or in light of genetic or other susceptibility factors). Treatment may also be continued after symptoms have resolved, for example to prevent or delay their recurrence. In some embodiments, the disease or disorder being treated is associated with aberrant IDE activity, or can be treated by inhibiting IDE activity. In some embodiments, the disease is metabolic syndrome or diabetes. In some embodiments, the disease is diabetes or metabolic syndrome in a subject with Alzheimer's Disease or at risk of developing Alzheimer's Disease.

The terms "effective amount" and "therapeutically effective amount," as used herein, refer to the amount or concentration of an inventive compound, that, when administered to a subject, is effective to at least partially treat a condition from which the subject is suffering. In some embodiments, an effective amount of an IDE inhibitor is an amount the administration of which results in inhibition of at least about 50%, at least about 60%, at least about 70%, at least about 75%, at least about 80%, at least about 90%, at least about 95%, at least about 98%, at least about 99%, at least about 99.5%, or about 100% of IDE activity as compared to a baseline level, for example, a level of IDE activity in the absence of the inhibitor.

DETAILED DESCRIPTION OF CERTAIN EMBODIMENTS OF THE INVENTION

Insulin-degrading enzyme (IDE) is a widely expressed, secreted 110 kDa zinc-metalloprotease that degrades pathophysiologically relevant peptides such as insulin and amyloid beta-protein.[1,2] Despite long-standing interest in its pharmacological inhibition since IDE was discovered in 1949,[3] IDE has remained an elusive target for pharmacological modulation. IDE is insensitive to most hydroxamate-based small molecules that have seen widespread use as zinc-metalloproteinase inhibitors,[4] presumably due to the unique structure of IDE's active site.[5]

As described in international PCT application, PCT/US2011/045966, entitled "Macrocyclic kinase inhibitors and uses thereof," filed Jul. 29, 2011; and Kleiner et al., "In Vitro Selection of a DNA-Templated Macrocycle Library Reveals a Class of Macrocyclic Kinase Inhibitors." J. Am. Chem. Soc. 132, 11779-11791 (2010), the entire contents of each of which are incorporated herein by reference, bioactive small molecules can be efficiently identified from DNA-encoded small molecule libraries by in vitro selection. Here, we report the discovery of potent inhibitors ($IC_{50} < 1$ μM) of IDE from a macrocycle library. The macrocycles described herein constitute some of the first potent and selective inhibitors of IDE and may serve as powerful tools for probing IDE biology and for treating diseases, disorders, and conditions associated with aberrant IDE activity or that can be treated or ameliorated by inhibiting IDE activity, for example, metabolic syndrome or diabetes. The pharmacological properties of the macrocyclic IDE inhibitors provided herein allow for their use in patients suffering from an IDE-associated diseases, disorder, or condition (e.g., from diabetes or metabolic syndrome), and also from Alzheimer's Disease.

Macrocyclic IDE Inhibitors

In one aspect, the present invention provides macrocyclic IDE inhibitors. The IDE inhibitors described herein are typically of the Formula (I):

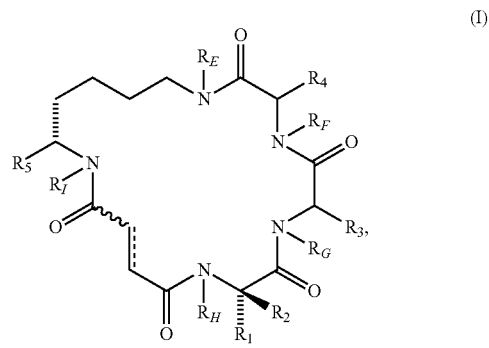

(I)

or pharmaceutically acceptable salts, solvates, hydrates, stereoisomers, polymorphs, tautomers, isotopically enriched forms, and prodrugs thereof, wherein:

------ is a single or double C—C bond, wherein when ------ is a double C—C bond, then ⌇⌇⌇ indicates that the adjacent C—C double bond is in a cis or trans configuration;

$R_1$ is hydrogen; halogen; substituted or unsubstituted aliphatic; substituted or unsubstituted heteroaliphatic; substituted or unsubstituted aryl; substituted or unsubstituted heteroaryl; substituted or unsubstituted acyl; —OR$_A$; —N(R$_A$)$_2$; —SR$_A$; =O; —CN; —NO$_2$; —SCN; —SOR$_A$; or —SO$_2$R$_A$; wherein each occurrence of R$_A$ is independently hydrogen; a protecting group; substituted or unsubstituted aliphatic; substituted or unsubstituted heteroaliphatic; substituted or unsubstituted acyl; substituted or unsubstituted aryl; or substituted or unsubstituted heteroaryl;

R$_2$ is hydrogen; halogen; substituted or unsubstituted aliphatic; substituted or unsubstituted heteroaliphatic; substituted or unsubstituted aryl; substituted or unsubstituted heteroaryl; substituted or unsubstituted acyl; —OR$_B$; —N(R$_B$)$_2$; —SR$_B$; =O; —CN; —NO$_2$; —SCN; —SOR$_B$; or —SO$_2$R$_B$; wherein each occurrence of R$_B$ independently hydrogen; a protecting group; substituted or unsubstituted aliphatic; substituted or unsubstituted heteroaliphatic; substituted or unsubstituted acyl; substituted or unsubstituted aryl; or substituted or unsubstituted heteroaryl;

R$_3$ is hydrogen; halogen; substituted or unsubstituted aliphatic; substituted or unsubstituted heteroaliphatic; substituted or unsubstituted aryl; substituted or unsubstituted heteroaryl; substituted or unsubstituted acyl; —OR$_C$; —N(R$_C$)$_y$; —SR$_C$; =O; —CN; —NO$_2$; —SCN; —SOR$_C$; or —SO$_2$R$_C$; wherein y is 0, or an integer between 1-2, inclusive, and wherein each occurrence of R$_C$ is independently hydrogen; a protecting group; substituted or unsubstituted aliphatic; substituted or unsubstituted heteroaliphatic; substituted or unsubstituted acyl; substituted or unsubstituted aryl; or substituted or unsubstituted heteroaryl;

R$_4$ is hydrogen; halogen; substituted or unsubstituted aliphatic; substituted or unsubstituted heteroaliphatic; substituted or unsubstituted aryl; substituted or unsubstituted heteroaryl; substituted or unsubstituted acyl; —OR$_C$; —N(R$_D$)$_y$; —SR$_D$; =O; —CN; —NO$_2$; —SCN; —SOR$_D$; or —SO$_2$R$_D$; wherein y is 0, or an integer between 1-2, inclusive, and wherein each occurrence of R$_D$ is independently hydrogen; a protecting group; substituted or unsubstituted aliphatic; substituted or unsubstituted heteroaliphatic; substituted or unsubstituted acyl; substituted or unsubstituted aryl; or substituted or unsubstituted heteroaryl R$_5$ is substituted or unsubstituted aliphatic; substituted or unsubstituted heteroaliphatic; substituted or unsubstituted aryl; substituted or unsubstituted heteroaryl; substituted or unsubstituted amino; —C(=O)—N(R$_J$)$_2$; —C(=O)—OR$_J$; or —C(=O)—SR$_J$, or CH$_2$—C(=O)N(R$_J$)$_2$, wherein each occurrence of R$_J$ is independently hydrogen; a protecting group; substituted or unsubstituted aliphatic; substituted or unsubstituted heteroaliphatic; substituted or unsubstituted acyl; substituted or unsubstituted aryl; or substituted or unsubstituted heteroaryl; or two R$_J$ groups are joined to form a substituted or unsubstituted heterocyclic group; optionally wherein R$_5$ further comprises a label, resin, or therapeutic agent attached thereto; and each instance of R$_E$, R$_F$, R$_G$, R$_H$, and R$_I$ is independently hydrogen; substituted or unsubstituted acyl; a nitrogen protecting group; substituted or unsubstituted aliphatic; substituted or unsubstituted heteroaliphatic; substituted or unsubstituted aryl; substituted or unsubstituted heteroaryl; substitute or unsubstituted hydroxyl; substituted or unsubstituted thiol; substituted or unsubstituted amino; or halogen; optionally wherein an R$_4$ group and R$_F$ are joined to form a substituted or unsubstituted heterocyclic ring; an R$_3$ group and R$_G$ are joined to form a substituted or unsubstituted heterocyclic ring; and/or R$_1$ or R$_2$ group and R$_H$ are joined to form a substituted or unsubstituted heterocyclic ring. In some embodiments, R$_E$, R$_F$, R$_G$, R$_H$, and R$_I$ are all H.

In some embodiments, the macrocyclic IDE inhibitors are of Formula (II):

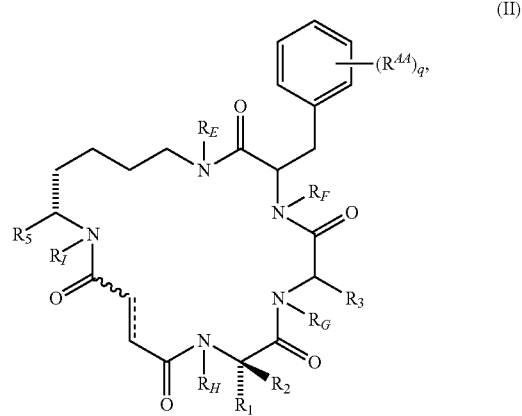

(II)

or pharmaceutically acceptable salts, solvates, hydrates, stereoisomers, polymorphs, tautomers, isotopically enriched forms, and prodrugs thereof, wherein:

q is 0 or an integer between 1 and 5, inclusive;

----- is a single or double C—C bond, wherein when ----- is a double C—C bond, then ∼∼∼ indicates that the adjacent C—C double bond is in a cis or trans configuration; and each instance of R$_1$, R$_2$, R$_3$, R$_6$, R$_E$, R$_F$, R$_G$, R$_H$, and R$_I$ are as defined in Formula (I);

each instance of R$^{AA}$ is independently halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —OR$^{A3}$, —N(R$^{A4}$)$_2$, —SR$^{A3}$, —C(=O)R$^{A3}$, —C(=O)OR$^{A3}$, —C(=O)SR$^{A3}$, —C(=O)N(R$^{A4}$)$_2$, —OC(=O)R$^{A3}$, —OC(=O)OR$^{A3}$, —OC(=O)SR$^{A3}$, —OC(=O)N(R$^{A4}$)$_2$, —NR$^{A4}$C(=O)R$^{A4}$, —NR$^{A4}$C(=O)OR$^{A3}$, —NR$^{A4}$C(=O)SR$^{A3}$, —NR$^{A4}$C(=O)N(R$^{A4}$)$_2$, —SC(=O)R$^{A3}$, —SC(=O)OR$^{A3}$, —SC(=O)SR$^{A3}$, —SC(=O)N(R$^{A4}$)$_2$, —C(=NR$^{A4}$)R$^{A3}$, —C(=NR$^{A4}$)OR$^{A3}$, —C(=NR$^{A4}$)SR$^{A3}$, —C(=NR$^{A4}$)N(R$^{A4}$)$_2$, —OC(=NR$^{A4}$)R$^{A3}$, —OC(=NR$^{A4}$)OR$^{A3}$, —OC(=NR$^{A4}$)SR$^{A3}$, —OC(=NR$^{A4}$)N(R$^{A4}$)$_2$, —NR$^{A4}$C(=NR$^{A4}$)R$^{A2}$, —NR$^{A4}$C(=NR$^{A4}$)OR$^{A3}$, —NR$^{A4}$C(=NR$^{A4}$)SR$^{A3}$, —NR$^{A4}$C(=NR$^{A4}$)N(R$^{A4}$)$_2$, —SC(=NR$^{A4}$)R$^{A3}$, —SC(=NR$^{A4}$)OR$^{A3}$, —SC(=NR$^{A4}$)SR$^{A3}$, —SC(=NR$^{A4}$)N(R$^{A4}$)$_2$, —C(=S)R$^{A3}$, —C(=S)OR$^{A3}$, —C(=S)SR$^{A3}$, —C(=S)N(R$^{A4}$)$_2$, —OC(=S)R$^{A3}$, —OC(=S)OR$^{A3}$, —OC(=S)SR$^{A3}$, —OC(=S)N(R$^{A4}$)$_2$, NR$^{A4}$C(=S)R$^{A4}$, —NR$^{A4}$C(=S)OR$^{A3}$, —NR$^{A4}$C(=S)SR$^{A3}$, —NR$^{A4}$C(=S)N(R$^{A4}$)$_2$, —SC(=S)R$^{A3}$ SC(=S)OR$^{A3}$, —SC(=S)SR$^{A3}$, —SC(=S)N(R$^{A4}$)$_2$, —S(=O)R$^{A3}$, —SO$_2$R$^{A3}$, —NR$^{A4}$SO$_2$R$^{A3}$, SO$_2$N(R$^{A4}$)$_2$, —N$_3$, —CN, —SCN, and —NO$_2$, wherein each occurrence of R$^{A3}$ is independently hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl; and each occurrence of R$^{A4}$ is independently hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, or a nitrogen protecting group, or two R$^{A4}$ groups are joined to form a substituted or unsubstituted heterocyclic ring.

In some embodiments, the macrocyclic IDE inhibitors are of Formula (III):

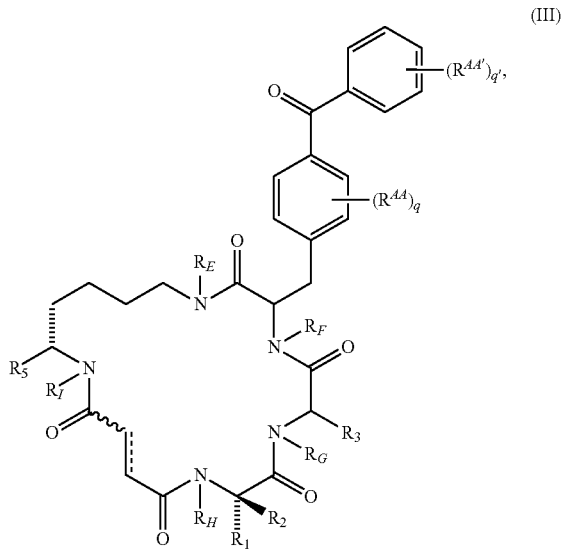

(III)

or pharmaceutically acceptable salts, solvates, hydrates, stereoisomers, polymorphs, tautomers, isotopically enriched forms, and prodrugs thereof,
wherein:
q is 0 or an integer between 1 and 5, inclusive;
q' is 0 or an integer between 1 and 5, inclusive;
------ is a single or double C—C bond, wherein when ------ is a double C—C bond, then ⁓ indicates that the adjacent C—C double bond is in the cis or trans configuration; and each instance of $R_1$, $R_2$, $R_3$, $R_5$, $R_E$, $R_F$, $R_G$, $R_H$, and $R_I$ are as defined in Formula (I);

each instance of $R^{A4}$ is independently halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —OR$^{A3}$, —N(R$^{A4}$)$_2$, —SR$^{A3}$, —C(=O)R$^{A3}$, —C(=O)OR$^{A3}$, —C(=O)SR$^{A3}$, —C(=O)N(R$^{A4}$)$_2$, —OC(=O)R$^{A3}$, —OC(=O)OR$^{A3}$, —OC(=O)SR$^{A3}$, —OC(=O)N(R$^{A4}$)$_2$, —NR$^{A4}$C(=O)R$^{A4}$, —NR$^{A4}$C(=O)OR$^{A3}$, —NR$^{A4}$C(=O)SR$^{A3}$, —NR$^{A4}$C(=O)N(R$^{A4}$)$_2$, —SC(=O)R$^{A3}$, —SC(=O)OR$^{A3}$, —SC(=O)SR$^{A3}$, —SC(=O)N(R$^{A4}$)$_2$, —C(=NR$^{A4}$)R$^{A3}$, —C(=NR$^{A4}$)OR$^{A3}$, —C(=NR$^{A4}$)SR$^{A3}$, —C(=NR$^{A4}$)N(R$^{A4}$)$_2$, —OC(=NR$^{A4}$)R$^{A3}$, —OC(=NR$^{A4}$)OR$^{A3}$, —OC(=NR$^{A4}$)SR$^{A3}$, —OC(=NR$^{A4}$)N(R$^{A4}$)$_2$, —NR$^{A4}$C(=NR$^{A4}$)R$^{A2}$, —NR$^{A4}$C(=NR$^{A4}$)OR$^{A3}$, —NR$^{A4}$C(=NR$^{A4}$)SR$^{A3}$, —NR$^{A4}$C(=NR$^{A4}$)N(R$^{A4}$)$_2$, —SC(=NR$^{A4}$)R$^{A3}$, —SC(=NR$^{A4}$)OR$^{A3}$, —SC(=NR$^{A4}$)SR$^{A3}$, —SC(=NR$^{A4}$)N(R$^{A4}$)$_2$, —C(=S)R$^{A3}$, —C(=S)OR$^{A3}$, —C(=S)SR$^{A3}$, —C(=S)N(R$^{A4}$)$_2$, —OC(=S)R$^{A3}$, —OC(=S)OR$^{A3}$, —OC(=S)SR$^{A3}$, —OC(=S)N(R$^{A4}$)$_2$, —NR$^{A4}$C(=S)R$^{A4}$, —NR$^{A4}$C(=S)OR$^{A3}$, —NR$^{A4}$C(=S)SR$^{A3}$, —NR$^{A4}$C(=S)N(R$^{A4}$)$_2$, —SC(=S)R$^{A3}$, —SC(=S)OR$^{A3}$, —SC(=S)SR$^{A3}$, —SC(=S)N(R$^{A4}$)$_2$, —S(=O)R$^{A3}$, —SO$_2$R$^{A3}$, —NR$^{A4}$ SO$_2$R$^{A3}$, —SO$_2$N(R$^{A4}$)$_2$, —N$_3$, —CN, —SCN, and —NO$_2$, wherein each occurrence of $R^{A3}$ is independently hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl; and each occurrence of $R^{A4}$ is independently hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, or a nitrogen protecting group, two R$^{A4}$ groups are joined to form a substituted or unsubstituted heterocyclic ring;

each instance of $R^{AA'}$ is independently halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —OR$^{A3'}$, —N(R$^{A4'}$)$_2$, —SR$^{A3'}$, —C(=O)R$^{A3'}$, —C(=O)OR$^{A3'}$, —C(=O)SR$^{A3'}$, —C(=O)N(R$^{A4'}$)$_2$, —OC(=O)R$^{A3'}$, —OC(=O)OR$^{A3'}$, —OC(=O)SR$^{A3'}$, —OC(=O)N(R$^{A4'}$)$_2$, —NR$^{A4'}$C(=O)R$^{A4'}$, —NR$^{A4'}$C(=O)OR$^{A3'}$, —NR$^{A4'}$C(=O)SR$^{A3'}$, —NR$^{A4'}$C(=O)N(R$^{A4'}$)$_2$, —SC(=O)R$^{A3'}$, —SC(=O)OR$^{A3'}$, —SC(=O)SR$^{A3'}$, —SC(=O)N(R$^{A4'}$)$_2$, —C(=NR$^{A4'}$)R$^{A3'}$, —C(=NR$^{A4'}$)OR$^{A3'}$, —C(=NR$^{A4'}$)SR$^{A3'}$, —C(=NR$^{A4'}$)N(R$^{A4'}$)$_2$, —OC(=NR$^{A4'}$)R$^{A3'}$, —OC(=NR$^{A4'}$)OR$^{A3'}$, —OC(=NR$^{A4'}$)SR$^{A3'}$, —OC(=NR$^{A4'}$)N(R$^{A4'}$)$_2$, —NR$^{A4'}$C(=NR$^{A4'}$)R$^{A3'}$, —NR$^{A4'}$C(=NR$^{A4'}$)OR$^{A3'}$, —NR$^{A4'}$C(=NR$^{A4'}$)SR$^{A3'}$, —NR$^{A4'}$C(=NR$^{A4'}$)N(R$^{A4'}$)$_2$, —SC(=NR$^{A4'}$)R$^{A3'}$, —SC(=NR$^{A4'}$)OR$^{A3'}$, —SC(=NR$^{A4'}$)SR$^{A3'}$, —SC(=NR$^{A4'}$)N(R$^{A4'}$)$_2$, —C(=S)R$^{A3'}$, —C(=S)OR$^{A3'}$, —C(=S)SR$^{A3'}$, —C(=S)N(R$^{A4'}$)$_2$, —OC(=S)R$^{A3}$, —OC(=S)OR$^{A3'}$, —OC(=S)SR$^{A3'}$, —OC(=S)N(R$^{A4'}$)$_2$, —NR$^{A4'}$C(=S)R$^{A4'}$, —NR$^{A4'}$C(=S)OR$^{A3'}$, —NR$^{A4'}$C(=S)SR$^{A3'}$, —NR$^{A4'}$C(=S)N(R$^{A4'}$)$_2$, —SC(=S)R$^{A3'}$, —SC(=S)OR$^{A3'}$, —SC(=S)SR$^{A3}$, —SC(=S)N(R$^{A4'}$)$_2$, —S(=O)R$^{A3'}$, —SO$_2$R$^{A3'}$, —NR$^{A4'}$SO$_2$R$^{A3'}$, —SO$_2$N(R$^{A4'}$)$_2$, —N$_3$, —CN, —SCN, and —NO$_2$, wherein each occurrence of $R^{A3'}$ is independently hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl; and each occurrence of $R^{A4'}$ is independently hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, or a nitrogen protecting group, or two R$^{A4}$ groups are joined to form a substituted or unsubstituted heterocyclic ring.

In some embodiments, the macrocyclic IDE inhibitors provided herein are of Formula (IV):

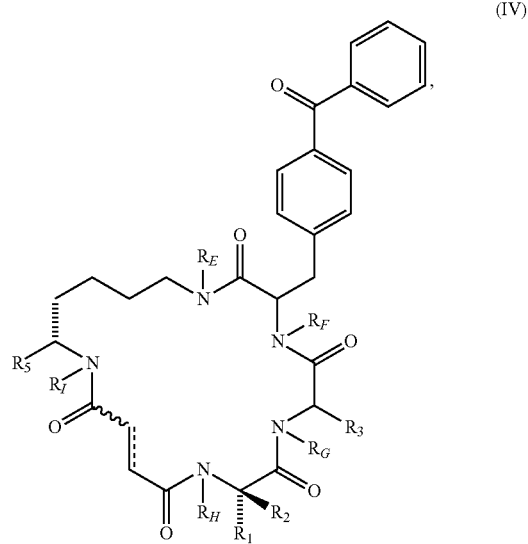

(IV)

or pharmaceutically acceptable salts, solvates, hydrates, stereoisomers, polymorphs, tautomers, isotopically enriched forms, and prodrugs thereof, wherein each instance of $R_1$, $R_2$, $R_3$, $R_5$, $R_E$, $R_F$, $R_G$, $R_H$, and $R_I$ are as defined in Formula (I). In certain embodiments of Formula (IV), $R_1$ represents —H, —$CH_3$, —$CH_2$—$CH_2$—C(=O)—$NH_2$, —$CH_2$—$CH_2$—$CH_2$—NH—C(=NH)—$NH_2$, —$(CH_2)_p$-cyclohexyl, —$(CH_2)$-cyclopentyl, —$(CH_2)_p$-cyclobutyl, —$(CH_2)_p$-cyclopropyl, —$(CH_2)_p$-phenyl, halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —$OR^K$, —$N(R^L)_2$, —$SR^K$, —C(=O)$R^K$, —C(=O)$OR^K$, —C(=O)$SR^K$, —C(=O)$N(R^L)_2$, —OC(=O)$R^K$, —OC(=O)$OR^K$, —OC(=O)$SR^K$, —OC(=O)$N(R^L)_2$, —$NR^LC$(=O)$R^L$, —$NR^LC$(=O)$OR^K$, —$NR^LC$(=O)$SR^K$, —$NR^LC$(=O)$N(R^L)_2$, —SC(=O)$R^K$, —SC(=O)$OR^K$, —SC(=O)$SR^K$, —SC(=O)$N(R^L)_2$, —C(=$NR^L$)$R^K$, —C(=$NR^L$)$OR^K$, —C(=$NR^L$)$SR^K$, —C(=$NR^L$)$N(R^L)_2$, —OC(=$NR^L$)$R^K$, —OC(=$NR^L$)$OR^K$, —OC(=$NR^L$)$SR^K$, —OC(=$NR^L$)$N(R^L)_2$, —$NR^LC$(=$NR^L$)$R^{A3}$, —$NR^LC$(=$NR^L$)$OR^K$, —$NR^LC$(=$NR^L$)$SR^K$, —$NR^LC$(=$NR^L$)$N(R^L)_2$, —SC(=$NR^L$)$R^K$, —SC(=$NR^L$)$OR^K$, —SC(=$NR^L$)$SR^K$, —SC(=$NR^L$)$N(R^L)_2$, —C(=S)$R^K$, —C(=S)$OR^K$, —C(=S)$SR^K$, —C(=S)$N(R^L)_2$, —OC(=S)$R^K$, —OC(=S)$OR^K$, —OC(=S)$SR^K$, —OC(=S)$N(R^L)_2$, —$NR^LC$(=S)$R^L$, —$NR^LC$(=S)$OR^K$, —$NR^LC$(=S)$SR^K$, —$NR^LC$(=S)$N(R^L)_2$, —SC(=S)$R^K$, —SC(=S)$OR^K$, —SC(=S)$SR^K$, —SC(=S)$N(R^L)_2$, —S(=O)$R^K$, —$SO_2R^K$, —$NR^LSO_2R^K$, —$SO_2N(R^L)_2$, —$N_3$, —CN, —SCN, and —$NO_2$, wherein each occurrence of $R^K$ is independently hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl; and each occurrence of $R^L$ is independently hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl; in linear or cyclic form; or a nitrogen protecting group; and each occurrence of p is independently 0 or an integer between 1 and 10 inclusive;

$R_2$ represents —H or —$(CH_2)_q$—$CH_3$, wherein q is 0 or an integer between 1 and 10 inclusive;

$R_3$ represents —$(CH_2)_r$-cyclohexyl, —$(CH_2)_r$-cyclopentyl, —$(CH_2)_r$-cyclobutyl, —$(CH_2)_r$-cyclopropyl, —$(CH_2)_r$-phenyl, or —$(CH_2)_r$—$R_z$, wherein r is independently 0 or an integer between 1 and 10 inclusive, and wherein $R_z$ is hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl; either in linear or cyclic form;

$R_5$ represents C(=O)$NH_2$, or $CH_2$—C(=O)$NH_2$; and $=====$ is a double C—C bond, in either the cis or trans configuration.

In some embodiments, the IDE inhibitory compounds provided herein are of formula (V):

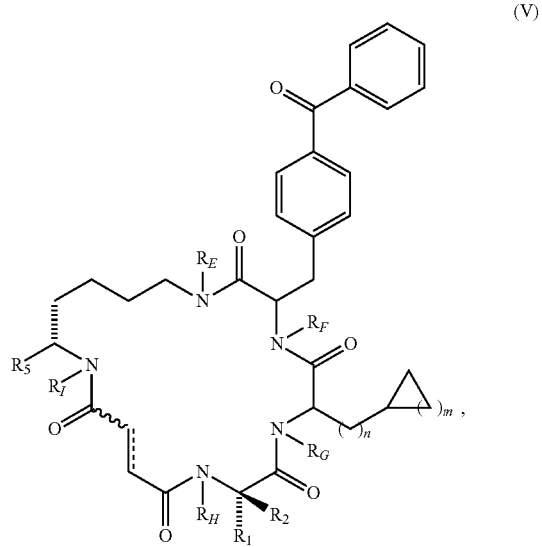

(V)

or pharmaceutically acceptable salts, solvates, hydrates, stereoisomers, polymorphs, tautomers, isotopically enriched forms, and prodrugs thereof, wherein each instance of $R_1$, $R_2$, $R_5$, $R_E$, $R_F$, $R_G$, $R_H$, and $R_I$ are as defined in Formula (I). In certain embodiments of Formula (V), $R_I$ represents —H, —$CH_3$, —$CH_2$—$CH_2$—C(=O)—$NH_2$, —$CH_2$—$CH_2$—$CH_2$—NH—C(=NH)—$NH_2$, —$(CH_2)_p$-cyclohexyl, —$(CH_2)_p$-cyclopentyl, —$(CH_2)_p$-cyclobutyl, —$(CH_2)_p$-cyclopropyl, —$(CH_2)_p$-phenyl, halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —$OR^K$, —$N(R^L)_2$, —$SR^K$, —C(=O)$R^K$, —C(=O)$OR^K$, —C(=O)$SR^K$, —C(=O)$N(R^L)_2$, —OC(=O)$R^K$, —OC(=O)$OR^K$, —OC(=O)$SR^K$, —OC(=O)$N(R^L)_2$, —$NR^LC$(=O)$R^L$, —$NR^LC$(=O)$OR^K$, —$NR^LC$(=O)$SR^K$, —$NR^LC$(=O)$N(R^L)_2$, —SC(=O)$R^K$, —SC(=O)$OR^K$, —SC(=O)$SR^K$, —SC(=O)$N(R^L)_2$, —C(=$NR^L$)$R^K$, —C(=$NR^L$)$OR^K$, —C(=$NR^L$)$SR^K$, —C(=$NR^L$)$N(R^L)_2$, —OC(=$NR^L$)$R^K$, —OC(=$NR^L$)$OR^K$, —OC(=$NR^L$)$SR^K$, —OC(=$NR^L$)$N(R^L)_2$, —$NR^LC$(=$NR^L$)$R^{A3}$, —$NR^LC$(=$NR^L$)$OR^K$, —$NR^LC$(=$NR^L$)$SR^K$, —$NR^LC$(=$NR^L$)$N(R^L)_2$, —SC(=$NR^L$)$R^K$, —SC(=$NR^L$)$OR^K$, —SC(=$NR^L$)$SR^K$, —SC(=$NR^L$)$N(R^L)_2$, —C(=S)$R^K$, —C(=S)$OR^K$, —C(=S)$SR^K$, —C(=S)$N(R^L)_2$, —OC(=S)$R^K$, —OC(=S)$OR^K$, —OC(=S)$SR^K$, —OC(=S)$N(R^L)_2$, —$NR^LC$(=S)$R^L$, —$NR^LC$(=S)$OR^K$, —$NR^LC$(=S)$SR^K$, —$NR^LC$(=S)$N(R^L)_2$, —SC(=S)$R^K$, —SC(=S)$OR^K$, —SC(=S)$SR^K$, —SC(=S)$N(R^L)_2$, —S(=O)$R^K$, —$SO_2R^K$, —$NR^LSO_2R^K$, —$SO_2N(R^L)_2$, —$N_3$, —CN, —SCN, and —$NO_2$, wherein each occurrence of $R^K$ is independently hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl; and each occurrence of $R^L$ is independently hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl; in linear or cyclic form; or a nitrogen protecting group; and each occurrence of p is independently 0 or an integer between 1 and 10 inclusive;

$R_2$ represents —H or —$(CH_2)_q$—$CH_3$, wherein q is 0 or an integer between 1 and 10 inclusive;

$R_5$ represents C(=O)$NH_2$, or $CH_2$—C(=O)$NH_2$;

and wherein each occurrence of n is independently 0 or an integer between 1 and 10 inclusive, each occurrence of m is independently an integer between 1 and 5 inclusive; and ----- is a double C—C bond, in either the cis or trans configuration.

In some embodiments, the macrocyclic IDE inhibitors provided herein are trans-olefins of formula (V), as provided by formula (VI):

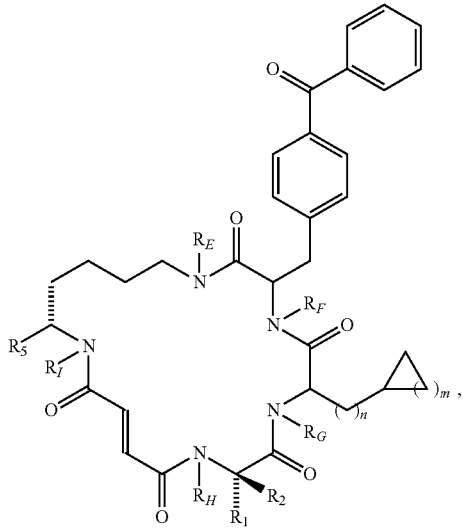

(VI)

or pharmaceutically acceptable salts, solvates, hydrates, stereoisomers, polymorphs, tautomers, isotopically enriched forms, and prodrugs thereof, wherein each instance of $R_1$, $R_2$, $R_E$, $R_F$, $R_G$, $R_H$, and $R_I$ are as defined in Formula (I). In certain embodiments of Formula (VI), $R_I$ represents —H, —$CH_3$, —$CH_2$—$CH_2$—C(=O)—$NH_2$, —$CH_2$—$CH_2$—$CH_2$—NH—C(=NH)—$NH_2$, —$(CH_2)_p$-cyclohexyl, —$(CH_2)_p$-cyclopentyl, —$(CH_2)_p$-cyclobutyl, —$(CH_2)_p$-cyclopropyl, —$(CH_2)_p$-phenyl, halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —$OR^K$, —$N(R^L)_2$, —$SR^K$, —C(=O)$R^K$, —C(=O)$OR^K$, —C(=O)$SR^K$, —C(=O)$N(R^L)_2$, —OC(=O)$R^K$, —OC(=O)$OR^K$, —OC(=O)$SR^K$, —OC(=O)$N(R^L)_2$, —$NR^L$C(=O)$R^L$, —$NR^L$C(=O)$OR^K$, —$NR^L$C(=O)$SR^K$, —$NR^L$C(=O)$N(R^L)_2$, —SC(=O)$R^K$, —SC(=O)$OR^K$, —SC(=O)$SR^K$, —SC(=O)$N(R^L)_2$, —C(=$NR^L$)$R^K$, —C(=$NR^L$)$OR^K$, —C(=$NR^L$)$SR^K$, —C(=$NR^L$)$N(R^L)_2$, —OC(=$NR^L$)$R^K$, —OC(=$NR^L$)$OR^K$, —OC(=$NR^L$)$SR^K$, —OC(=$NR^L$)$N(R^L)_2$, —$NR^L$C(=$NR^L$)$R^{A3}$, —$NR^L$C(=$NR^L$)$OR^K$, —$NR^L$C(=$NR^L$)$SR^K$, —$NR^L$C(=$NR^L$)$N(R^L)_2$, —SC(=$NR^L$)$R^K$, —SC(=$NR^L$)$OR^K$, —SC(=$NR^L$)$SR^K$, —SC(=$NR^L$)$N(R^L)_2$, —C(=S)$R^K$, —C(=S)$OR^K$, —C(=S)$SR^K$, —C(=S)$N(R^L)_2$, —OC(=S)$R^K$, —OC(=S)$OR^K$, —OC(=S)$SR^K$, —OC(=S)$N(R^L)_2$, —$NR^L$C(=S)$R^L$, —$NR^L$C(=S)$OR^K$, —$NR^L$C(=S)$SR^K$, —$NR^L$C(=S)$N(R^L)_2$, —SC(=S)$R^K$, —SC(=S)$OR^K$, —SC(=S)$SR^K$, —SC(=S)$N(R^L)_2$, —S(=O)$R^K$, —$SO_2R^K$, —$NR^L SO_2 R^K$, —$SO_2N(R^L)_2$, —$N_3$, —CN, —SCN, and —$NO_2$, wherein each occurrence of $R^K$ is independently hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl; and each occurrence of $R^L$ is independently hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl; in linear or cyclic form; or a nitrogen protecting group; and each occurrence of p is independently 0 or an integer between 1 and 10 inclusive;

$R_2$ represents —H or —$(CH_2)_q$—$CH_3$, wherein q is 0 or an integer between 1 and 10 inclusive;

$R_5$ represents C(=O)$NH_2$, or $CH_2$—C(=O)$NH_2$;

and wherein n is 0 or an integer between 1 and 10 inclusive, m is an integer between 1 and 5 inclusive; and ----- is a double C—C bond, in either a cis or trans configuration.

In some embodiments, the macrocyclic IDE inhibitors provided herein are of Formula (VII):

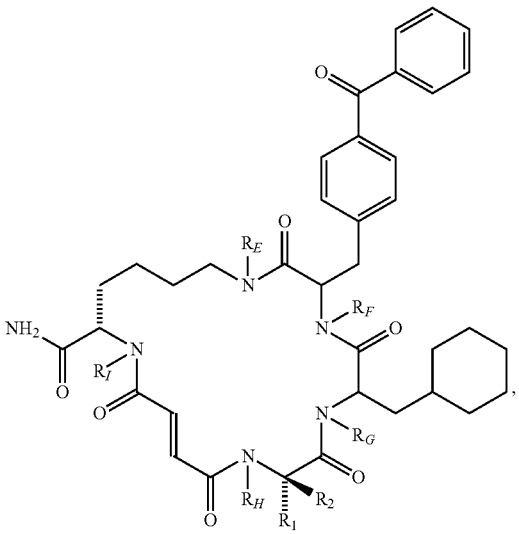

(VII)

or pharmaceutically acceptable salts, solvates, hydrates, stereoisomers, polymorphs, tautomers, isotopically enriched forms, and prodrugs thereof, wherein each instance of $R_1$, $R_2$, $R_E$, $R_F$, $R_G$, $R_H$, and $R_I$ are as defined in Formula (I). In certain embodiments of Formula (VII), $R_I$ represents —H, —$CH_3$, —$CH_2$—$CH_2$—C(=O)—$NH_2$, —$CH_2$—$CH_2$—$CH_2$—NH—C(=NH)—$NH_2$, —$(CH_2)_p$-cyclohexyl, —$(CH_2)_p$-cyclopentyl, —$(CH_2)_p$-cyclobutyl, —$(CH_2)_p$-cyclopropyl, —$(CH_2)_p$-phenyl, halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —$OR^K$, —$N(R^L)_2$, —$SR^K$, —C(=O)$R^K$, —C(=O)$OR^K$, —C(=O)$SR^K$, —C(=O)$N(R^L)_2$, —OC(=O)$R^K$, —OC(=O)$OR^K$, —OC(=O)$SR^K$, —OC(=O)$N(R^L)_2$, —$NR^L$C(=O)$R^L$, —$NR^L$C(=O)$OR^K$, —$NR^L$C(=O)$SR^K$, —$NR^L$C(=O)$N(R^L)_2$, —SC(=O)$R^K$, —SC(=O)$OR^K$, —SC(=O)$SR^K$, —SC(=O)$N(R^L)_2$, —C(=$NR^L$)$R^K$, —C(=$NR^L$)$OR^K$, —C(=$NR^L$)$SR^K$, —C(=$NR^L$)$N(R^L)_2$, —OC(=$NR^L$)$R^K$, —OC(=$NR^L$)$OR^K$, —OC(=$NR^L$)$SR^K$, —OC(=$NR^L$)$N(R^L)_2$, —$NR^L$C(=$NR^L$)$R^{A3}$, —$NR^L$C(=$NR^L$)$OR^K$, —$NR^L$C(=$NR^L$)$SR^K$, —$NR^L$C(=$NR^L$)$N(R^L)_2$, —SC(=$NR^L$)$R^K$, —SC(=$NR^L$)$OR^K$, —SC(=$NR^L$)$SR^K$, —SC(=$NR^L$)$N(R^L)_2$, —C(=S)$R^K$, —C(=S)$OR^K$, —C(=S)

$SR^K$, $-C(=S)N(R^L)_2$, $-OC(=S)R^K$, $-OC(=S)OR^K$, $-OC(=S)SR^K$, $-OC(=S)N(R^L)_2$, $-NR^LC(=S)R^L$, $-NR^LC(=S)OR^K$, $-NR^LC(=S)SR^K$, $-NR^LC(=S)N(R^L)_2$, $-SC(=S)R^K$, $-SC(=S)OR^K$, $-SC(=S)SR^K$, $-SC(=S)N(R^L)_2$, $-S(=O)R^K$, $-SO_2R^K$, $-NR^LSO_2R^K$, $-SO_2N(R^L)_2$, $-N_3$, $-CN$, $-SCN$, and $-NO_2$, wherein each occurrence of $R^K$ is independently hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl; and each occurrence of $R^L$ is independently hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl; in linear or cyclic form; or a nitrogen protecting group; and each occurrence of p is independently 0 or an integer between 1 and 10 inclusive;

$R_2$ represents $-H$ or $-(CH_2)_q-CH_3$, wherein q is 0 or an integer between 1 and 10 inclusive;

$R_5$ represents $-C(=O)NH_2$, or $-CH_2-C(=O)NH_2$; and wherein

----- is a double C—C bond, in either a cis or trans configuration.

In some embodiments, $R_1$ represents $-H$, $-CH_3$, $-CH_2-CH_2-C(=O)-NH_2$, $-CH_2-CH_2-CH_2-NH-C(=NH)-NH_2$, $-(CH_2)_n$-cyclohexyl, $-(CH_2)_n$-cyclopentyl, $-(CH_2)_n$-cyclobutyl, $-(CH_2)_n$-cyclopropyl, or $-(CH_2)_n$-phenyl; $R_E$, $R_F$, $R_G$, $R_H$, and $R_I$ are H; and $R_2$ is $-H$ or $-CH_2-CH_3$. In some embodiments, $R_1$ represents $-H$, $-CH_3$, $-CH_2-CH_2-C(=O)-NH_2$, $-CH_2-CH_2-CH_2-NH-C(=NH)-NH_2$, $-(CH_2)$-cyclohexyl, $-(CH_2)$-cyclopentyl, $-(CH_2)$-cyclobutyl, $-(CH_2)$-cyclopropyl, or $-(CH_2)$-phenyl; $R_E$, $R_F$, $R_G$, $R_H$, and $R_I$ are H; and $R_2$ is $-H$ or $-CH_2-CH_3$.

Some non-limiting examples of macrocyclic inhibitors of IDE provided herein include compounds of the following formulae (VIII)-(XI):

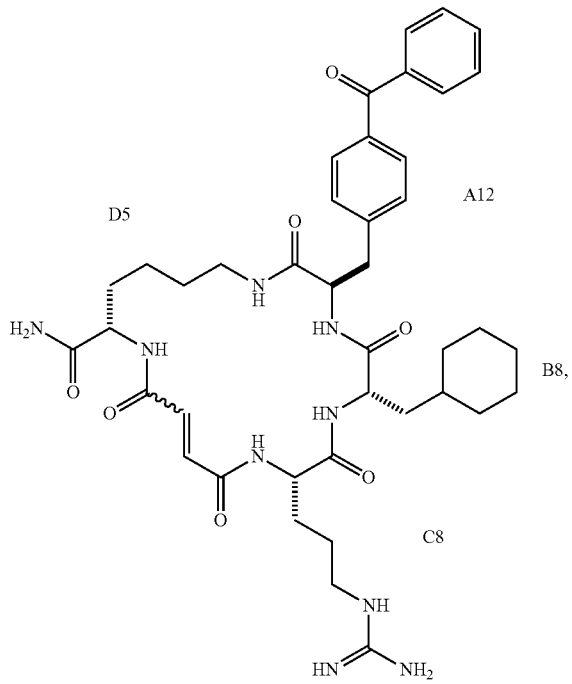

(IX)

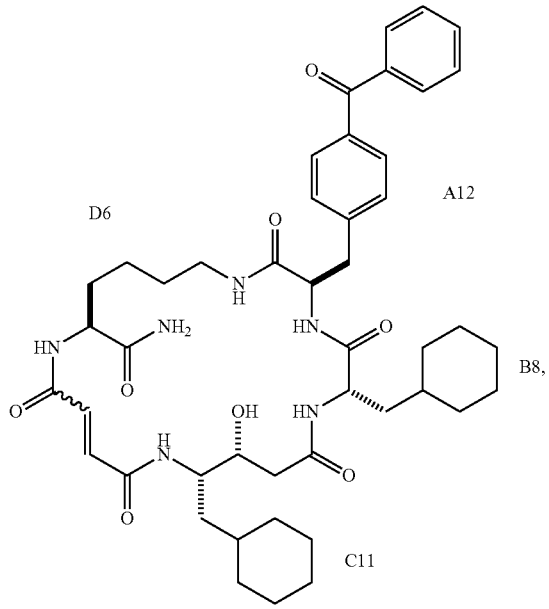

(VIII)

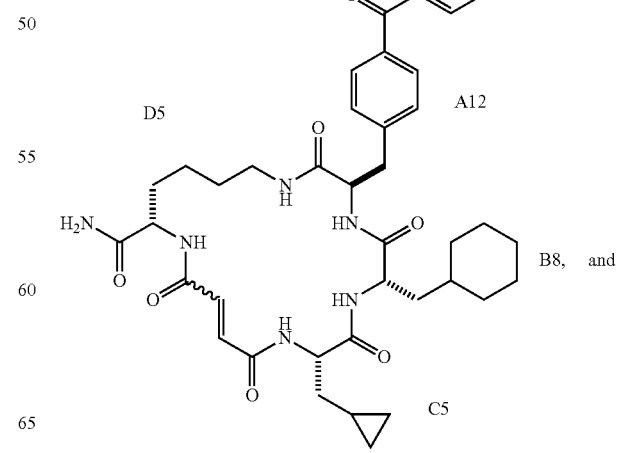

(X), and

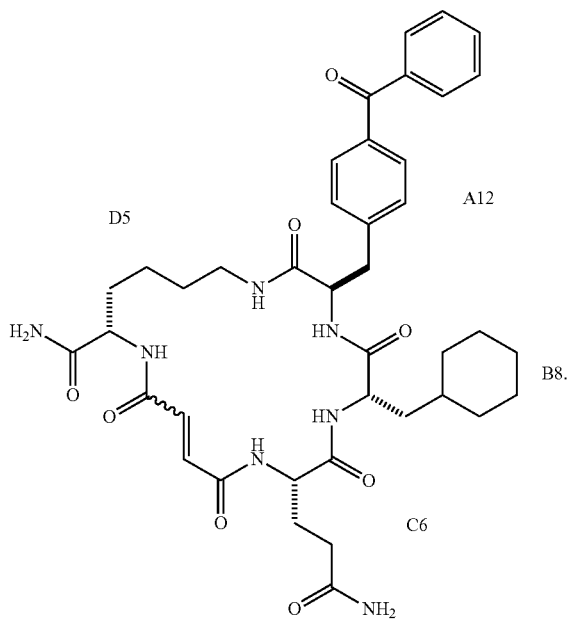

(XI)

Figures 1, 3:
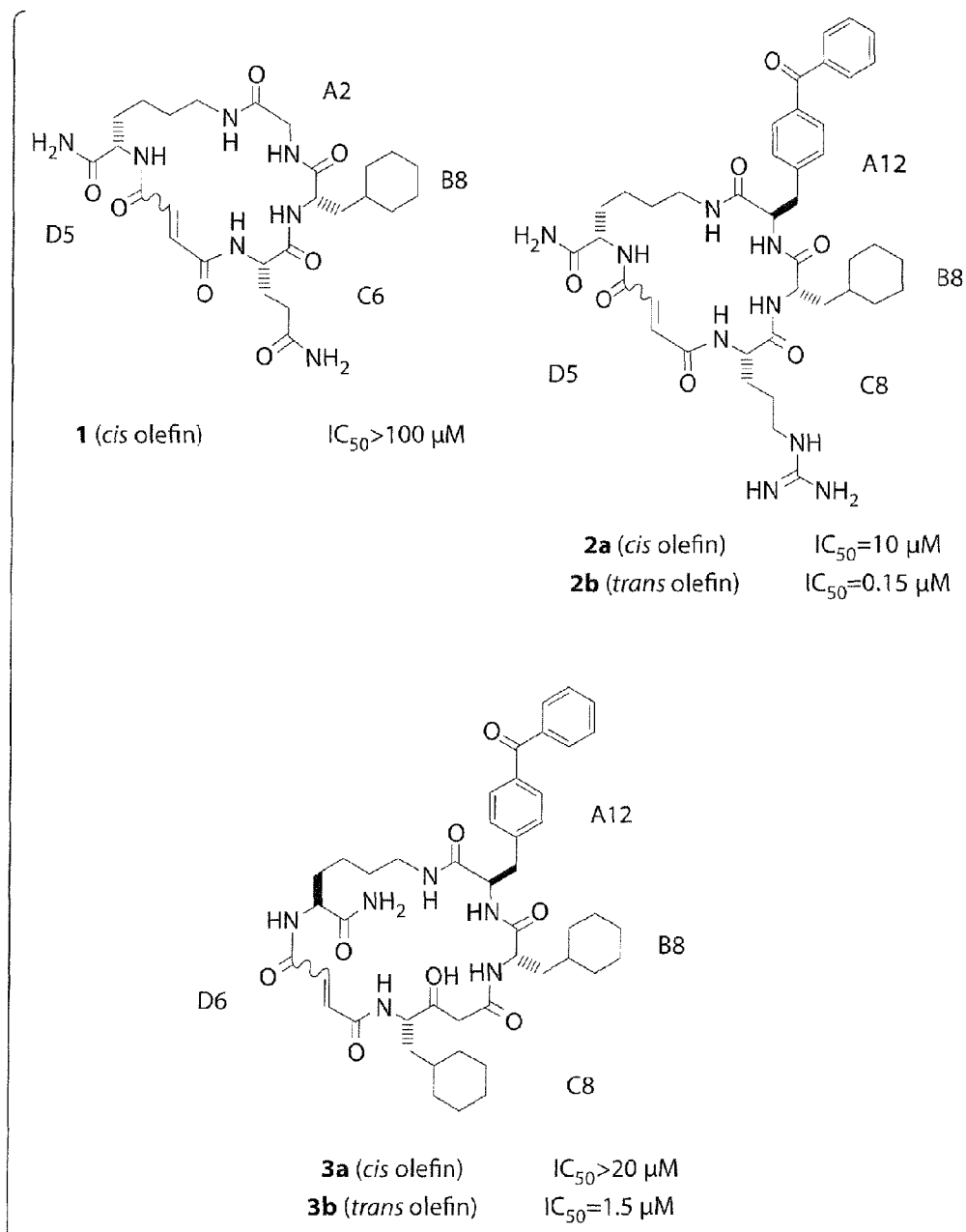
FIG. 3. $IC_{50}$ values of cis- and trans-olefins of exemplary, enriched macrocycles against IDE. Lower panel: Derivatives of macrocycle 6b. $IC_{50}$ values were measured against IDE as described above. *The D-4-phenyl-phenylalanine derivative (8) could only be isolated in its cis-olefin form. **The $IC_{50}$ value for compound 14 was extrapolated since it displayed behavior consistent with insolubility at high concentrations.
Figures 2, 3:
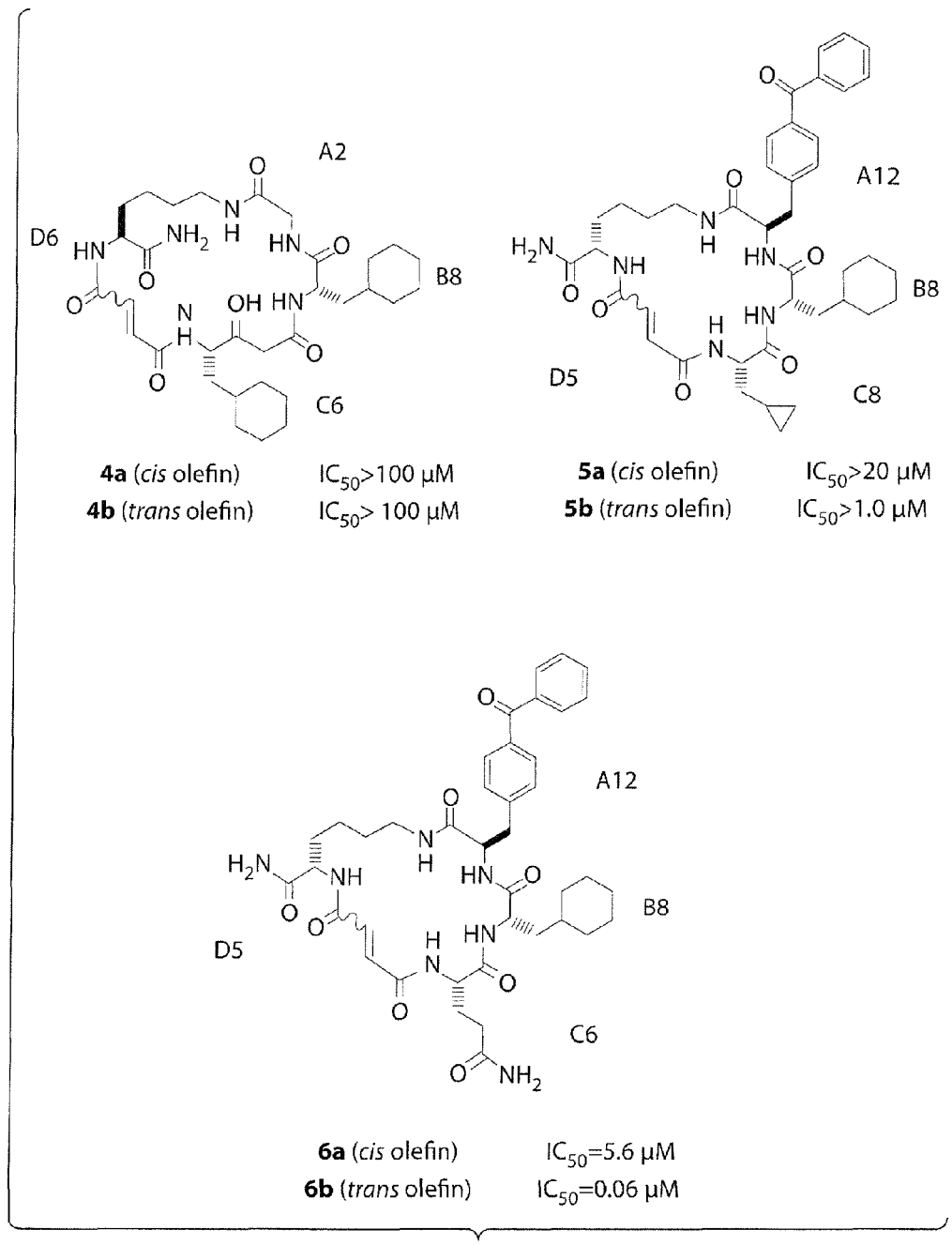
Figure 3:
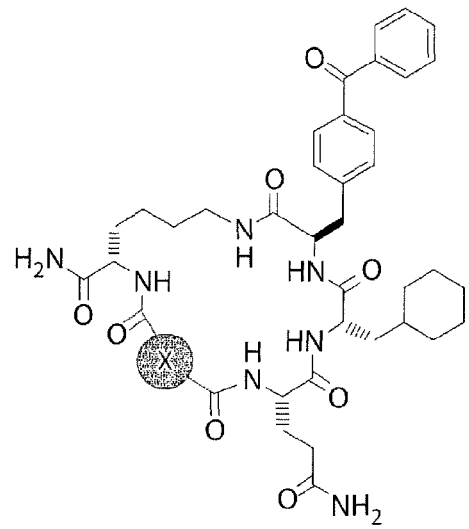
Figure 3:
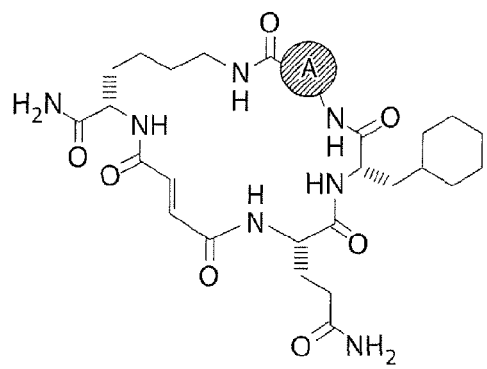
Figure 3:
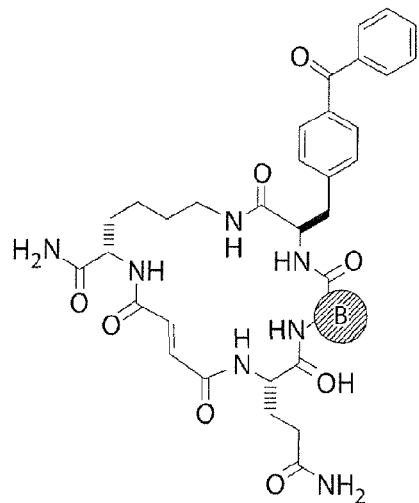

In some embodiments, the macrocyclic IDE inhibitors provided herein include a C=C double bond in the macrocycle backbone. The position of this double bond is provided as ------ in Formulae (I)-(V), and (VII) and as = in Formulae (VI), and (VIII)-(XI). In some embodiments, the macrocycle backbone C=C double bond is in the cis-configuration. The respective macrocycles are also referred to herein as cis-olefins. In some embodiments, the macrocycle backbone C=C double bond is in the trans-olefin configuration. The respective macrocycles are also referred to herein as trans-olefins. As shown in FIG. 3, cis- and trans-olefins can have significantly different $IC_{50}$ values, and thus, inhibit IDE at different potencies. In some embodiments, a macrocyclic IDE inhibitor described herein, for example, macrocycle 6b, is provided as a cis-olefin, without any significant or any detectable amount of the respective trans-olefin isomer. In some embodiments, an IDE inhibitor described herein, for example, macrocycle 6b, is provided as a trans-olefin, without any significant or any detectable amount of the respective cis-olefin isomer. In some embodiments, an IDE inhibitor described herein is provided as a mixture of cis-olefin and trans-olefin isomers. Methods for the synthesis of the IDE inhibitors described herein in the cis- or trans-configuration are described herein. Additional methods useful for the synthesis and production of cis- and trans-olefins that are useful for the generation of the macrocyclic IDE inhibitors disclosed herein are known to those of skill in the art, and the invention is not limited in this respect.

In some embodiments, a macrocyclic IDE inhibitor as described herein is provided that comprises a tag. In some embodiments, the tag is a fluorescent tag, for example, a fluorescent molecule or moiety, that is conjugated, for example, covalently via a linker, to the macrocycle. In some embodiments, the fluorescent tag is a fluorescent protein tag, for example, a GFP tag, a YFP tag, an RFP tag, a BFP tag, or a tag comprising an enhanced fluorescent protein, such as eGFP. Other fluorescent proteins and protein tags are well known to those of skill in the art. In some embodiments, the tag is a cyane dye, or CyDye tag, for example, a Cy3 or C5 tag.

In some embodiments, the tag is a fluorescein tag. In some embodiments, the tag is conjugated to the macrocycle structure via a linker. Additional suitable fluorescent tags are known to those of skill in the art and the invention is not limited in this respect. In some embodiments, the tag comprises a binding agent. In some embodiments, the binding agent is an antibody or an antigen-binding antibody fragment, a nanobody, an ScFv, an aptamer, or an adnectin. In some embodiments, the binding agent is a ligand, for example, biotin, polyhistidine, or FK506. Other binding agents are known to those of skill in the art and the invention is not limited in this respect. In some embodiments, the binding agent specifically binds an antigen, for example, an antigen immobilized on a solid surface or a cellular antigen, e.g., a cell-surface antigen. In some embodiments, the tag comprising a binding agent specifically binds to a particular cell or cell type, for example, to a pancreatic cell. In some embodiments, such binding-agent-tagged macrocycles target a specific site characterized by expression of the antigen bound by the binding agent, for example, after administration to a subject harboring such a target site. Antigens useful for targeting specific cells, cell types, tissues, or organs, for example, malignant cells, cell types, tissues, or organs, are well known to those of skill in the art and the invention is not limited in this respect.

Figure 14:
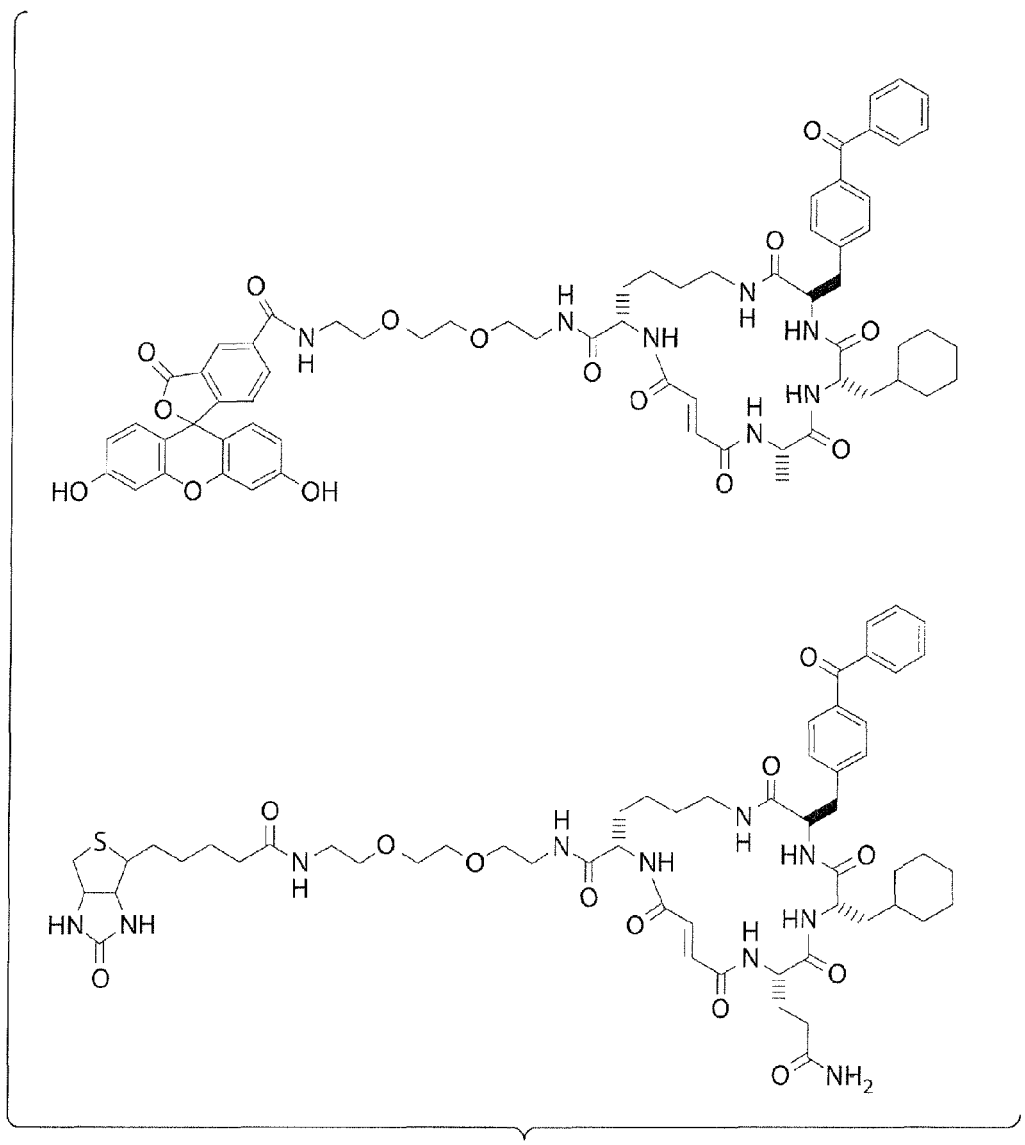
FIG. 14. Examples of tagged-inhibitors which can be used as probes.

The disclosure also embraces pharmaceutically acceptable salts of the macrocyclic IDE inhibitor disclosed herein, whether conjugated to a tag or not, as well as pharmaceutical compositions comprising the IDE inhibitors disclosed herein, or a pharmaceutically acceptable salt thereof. The disclosure also embraces tagged forms of the IDE inhibitors described herein, for example, IDE inhibitors that are conjugated to a binding agent (e.g., an antibody or an antibody fragment, an antigen, an epitope, a ligand, a receptor, an affibody, an anticalin, an adnectin or an aptamer), or to a detectable label (e.g., a fluorophore or an isotope). FIG. 14 shows two exemplary tagged IDE inhibitors provided herein. Such tagged IDE inhibitors can be used, e.g., as molecular probes.

Methods for Preparing Macrocyclic IDE Inhibitors

The present invention further provides methods for preparing macrocyclic IDE inhibitors of the present invention, e.g., following the synthetic steps depicted in Schemes 1-6 below. The preparation of macrocyclic compounds is also described in international PCT application, PCT/US2011/045966, entitled "Macrocyclic Kinase Inhibitors and Uses Thereof," filed Jul. 29, 2011, published as WO/2012/016186, and in Kleiner et al., "In Vitro Selection of a DNA-Templated Macrocycle Library Reveals a Class of Macrocyclic Kinase Inhibitors." *J. Am. Chem. Soc.* 132, 11779-11791 (2010), the entire contents of each of which are incorporated herein by reference.

Scheme 1 depicts the first two steps in the synthesis of a compound of Formula (I). Step 1 (S-1) comprises providing a compound of Formula (A), wherein $R^4$ is as defined herein, and $R^{Y1}$ is a nitrogen protecting group, providing a compound of Formula (B), wherein $R^{X1}$ is a carboxylic acid protecting group, and $R^{X2}$ and $R^{X3}$ are each independently oxygen protecting groups or are cyclized to form a 1,2-diol protecting group (e.g., a dioxolanyl group), and coupling the compound of Formula (A) and the compound of Formula (B) under peptide coupling conditions to provide the coupled product (C). Step 2 (S-2) comprises deprotecting the coupled product (C) to provide a compound of formula (D).

Scheme 1.

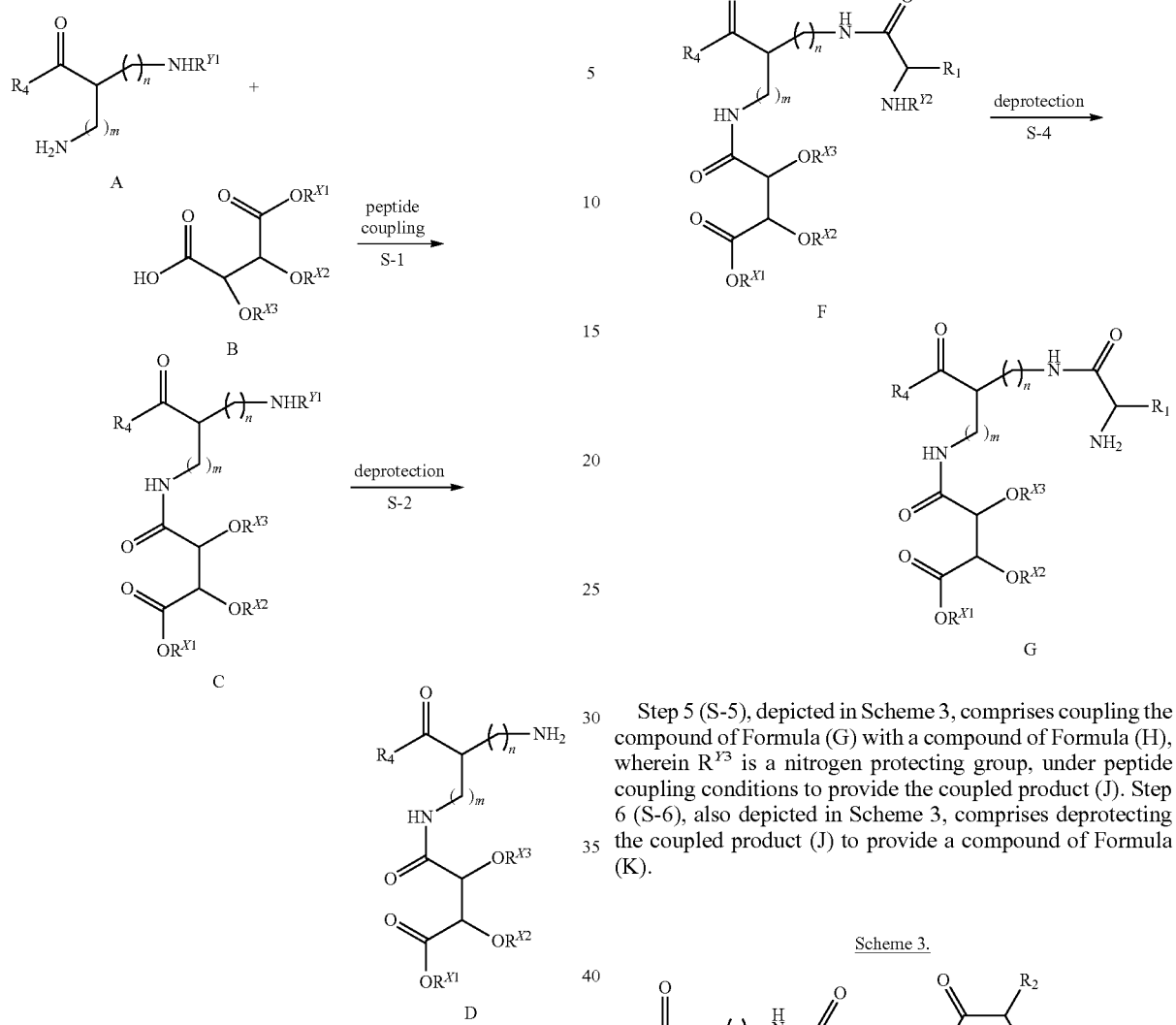

Step 3 (S-3), depicted in Scheme 2, comprises coupling the compound of Formula (D) with a compound of Formula (E), wherein $R^{Y2}$ is a nitrogen protecting group, under peptide coupling conditions to provide the coupled product (F). Step 4 (S-4), also depicted in Scheme 2, comprises deprotecting the coupled product (F) to provide a compound of Formula (G).

Scheme 2.

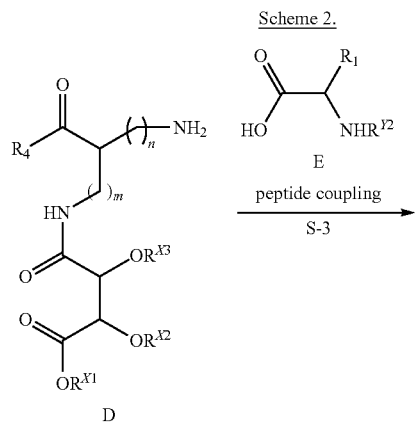

Step 5 (S-5), depicted in Scheme 3, comprises coupling the compound of Formula (G) with a compound of Formula (H), wherein $R^{Y3}$ is a nitrogen protecting group, under peptide coupling conditions to provide the coupled product (J). Step 6 (S-6), also depicted in Scheme 3, comprises deprotecting the coupled product (J) to provide a compound of Formula (K).

Scheme 3.

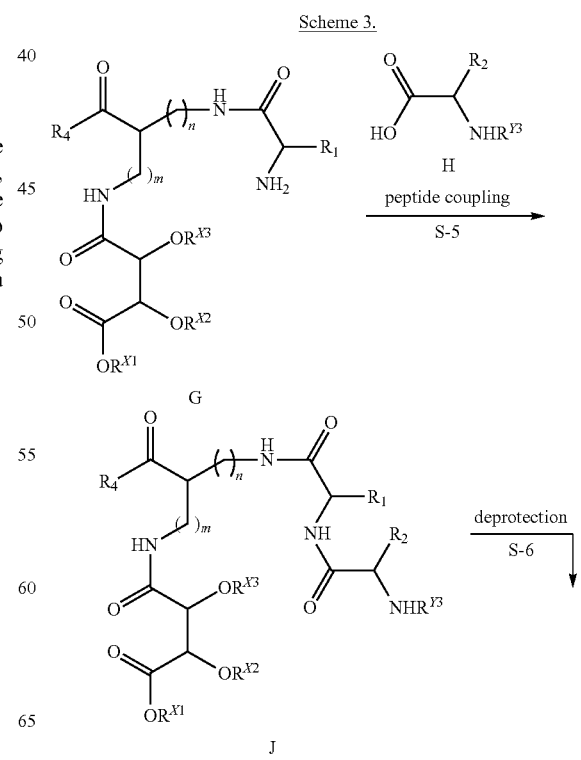

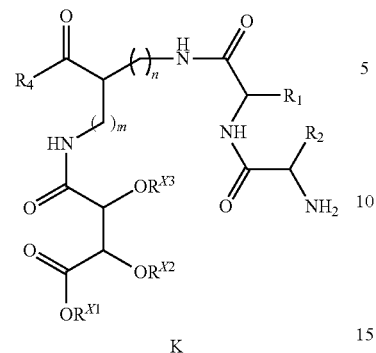

Step 7 (S-7), depicted in Scheme 4, comprises coupling the compound of Formula (K) with a compound of Formula (L), wherein $R^{Y4}$ is a nitrogen protecting group, under peptide coupling conditions to provide the coupled product (M). Step 8 (S-8), also depicted in Scheme 4, comprises deprotecting the coupled product (M) to provide a compound of Formula (N).

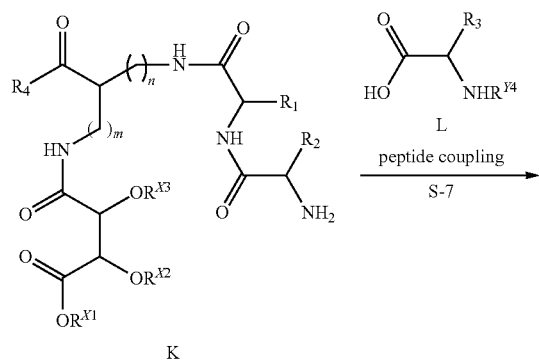

Step 9 (S-9), depicted in Scheme 5, comprises acylating the compound of Formula (N) to provide the acylated product (P), wherein X is —Br, —Cl, or —I. An exemplary acylating reagent is an amine reactive ester of the formula Y—C(=O)CH$_2$X, wherein Y is a N-hydroxysuccinimide (NHS) or sulfo-NHS. Step 10 (S-10) comprises contacting the acylated product (P) with a phosphine of formula P(R$^Z$)$_3$, wherein each R$^Z$ is independently optionally substituted aryl or optionally substituted heteroaryl, to provide a phosphonium salt of the Formula (Q). Step 11 (S-11) comprises deprotecting the 1,2-diol to provide a compound of Formula (R).

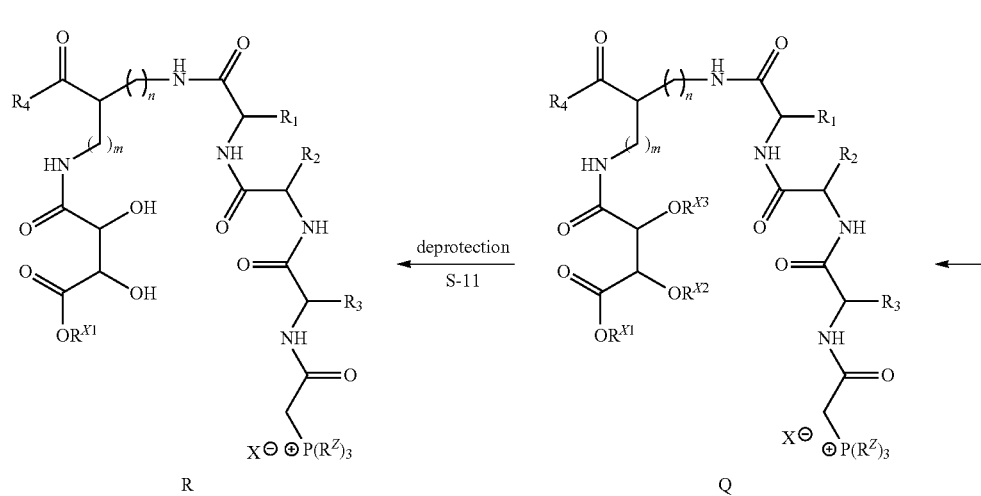
Step 12 (S-12), depicted in Scheme 6, comprises cleaving the 1,2-diol under oxidative conditions to provide the aldehyde intermediate (S) in situ. Exposure of the aldehyde intermediate (S) under basic conditions (e.g., pH>8) generates a phosphonium ylide, and the subsequent intramolecular Wittig reaction provides an exemplary macrocyclic compound of Formula (I).
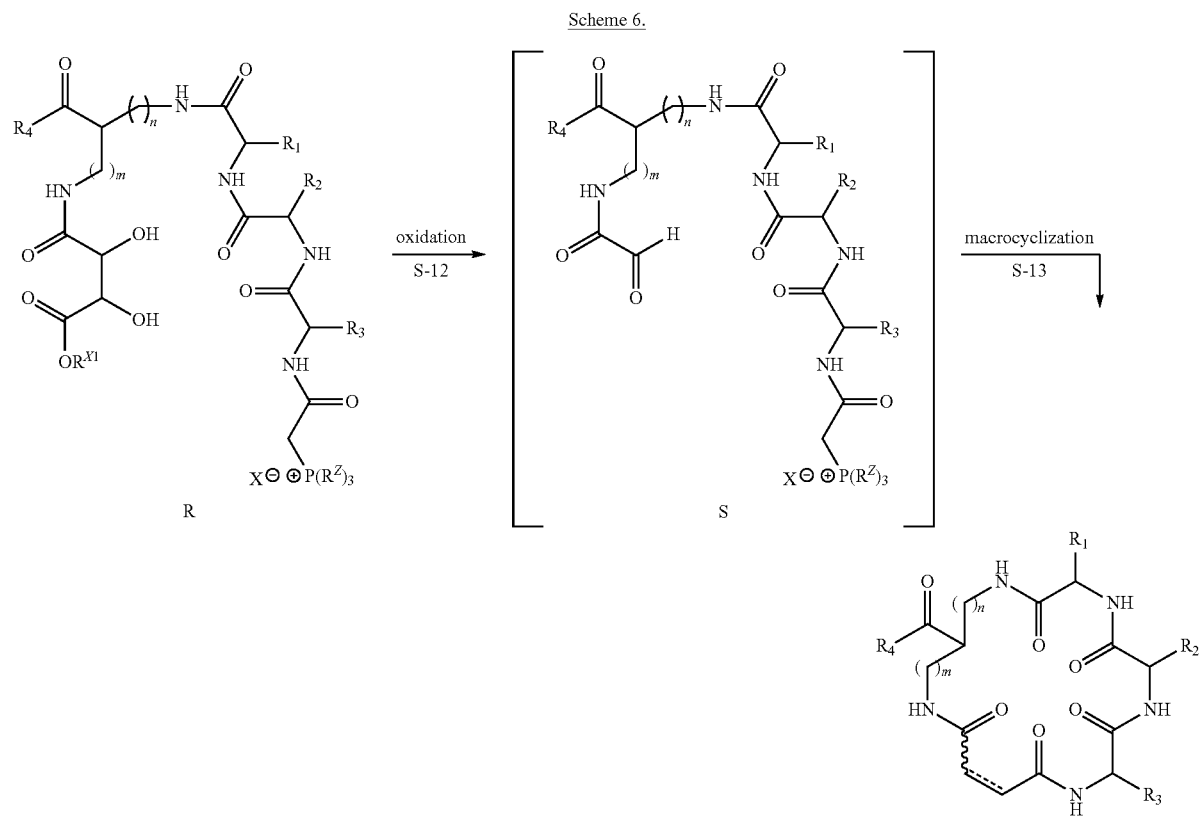

In some embodiments, of the synthetic Schemes 1-6, each instance of $R_1$, $R_2$, $R_3$, $R_E$, $R_F$, $R_G$, $R_H$, and $R_I$ are as defined in Formula (I). In some embodiments, $R_3$ represents halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —$OR^K$, —$N(R^L)_2$, —$SR^K$, —$C(=O)R^K$, —$C(=O)OR^K$, —$C(=O)SR^K$, —$C(=O)N(R^L)_2$, —$OC(=O)R^K$, —$OC(=O)OR^K$, —$OC(=O)SR^K$, —$OC(=O)N(R^L)_2$, —$NR^LC(=O)R^L$, —$NR^LC(=O)OR^K$, —$NR^LC(=O)SR^K$, —$NR^LC(=O)N(R^L)_2$, —$SC(=O)R^K$, —$SC(=O)OR^K$, —$SC(=O)SR^K$, —$SC(=O)N(R^L)_2$, —$C(=NR^L)R^K$, —$C(=NR^L)OR^K$, —$C(=NR^L)SR^K$, —$C(=NR^L)N(R^L)_2$, —$OC(=NR^L)R^K$, —$OC(=NR^L)OR^K$, —$OC(=NR^L)SR^K$, —$OC(=NR^L)N(R^L)_2$, —$NR^LC(=NR^L)R^{A3}$, —$NR^LC(=NR^L)OR^K$, —$NR^LC(=NR^L)SR^K$, —$NR^LC(=NR^L)N(R^L)_2$, —$SC(=NR^L)R^K$, —$SC(=NR^L)OR^K$, —$SC(=NR^L)SR^K$, —$SC(=NR^L)N(R^L)_2$, —$C(=S)R^K$, —$C(=S)OR^K$, —$C(=S)SR^K$, —$C(=S)N(R^L)_2$, —$OC(=S)R^K$, —$OC(=S)OR^K$, —$OC(=S)SR^K$, —$OC(=S)N(R^L)_2$, —$NR^LC(=S)R^L$, —$NR^LC(=S)OR^K$, —$NR^LC(=S)SR^K$, —$NR^LC(=S)N(R^L)_2$, —$SC(=S)R^K$, —$SC(=S)OR^K$, —$SC(=S)SR^K$, —$SC(=S)N(R^L)_2$, —$S(=O)R^K$, —$SO_2R^K$, —$NR^LSO_2R^K$, —$SO_2N(R^L)_2$, —$N_3$, —CN, —SCN, and —$NO_2$, wherein each occurrence of $R^K$ is independently hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl; and each occurrence of $R^L$ is independently hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl; in linear or cyclic form; or a nitrogen protecting group; and each occurrence of n is independently 0 or an integer between 1 and 10 inclusive. In some embodiments, $R_2$ represents —H or —$(C)_n$—$CH_3$, wherein n is 0 or an integer between 1 and 10 inclusive. In some embodiments, $R_3$ represents —$(CH_2)_n$-cyclohexyl, —$(CH_2)_n$-phenyl, or $(CH_2)_n$—$R_z$, wherein n is independently 0 or an integer between 1 and 10 inclusive, and wherein $R_z$ is hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl; either in linear or cyclic form. In some embodiments, $R_4$ is $NH_2$. In some embodiments, ------ is a double C—C bond, in the cis configuration. In some embodiments, ------ is a double C—C bond, in the trans configuration. In some embodiments, $R_3$ represents —H, —$CH_3$, —$CH_2$—$CH_2$—C(=O)—$NH_2$, —$CH_2$—$CH_2$—$CH_2$—NH—C(=NH)—$NH_2$, —$(CH_2)_n$-cyclohexyl, or —$(CH_2)_n$-cyclopropyl. In some embodiments, $R_E$, $R_F$, $R_G$, $R_H$, and $R_I$ are —H.

As is understood from the above, the synthesis utilizes peptide coupling methods. Such methods are known in the art, see generally, *March's Advanced Organic Chemistry: Reactions, Mechanisms, and Structure*, M. B. Smith and J. March, $5^{th}$ Edition, John Wiley & Sons, 2001, and *Comprehensive Organic Transformations*, R. C. Larock, $2^{nd}$ Edition, John Wiley & Sons, 1999.

The peptide coupling reaction requires a peptide coupling reagent. Exemplary peptide coupling reagents include, but are not limited to, benzotriazol-1-yloxy-tris(dimethylamino)-phosphonium hexafluorophosphate (BOP), benzotriazole-1-yl-oxy-tris-pyrrolidino-phosphonium hexafluorophosphate (PyBOP), bromo-tris-pyrrolidino phosphonium hexafluorophosphate (PyBroP), 1-ethyl-3-(3-dimethylaminopropyl) carbodiimide (EDC), N,N'-carbonyldiimidazole (CDI), 3-(diethoxyphosphoryloxy)-1,2,3-benzotriazin-4 (3H)-one (DEPBT), 1-hydroxy-7-azabenzotriazole (HOAt), 1-hydroxy-7-benzotriazole (HOBt), 2-(7-aza-1H-benzotriazole-1-yl)-1,1,3,3-tetramethyluronium hexafluorophosphate (HATU), 2-(6-chloro-1H-benzotriazole-1-yl)-1,1,3,3-tetramethylaminium hexafluorophosphate (HCTU), 2-(1H-benzotriazole-1-yl)-1,1,3,3-tetramethyluronium hexafluorophosphate (HBTU), O-(7-azabenzotriazole-1-yl)-N,N,N',N'-tetramethyluronium tetrafluoroborate (TATU), 2-(1H-benzotriazole-1-yl)-1,1,3,3-tetramethyluronium tetrafluoroborate (TBTU), N,N,N',N'-tetramethyl-O-(3,4-dihydro-4-oxo-1,2,3-benzotriazin-3-yl)uranium tetrafluoroborate (TDBTU), and O—(N-succinimidyl)-1,1,3,3-tetramethyl uranium tetrafluoroborate (TSTU)).

In certain embodiments, the peptide coupling reaction further comprises a base, e.g., potassium carbonate, potassium hydroxide, sodium hydroxide, tetrabutylammonium hydroxide, benzyltrimethylammonium hydroxide, triethylbenzylammonium hydroxide, 1,1,3,3-tetramethylguanidine, 1,8-diazabicyclo[5.4.0]undec-7-ene (DBU), N-methylmorpholine, diisopropylethylamine (DIPEA), tetramethylethylenediamine (TMEDA), pyridine (Py), 1,4-diazabicyclo[2.2.2]octane (DABCO), N,N-dimethylamino pyridine (DMAP), or triethylamine ($NEt_3$).

In certain embodiments, the peptide coupling is a solid phase peptide coupling. For example, in some embodiments, the macrocyclic compound is synthesized using solid-phase peptide synthesis. In this particular instance, in certain embodiments, $R^4$ is —$NHR^D$, wherein $R^D$ is a resin, e.g, a Rink amide resin. An overview of exemplary solid phase methods can be found, for example, in Chan, W C, White, P D, *Fmoc Solid Phase Peptide Synthesis: A Practical Approach (Practical Approach Series)*, Oxford University Press, USA; $1^{st}$ edition (Mar. 2, 2000), ISBN-10: 0199637245; incorporated herein in its entirety for disclosure of Fmoc and solid phase Fmoc synthetic methods and related protocols). In certain embodiments, the method comprises generating the phosphonium salt (Q) on the resin, and then cleaving the compound from the resin prior to Step 12 (S-12). In certain embodiments, the phosphonium salt (Q) is cleaved from the resin by treatment with an acid (e.g., trifluoroacetic acid, TFA). In certain embodiments, the acidic conditions also cleave the 1,2-diol protecting group to provide a compound of Formula (R). In certain embodiments, prior to the oxidative and cyclization steps (Steps 12 and 13), the method further comprises purifying the compound of Formula (R). Methods for isolating and/or purifying synthesized peptides are well known to those of skill in the art and include, but are not limited to, high performance liquid chromatography (HPLC), conventional column chromatography, or recrystallization.

However, in certain embodiments, the peptide coupling is a solution phase peptide coupling, and the starting materials, intermediates, and final products are not attached to a resin.

In another aspect, provided is a method of preparing a macrocyclic IDE inhibitor as described herein, the method comprising:

(a) providing a differentially protected diamino acid macrocyclization precursor of the formula:

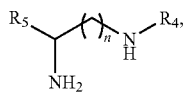

wherein:
n is 0 or is an integer between 0 and 10, inclusive;
$R_4$ is an amino protecting group;
$R_5$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted acyl; substituted or unsubstituted aryl; substituted or unsubstituted heteroaryl; —$OR_D$; =O; —C(=O)$R_D$; —$CO_2R_D$; —CN; —SCN; —$SR_D$; —$SOR_D$; —$SO_2R_D$; —$NO_2$; —N($R_D$)$_2$; —NHC(O)$R_D$; or —C($R_D$)$_3$; wherein each occurrence of $R_D$ is independently hydrogen, a protecting group, aliphatic, heteroaliphatic, substituted or unsubstituted acyl; aryl; heteroaryl; alkoxy; aryloxy; alkylthio; arylthio; amino, alkylamino, dialkylamino, heteroaryloxy; or heteroarylthio; and optionally, wherein the macrocyclization precursor is coupled to a solid support via $R_5$;

(b) contacting the macrocyclization precursor provided by step (a) with a building block of the formula:

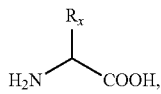

under conditions suitable for the formation of a peptide bond between the carboxyl group of the building block provided by step (b) with the unprotected amino group of the macrocyclization precursor, wherein $R_x$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted acyl; substituted or unsubstituted aryl; substituted or unsubstituted heteroaryl; —$OR_E$; =O; —C(=O)$R_E$; —$CO_2R_E$; —CN; —SCN; —$SR_E$; —$SOR_E$; —$SO_2R_E$; —$NO_2$; —N($R_E$)$_2$; —NHC(O)$R_E$; or —C($R_E$)$_3$; wherein each occurrence of $R_E$ is independently hydrogen; a protecting group; aliphatic; heteroaliphatic; substituted or unsubstituted acyl; aryl; heteroaryl; alkoxy; aryloxy; alkylthio; arylthio; amino; alkylamino; dialkylamino; heteroaryloxy; or heteroarylthio;

(c) performing 1-5 additional steps of contacting the reaction product generated by step (b) with an additional building block of the formula recited in step (b), wherein $R_x$ is defined for each building block separately and individually as recited in step (b);

(d) optionally, cleaving the macrocyclization precursor from the solid support and/or purifying the macrocyclization precursor; and (e) cyclizing the macrocyclization precursor to obtain a macrocyclic IDE inhibitor.

In certain embodiments, n is an integer between 1 and 4, inclusive.

In certain embodiments, $R_4$ is an amino protecting group. In certain embodiments, $R_4$ is isopropylidene-protected tartrate monomethyl ester.

In certain embodiments, the macrocyclization precursor is coupled to an amide resin. In certain embodiments, the building blocks are added to the macrocyclization precursor by Fmoc synthesis. In certain embodiments, the method comprises generating a phosphonium salt of the macrocyclization precursor on resin.

In certain embodiments, the macrocyclization precursor is cleaved from the solid support by treatment with a strong acid. In certain embodiments, the cleavage reaction generates a carboxamide at the C-terminus and deprotects a tartrate diol group.

In certain embodiments, the macrocyclization precursor is purified before cyclization. In certain embodiments, the method further comprises a step of oxidatively cleaving the diol group, thus generating an aldehyde group. In certain embodiments, the cyclization is a Wittig cyclization. In certain embodiments, the Wittig cyclization is effected by raising the pH of the reaction mixture to generate a phosphonium ylide.

Figure 13:
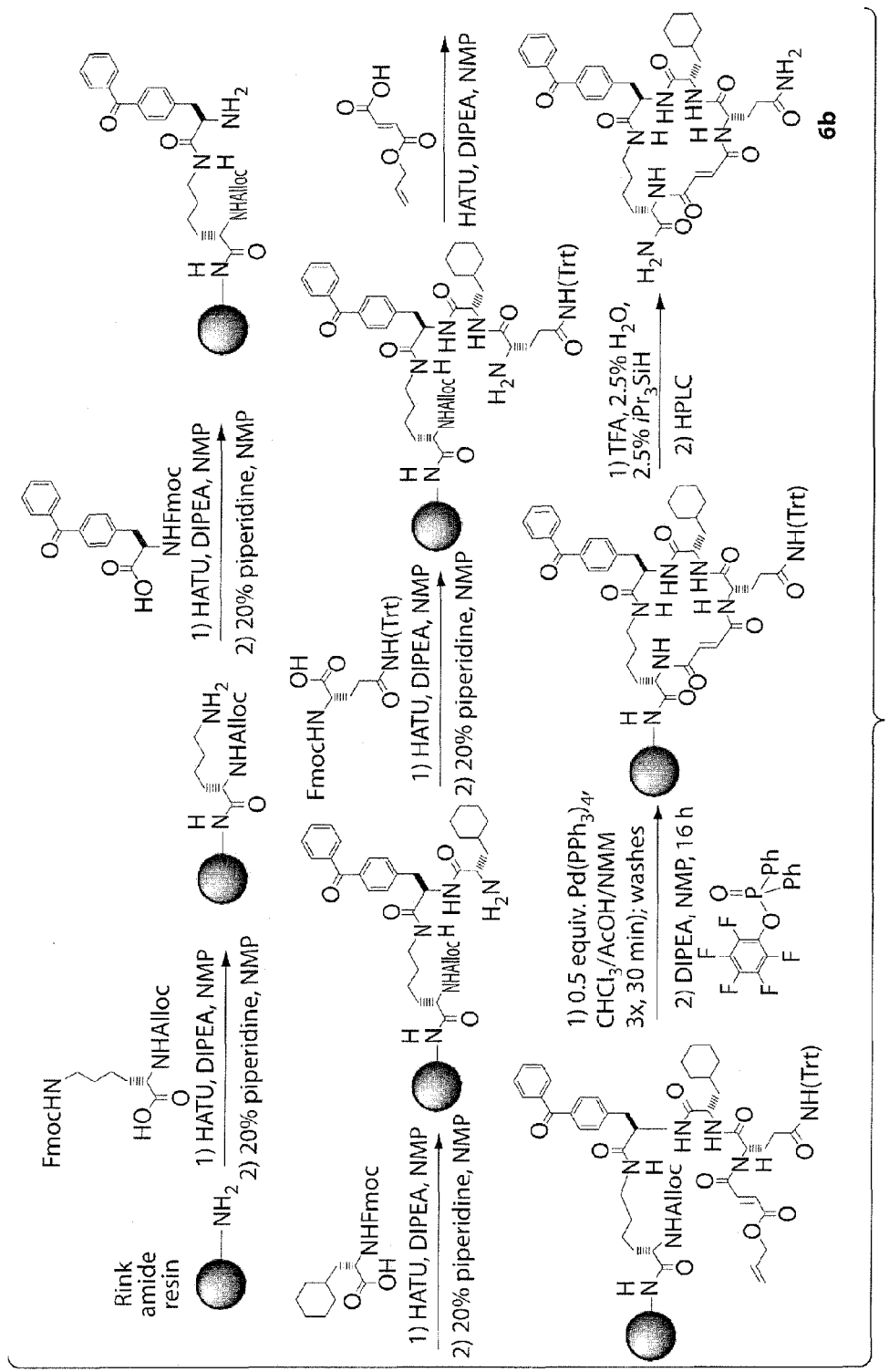
FIG. 13. Solid phase synthesis of macrocycles.

In certain embodiments, a solid support synthetic strategy for producing only the trans isomers of the IDE inhibitors described herein is provided as outlined in FIG. 13.

Methods of using IDE Inhibitors

In another aspect, this invention provides in vitro or in vivo methods of inhibiting the activity of an insulin degrading enzyme (IDE). Such methods are useful for inhibiting IDE, for example, in cell culture or in a subject. In some embodiments, inhibition of IDE results in a stabilization (e.g., greater half-life) of insulin and in improved (e.g., increased) insulin signaling. Accordingly, the in vivo methods of using the macrocyclic IDE inhibitors provided herein are useful in improving insulin signaling in subjects having a disease associated with IDE activity, or impaired insulin signaling, for example, in patients exhibiting metabolic syndrome or diabetes (e.g., Type I or Type II diabetes).

In some embodiments, the in vitro or in vivo methods of inhibiting the activity of IDE comprise contacting an IDE with an IDE inhibitor provided herein in an amount effective to inhibit the activity of the IDE. In some embodiments, an amount of an IDE inhibitor effective to inhibit the activity of IDE comprises an amount that effects a significant decrease, for example, a statistically significant decrease, in IDE activity as compared to IDE activity in the absence of the IDE inhibitor. In some embodiments, an amount of an IDE inhibitor effective to inhibit the activity of IDE comprises an amount that results in an inhibition of IDE activity to less than about 50%, less than about 25%, less than about 20%, less than about 10%, less than about 9%, less than about 8%, less than about 7%, less than about 6%, less than about 5%, less than about 4%, less than about 3%, less than about 2%, less than about 1%, less than about 0.1%, less than about 0.01%, or less than about 0.001% of the IDE activity as compared to the activity in the absence of the compound.

In some embodiments, an IDE inhibitory macrocyclic compound provided herein, for example, 6b, is used to inhibit IDE activity in vivo. In such embodiments, the IDE inhibitor is administered to a subject, for example, in the form of a pharmaceutically acceptable salt or as part of a pharmaceutical composition. In some embodiments, the subject is human. In some embodiments, the subject is an animal, for example, an experimental animal, e.g., an animal model of diabetes. In some embodiments, the animal is a mammal, for example, a rodent (e.g., a mouse, a rat, a hamster), a dog, a cat, a cattle, a goat, a sheep, or a horse.

In some embodiments, an in vivo method of inhibiting IDE is provided that comprises administering an IDE inhibitor provided herein, or a pharmaceutically acceptable composition thereof, to a subject in an amount effective to reduce IDE activity in the subject to less than about 75%, less than about 50%, less than about 25%, less than about 20%, less than about 10%, less than about 9%, less than about 8%, less than about 7%, less than about 6%, less than about 5%, less than about 4%, less than about 3%, less than about 2%, less than about 1%, less than about 0.1%, less than about 0.01%, or less than about 0.001% of the IDE activity as compared to the IDE activity in the absence of the compound.

Other aspects of this invention provide methods of using a macrocyclic IDE inhibitor as described herein in the production of pharmaceutical compositions, or in the manufacture of a medicament, for the reduction of IDE activity. Some aspects of this invention provide methods of using a macrocyclic IDE inhibitor as described herein in the production of a pharmaceutical composition, or in the manufacture of a medicament, for the treatment, prophylaxis, and/or amelioration of a disease or disorder associated with aberrant IDE activity, impaired insulin signaling, or insulin resistance, for example, diabetes, or metabolic syndrome. In some embodiments, the pharmaceutical composition or the medicament is for the treatment, prophylaxis, and/or amelioration of a disease or disorder associated with aberrant IDE activity, impaired insulin signaling, or insulin resistance, for example, diabetes, or metabolic syndrome, wherein the disease or disorder is exhibited by a subject also exhibiting one or more symptoms of Alzheimer's disease. Some aspects of this invention relate to the use of a macrocyclic IDE inhibitor as described herein for the production of pharmaceutical compositions which can be used for treating, preventing, or ameliorating diseases responsive to the inhibition of IDE activity, for example, diabetes or metabolic syndrome.

The amount of a macrocyclic IDE inhibitor as described herein that is required for effective inhibition of IDE in a subject or in vitro, or for the treatment or amelioration of a disease associated with IDE activity will vary from subject to subject, depending on a variety of factors, including, for example, the disorder being treated and the severity of the disorder, or the level of IDE activity in the subject, the activity of the specific macrocyclic IDE inhibitor administered, the specific composition employed; the age, body weight, general health, sex, and diet of the patient; the time of administration, route of administration, and rate of excretion of the specific compound employed; the duration of the treatment; drugs used in combination or coincidental with the specific compound employed; and like factors well known in the medical arts. The macrocyclic IDE inhibitor described herein are preferably formulated in dosage unit form for ease of administration and uniformity of dosage. It will be understood that in some embodiments involving administration of a macrocyclic IDE inhibitor described herein to a human patient, the total daily dose may be determined by the attending physician based on sound medical judgment.

In some embodiments, a macrocyclic IDE inhibitor described herein is formulated into a pharmaceutically acceptable composition comprising the IDE inhibitor, or a pharmaceutically acceptable salt thereof, and optionally a pharmaceutically acceptable carrier. In some embodiments, after formulation with an appropriate pharmaceutically acceptable carrier of a desired dosage, the pharmaceutical composition can be administered to a subject, for example, a human subject via any suitable route, for example, orally, rectally, parenterally, intracisternally, intravaginally, intraperitoneally, topically (as by powders, ointments, or drops), bucally, as an oral or nasal spray, or the like.

In certain embodiments, a macrocyclic IDE inhibitor described herein, for example, in any of Formulae (I)-(XI), is administered to a subject, for example, orally or parenterally, at a dosage level of about 0.001 mg/kg to about 100 mg/kg, from about 0.01 mg/kg to about 50 mg/kg, from about 0.1 mg/kg to about 40 mg/kg, from about 0.5 mg/kg to about 30 mg/kg, from about 0.01 mg/kg to about 10 mg/kg, from about 0.1 mg/kg to about 10 mg/kg, and from about 1 mg/kg to about 25 mg/kg of the subject's body weight per day, one or more times a day, to obtain the desired therapeutic effect or the desired level of IDE inhibition. In some embodiments, the daily dosage is delivered in three separate doses per day, two separate doses per day, or in a single dose per day. In other embodiments, a macrocyclic IDE inhibitor described herein is administered every other day, every third day, every week, every two weeks, every three weeks, or every four weeks. In certain embodiments, the desired dosage is delivered using multiple administrations (e.g., two, three, four, five, six, seven, eight, nine, ten, or more than ten administrations).

Liquid dosage forms of the macrocyclic IDE inhibitor described herein, for example, for oral and parenteral administration include, but are not limited to, pharmaceutically acceptable emulsions, microemulsions, solutions, suspensions, syrups, and elixirs. In addition to the active compounds, the liquid dosage forms may contain inert diluents commonly used in the art, such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents. In certain embodiments for parenteral administration, the compounds of the invention are mixed with solubilizing agents such polyethoxylated castor oil, alcohols, oils, modified oils, glycols, polysorbates, cyclodextrins, polymers, and combinations thereof.

Injectable preparations of the macrocyclic IDE inhibitor described herein, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle. Injectable depot forms are made by forming microencapsule matrices of the drug in biodegradable polymers such as poly(lactide-co-glycolide). Depending upon the ratio of drug to polymer and the nature of the particular polymer employed, the rate of drug release can be controlled. Examples of other biodegradable polymers include poly (orthoesters) and poly(anhydrides). Depot injectable formulations are also prepared by entrapping the drug in liposomes or microemulsions which are compatible with body tissues.

Compositions for rectal or vaginal administration are preferably suppositories which can be prepared by mixing the macrocyclic IDE inhibitor described herein with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, a macrocyclic IDE inhibitor described herein is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets, and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes. Solid compositions of a similar type may also be employed as fillers in soft and hard-filled gelatin capsules using such excipients as lactose or milk sugar as well as high molecular weight polyethylene glycols and the like.

The macrocyclic IDE inhibitor described herein can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active protein may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets, and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

Formulations of the a macrocyclic IDE inhibitor described herein suitable for topical administration include liquid or semi-liquid preparations such as liniments, lotions, gels, applicants, oil-in-water or water-in-oil emulsions such as creams, ointments, or pastes; or solutions or suspensions such as drops. Formulations for topical administration to the skin surface can be prepared by dispersing the drug with a dermatologically acceptable carrier such as a lotion, cream, ointment, or soap. Useful carriers are capable of forming a film or layer over the skin to localize application and inhibit removal. For topical administration to internal tissue surfaces, the agent can be dispersed in a liquid tissue adhesive or other substance known to enhance adsorption to a tissue surface. For example, hydroxypropylcellulose or fibrinogen/thrombin solutions can be used to advantage. Alternatively, tissue-coating solutions such as pectin-containing formulations can be used. Ophthalmic formulation, ear drops, and eye drops are also contemplated as being within the scope of this invention. Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

Additionally, the carrier for a topical formulation can be in the form of a hydroalcoholic system (e.g., liquids and gels), an anhydrous oil or silicone based system, or an emulsion system, including, but not limited to, oil-in-water, water-in-oil, water-in-oil-in-water, and oil-in-water-in-silicone emulsions. The emulsions can cover a broad range of consistencies including thin lotions (which can also be suitable for spray or aerosol delivery), creamy lotions, light creams, heavy creams, and the like. The emulsions can also include microemulsion systems. Other suitable topical carriers include anhydrous solids and semisolids (such as gels and sticks); and aqueous based mousse systems.

It will also be appreciated that the macrocyclic IDE inhibitors described herein and pharmaceutical compositions thereof can be employed in combination therapies, that is, the IDE inhibitors and pharmaceutical compositions provided herein can be administered concurrently with, prior to, or subsequent to, one or more other desired therapeutics or medical procedures. For example, in the context of metabolic syndrome or diabetes, a patient may receive a macrocyclic IDE inhibitor described herein and, additionally, a drug or pharmaceutical composition approved for the treatment of or commonly used to ameliorate a symptom associated with metabolic syndrome or diabetes. Similarly, if an IDE inhibitor or a pharmaceutical composition as provided herein is administered to a subject suffering from another disease, for example, from Alzheimer's Disease, the subject may receive a macrocyclic IDE inhibitor described herein and, additionally, a drug or pharmaceutical composition approved for the treatment of or commonly used to ameliorate a symptom associated with Alzheimer's disease. The particular combination of therapies (therapeutics or procedures) to employ in a combination regimen will take into account compatibility of the desired therapeutics and/or procedures and the desired therapeutic effect to be achieved. It will also be appreciated that the therapies employed may achieve a desired effect for the same disorder (for example, a macrocyclic IDE inhibitor may be administered concurrently with another agent), or they may achieve different effects (e.g., control of any adverse effects).

In still another aspect, the present invention also provides a pharmaceutical pack or kit comprising one or more containers filled with one or more macrocyclic IDE inhibitor described herein, salts thereof, or with a pharmaceutical composition comprising a macrocyclic IDE inhibitor described herein. In certain embodiments, the pack or kit may also include an additional approved therapeutic agent for use as a combination therapy.

Optionally associated with such container(s) can be a notice in the form prescribed by a governmental agency regulating the manufacture, use, or sale of pharmaceutical products, which notice reflects approval by the agency of manufacture, use, or sale for human or veterinary administration.

The function and advantage of these and other embodiments of the present invention will be more fully understood from the Examples below. The following Examples are intended to illustrate the benefits of the present invention and to describe particular embodiments, but are not intended to exemplify the full scope of the invention. Accordingly, it will be understood that the Examples are not meant to limit the scope of the invention.

EXAMPLES

Materials and Methods

General Macrocycle Synthesis:

Macrocycles were synthesized on multi-milligram scale using Fmoc solid-phase peptide synthesis as described in Kleiner et al.[9] Macrocycle cis and trans isomers were purified by preparative HPLC and identified by NMR spectroscopy as described previously.[9]

TABLE 2

Figure 2A:
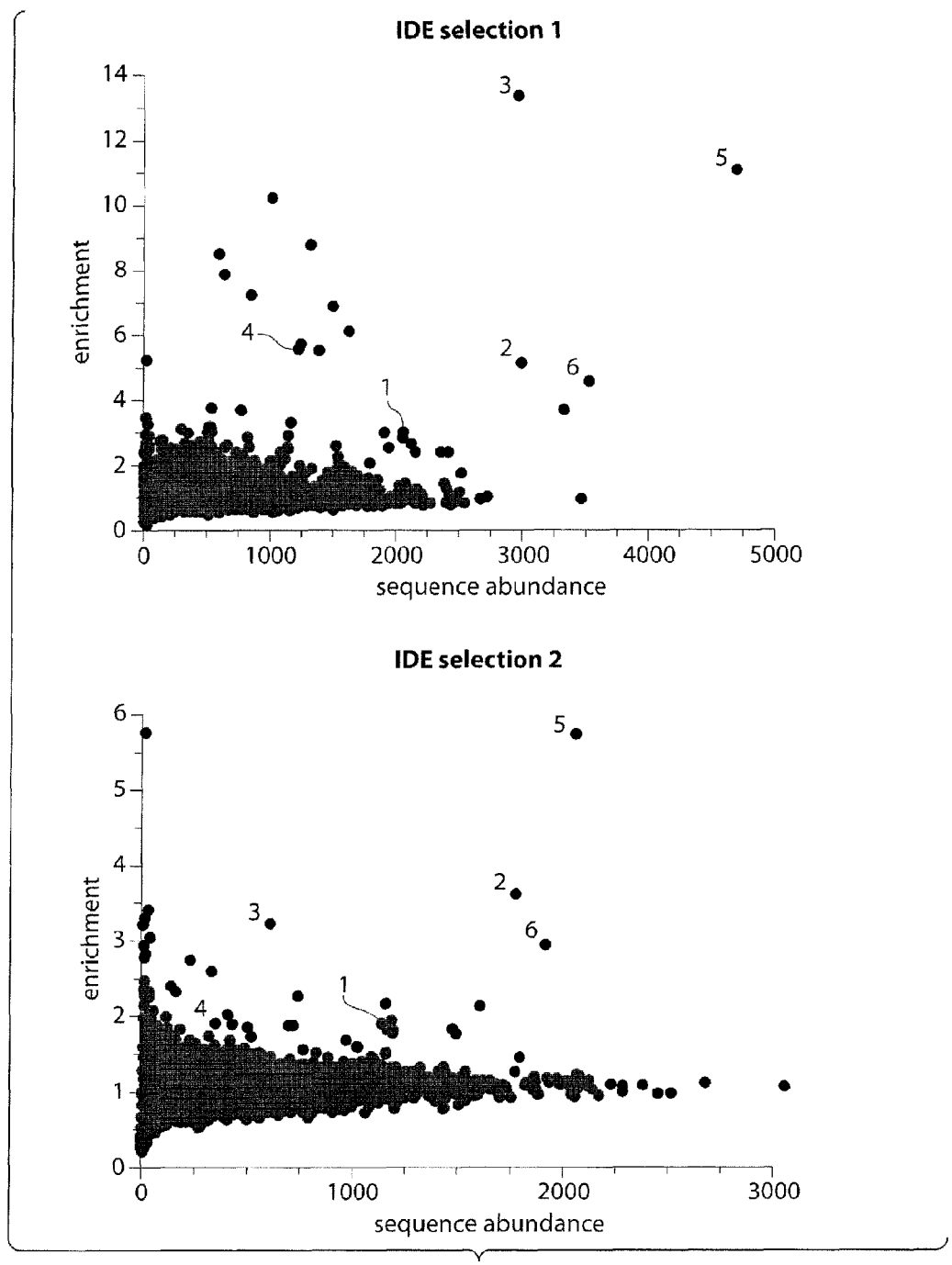
Figures 1, 2B:
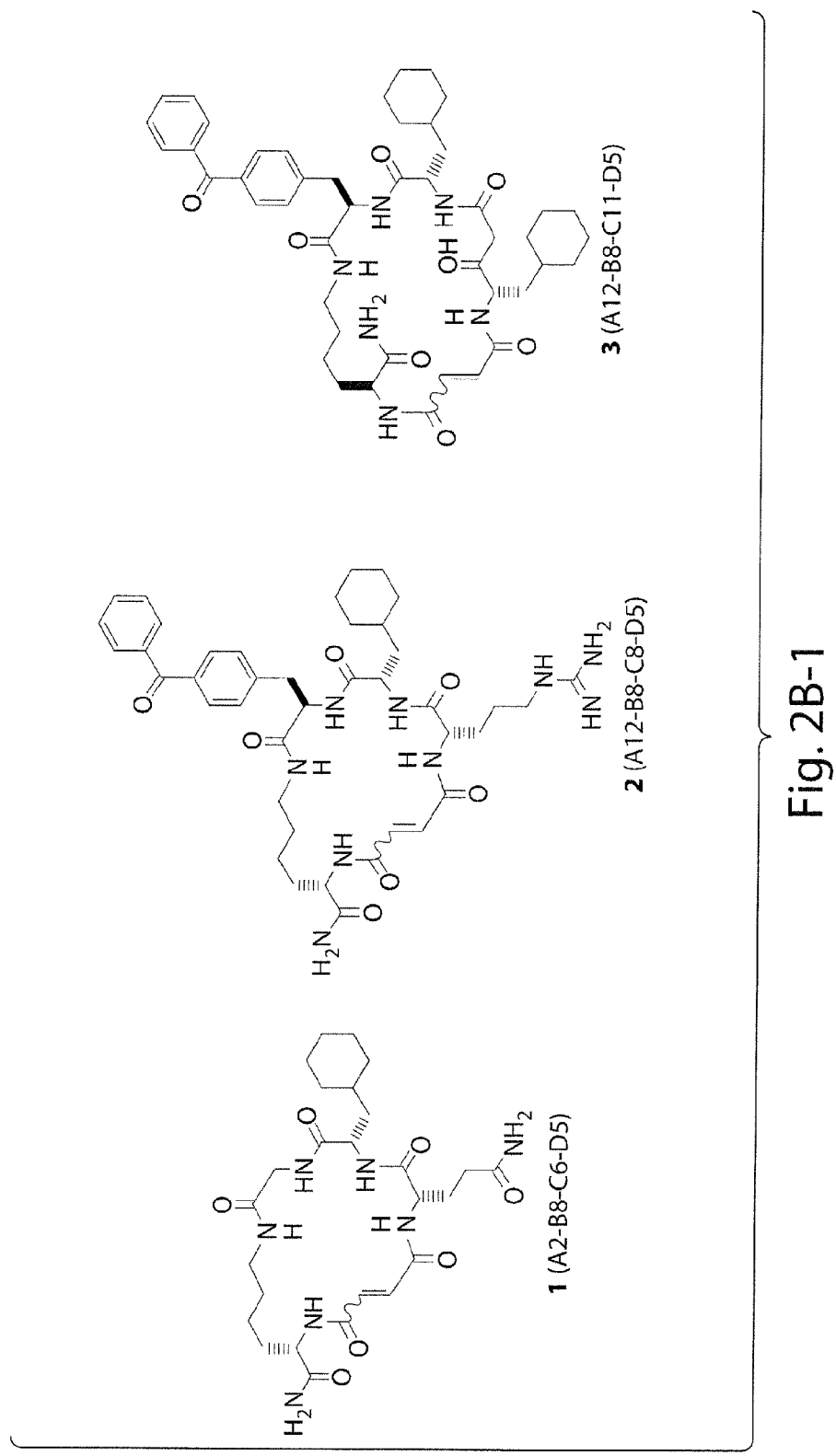
Figures 2, 2B:
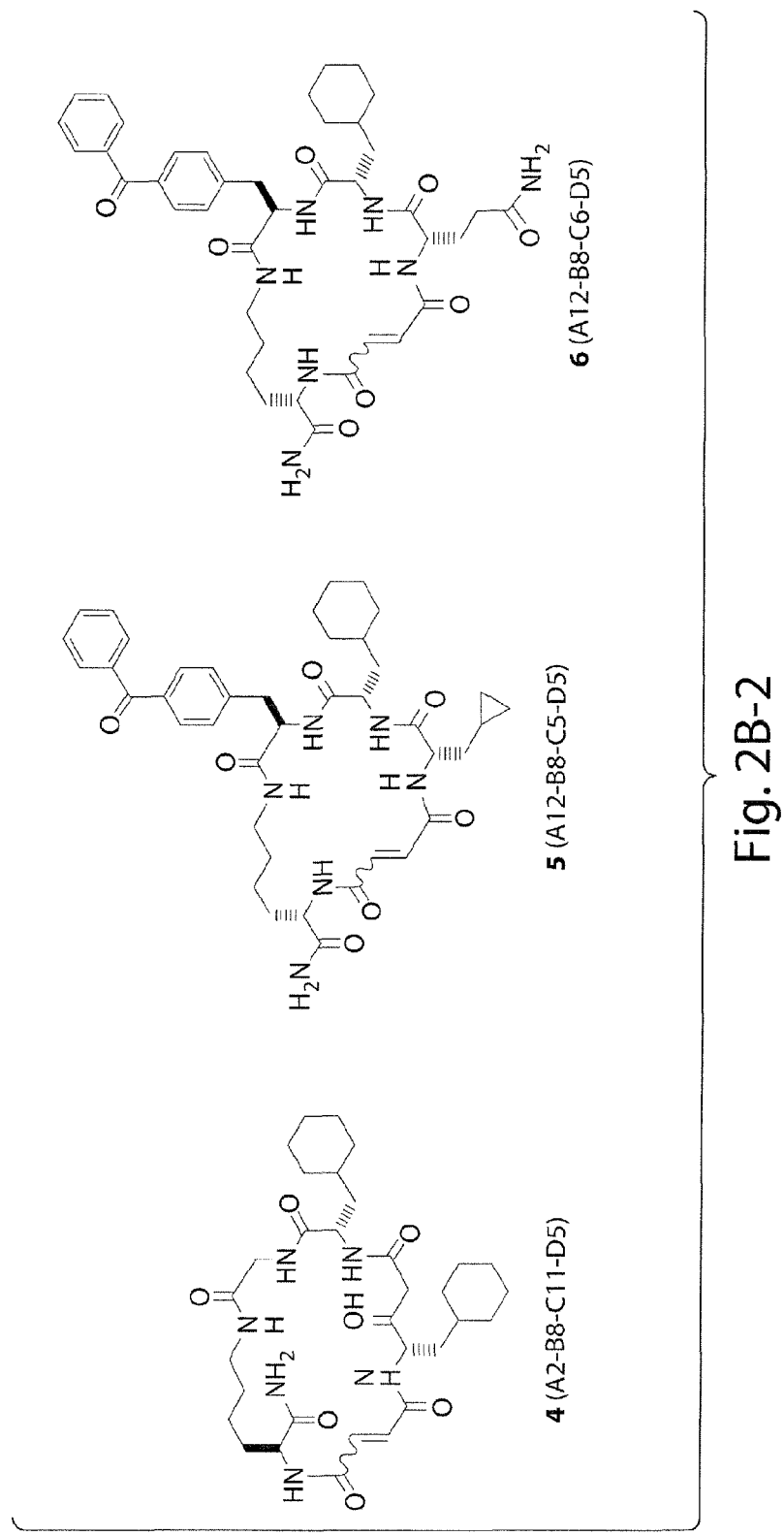

Low-resolution ESI mass spectrometry data of macrocycles described herein in this work (see FIGS. 2 and 3 for macrocycle nomenclature).

| compound | expected (M + H)+ | observed (M + H)+ |
|---|---|---|
| 1 | 564.3 | 564.3 |
| 2 | 786.4 | 786.4 |
| 3a | 827.5 | 827.5 |
| 3b | 827.5 | 827.5 |
| 4a | 633.4 | 633.4 |
| 4b | 633.4 | 633.4 |
| 5a | 741.4 | 741.4 |
| 5b | 741.4 | 741.4 |
| 6a | 758.4 | 758.4 |
| 6b | 758.4 | 758.4 |
| 7 | 654.4 | 654.4 |
| 8 | 730.4 | 730.4 |
| 9 | 752.3 | 752.3 |
| 10 | 676.3 | 676.3 |
| 11 | 701.4 | 701.4 |
| 12 | 701.4 | 701.4 |
| 13 | 715.4 | 715.4 |
| 14 | 687.4 | 687.4 |
| 15 | 630.3 | 630.3 |

TABLE 2-continued

Low-resolution ESI mass spectrometry data of macrocycles described herein in this work (see FIGS. 2 and 3 for macrocycle nomenclature).

| compound | expected (M + H)+ | observed (M + H)+ |
|---|---|---|
| 16 | 758.4 | 758.4 |
| 17 | 744.4 | 744.4 |
| 18 | 786.4 | 786.4 |

In Vitro Selection of DNA-Templated Library:

Selections of the DNA-templated library were performed as described previously.[9] 20 µg of IDE was immobilized on 30 µL of Dynabeads His-Tag Isolation and Pulldown (Invitrogen) magnetic particles according to the manufacturer's instructions. Elution of captured DNA-library members was performed by incubating the protein-loaded particles with 200 mM imidazole. Prior to PCR amplification, imidazole was removed from the eluted samples by gel filtration using Princeton Separations Sephadex minicolumns.

High-Throughput DNA Sequencing:

After selection, eluted DNA-templated library members were PCR amplified with Taq polymerase using the following barcoded primers that appended adaptors required for Illumina sequencing:

IlluminaLong:
(SEQ ID NO: 4)
5'-AATGATACGGCGACCACCGAGATCTACACTCTTTCCCTACACGA
CGCTCTTCCGATCTXXXXXXXCCCTGTACAC-3'

IlluminaShort:
(SEQ ID NO: 5)
5'-CAAGCAGAAGACGGCATACGAGCTCTTCCGATCTGAGTGGGAT
G-3'

After PCR amplification, PCR amplicons were gel-purified by agarose gel electrophoresis and quantified using qPCR and the Picogreen assay (Invitrogen) prior to submitting them for Illumina sequencing at the FAS Center for Systems Biology. Selection results were analyzed as described previously.[9]

Biodistribution Assay:

Macrocycles were diluted to 0.1 mg/mL or 1 mg/mL in PBS and IP-injected into a mouse to produce a concentration of 1 mg/kg or 10 mg/kg, respectively. After 45 minutes, organs were harvested, and the small-molecule fractions were extracted into a 2:1:1 mixture of chloroform:methanol:water. Samples were evaporated under a stream of nitrogen, resuspended in 100 µL of chloroform and subjected to LC-MS analysis.

In Vitro Protease Assays:

Protease assays with IDE and neprilysin were performed using Mca-RPPGFSAFK(Dnp)-OH substrate peptide (R&D Systems, SEQ ID NO: 6) and purified recombinant human IDE and recombinant human neprilysin (R&D Systems) according to the manufacturer's instructions. For IDE, 2 µL of small molecule dissolved in DMSO was combined with 48 µL 0.2 µg/mL IDE in IDE assay buffer (50 mM Tris, 1 M NaCl, pH 7.5). 50 µL of 20 µM substrate peptide in IDE assay buffer was then added to initiate the reaction, and peptide cleavage was monitored on a fluorescent plate reader (excitation=320 nM; emission=405 nM) for 5 minutes. The above protocol was also used for assaying neprilysin activity, substituting the neprilysin assay buffer (50 mM Tris, 0.05% Brij-35, pH 9.0).

Protease assays with THOP1 and NLN were performed using MCA-Pro-Leu-Gly-Pro-D-Lys(DNP)-OH (Bachem, SEQ ID NO: 7) and purified recombinant human THOP1 and NLN (R&D Systems) according to the manufacturer's instructions.

Trypsin activity was measured using the Z-Arg-AMC substrate (Bachem). 93 µL of 200 nM trypsin in PBS were incubated with 2 µL of compound dissolved in DMSO. 5 µL of Z-Arg-AMC substrate in DMSO were then added to initiate the reaction. Substrate cleavage was monitored on a fluorescent plate reader (excitation=383 nM; emission=455 nM) for 10 minutes.

In Vitro Selection of 13,824 Small-Molecule Macrocycles Against IDE

Insulin-degrading enzyme (IDE) protein was obtained in its purified form with a poly-histidine tag and immobilized on magnetic particles coated with cobalt. After incubation with the DNA-templated library, non-binding library members were washed away with buffer, and protein-library member complexes were eluted from resin with imidazole (FIG. 1). DNA-templated library members enriched after target selection were PCR amplified with target-specific barcoded primers that appended adaptors required for Illumina high-throughput DNA sequencing. We performed two independent selection replicates with IDE and three independent selections against empty resin as negative control selections. These five barcoded selection PCR amplicons were pooled in equimolar quantities and submitted for Illumina high-throughput DNA sequencing. High-throughput sequencing yielded 19 million sequence reads—an average of ~3.8 million sequence reads per selection. Variation in library member abundance that was a result of binding to the target protein was revealed by calculating fold enrichment and plotting the enrichments as a function of post-selection library member abundance as described previously.[9]

In Vitro Selection Reveals a Family of IDE-Inhibiting Macrocycles

After one round of in vitro selection, we identified DNA sequences corresponding to macrocycles A12-B8-C11-D5 (3), A12-B8-C5-D5 (5), A12-B8-C6-D5 (6) and A12-B8-C8-D5 (2) enriched between 4- to 14-fold against IDE (FIG. 2a, IDE selection 1); these same macrocycles were also enriched 3- to 6-fold in a replicate IDE selection (FIG. 2a, IDE selection 2). The strong and reproducible enrichment factors, high degree of structural similarity among these molecules (FIG. 2a), and the lack of enrichment of these macrocycles in other protease selections we performed, collectively suggested that these molecules are authentic IDE ligands.

We synthesized six molecules (FIG. 2b) from the IDE selection—the four strongly enriched macrocycles described above (2, 3, 5, and 6) and two related macrocycles (1 and 4) possessing glycine (building block "A2") at the "A" position, which were less strongly enriched (FIG. 2a). Compounds were synthesized as described previously;[9] in most cases the macrocycle synthesis yielded two isomers corresponding to the cis and trans olefins generated after macrocyclization. Macrocycles were assayed for IDE inhibition by monitoring cleavage of a substrate peptide[13] containing a fluorophore-quencher pair such that cleavage of the model substrate results in increased fluorescence. Although our selection did not explicitly select for inhibition (only binding is required for enrichment), all four strongly enriched macrocycles inhibited IDE activity with $IC_{50} \leq 10$ µM (FIG. 3, upper panel; Table 1). The most potent macrocycle, trans-A12-B8-C6-D5 (6b), inhibited IDE with an $IC_{50}$ of 140 nM. The three-dimensional conformation adopted by these compounds appears to be important to their inhibitory activity, as the trans-olefin isomers of macrocycles 3, 5, and 6 exhibit >10-fold stronger potency than the corresponding cis-olefin macrocycle isomers (Table 1). Compounds 1 and 4, which contained glycine (A2) instead of D-benzoylphenylalanine (A12) at the "A" position were inactive against IDE (Table 1).

TABLE 1

$IC_{50}$ values for enriched macrocycles against IDE. IDE activity was measured using a fluorophore-quencher model peptide as described herein.

| Compound | IDE $IC_{50}$ (µM) |
| --- | --- |
| 1 (cis olefin) | >100 |
| 2 (cis olefin) | 10 |
| 3a (cis olefin) | >20 |
| 3b (trans olefin) | 1.5 |
| 4a (cis olefin) | >100 |
| 4b (trans olefin) | >100 |
| 5a (cis olefin) | >20 |
| 5b (trans olefin) | 1.0 |
| 6a (cis olefin) | 5.6 |
| 6b (trans olefin) | 0.06 |

Structure-Activity Relationship for Macrocyclic IDE Inhibitors

We probed the molecular determinants of macrocycle-IDE inhibition by synthesizing a series of 6b derivatives. We systematically investigated single amino acid changes at each of the three building block positions, as well as modifications to the scaffold amino acid. Substitutions at the "A" position, replacing D-benzoylphenylalanine with D-phenylalanine or D-4-phenyl-phenylalanine completely abolished activity of the resulting compound against IDE (FIG. 3, lower panel). Similarly, replacing cyclohexylalanine at the "B" position with alanine resulted in an inactive macrocycle. Substituting phenylalanine at the "B" position produced a ~40-fold less potent compound. These results indicate that a simple hydrophobic residue at the "A" position is not sufficient for potent IDE inhibition. At the "B" position, it appears that hydrophobic interactions dominate. Derivatives of 6b modified at the "C" position retained most of their activity against IDE. Surprisingly, substitution of alanine at this position gave a similarly potent macrocycle. Replacement of glutamine with 2-methylalanine or glycine resulted in only modest (2-4-fold) losses in potency.

Figure 4:
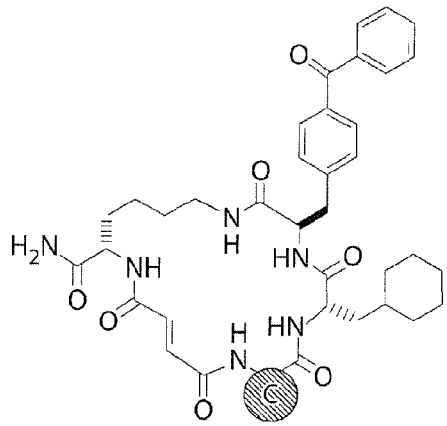
FIG. 4. Yonetani-Theorell double inhibition plot.

Completely removing the residue (15) or replacing glutamine with an amino acid of the opposite stereochemistry (12), however, produced substantial decreases in activity (FIG. 4). Given these trends, it is unlikely that macrocycle 6b is making critical interactions to IDE through its "C" building block, although the building block does appear to influence the overall conformation of the compound.

We also investigated modifications to the scaffold amino acid (the "D" position). Not surprisingly, appending an ethyl group (18) at the site of DNA linkage had no effect on inhibitor potency. More substantial modifications such as removing a methylene (17) or changing the stereochemistry of the scaffold amino acid (16) resulted in a ~30-50-fold decrease in potency. Collectively, these results indicate the importance of the "A" and "B" side chains, benzophenone and cyclohexane, respectively, and the overall scaffold. There appears to be less preference for a particular side chain (although an amino acid of L stereochemistry is preferred) at the "C" position or at the site of DNA-linkage.

The lack of obvious structural relationship between 6b and known IDE substrates, together with its excellent selectivity profile, raised the possibility that 6b may inhibit IDE by binding an allosteric site, rather than the active site. To test this possibility, we assayed IDE in vitro in the presence of varying concentrations of both 6b and Ii1. Since Ii1 is known to bind the active site of IDE,[48] the ability of 6b to inhibit IDE in a manner that is synergistic, rather than competitive, with Ii1 suggests that the 6b binding site includes residues beyond the active site of IDE. Indeed, a Yonetani-Theorell double inhibition plot indicates that the binding sites of Ii1 and 6b are distinct (FIG. 4), further suggesting that 6b may indeed bind to an allosteric site in IDE, thereby explaining its unusual selectivity.

Specificity of Macrocyclic IDE Inhibitors

Figures 3, 4, 5:
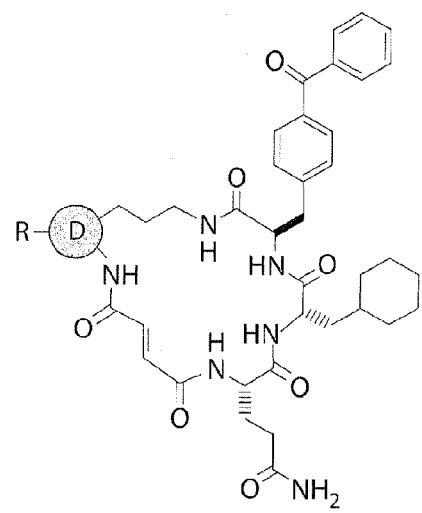
FIG. 5. Protease inhibition using macrocycle 6b assayed against IDE, THOP1, NLN, neprilysin, and trypsin (upper panel) and comparison of the protease inhibition specificity of compound 6b and Ii1 (lower panel).
Figure 4:
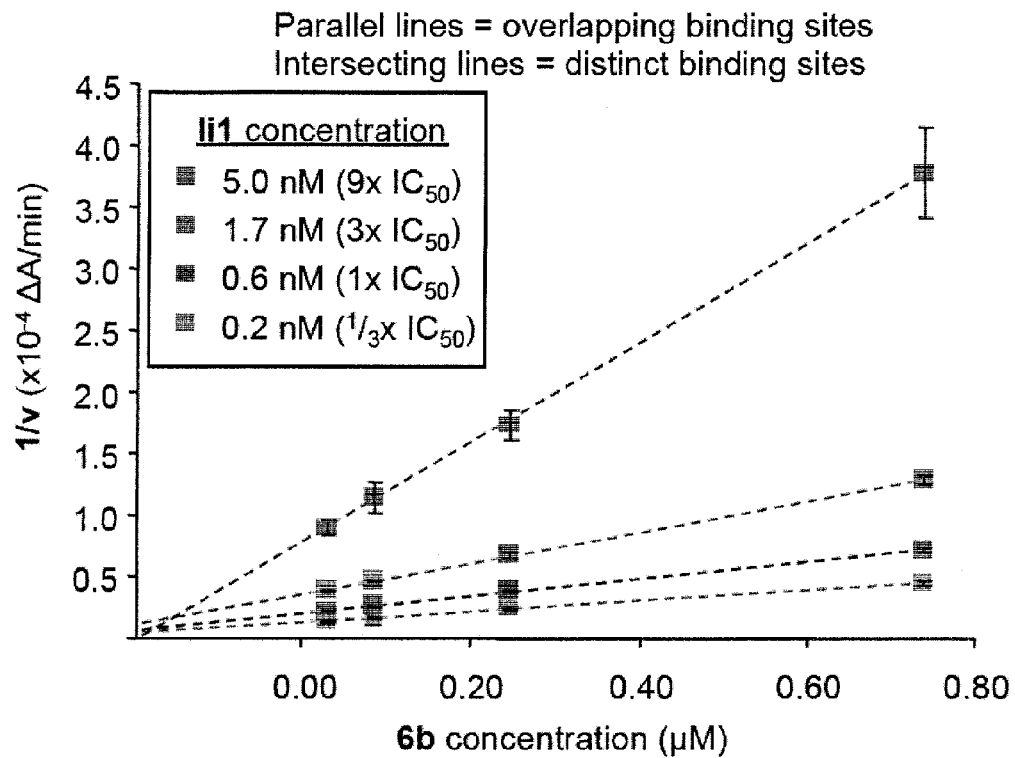
Figure 5:
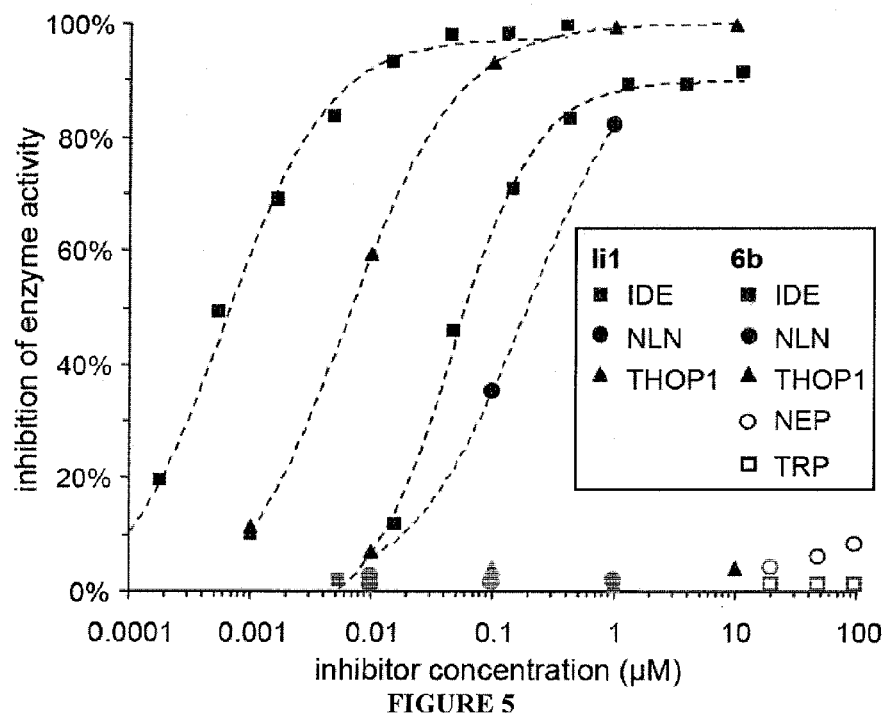
Figure 6:
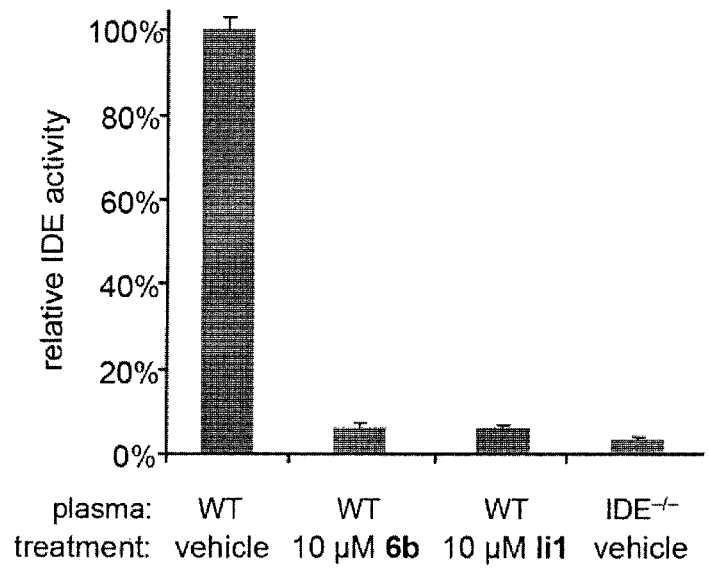
FIG. 6. Cleavage of an IDE-selective endogenous peptide substrate (ISEPS) in murine plasma ex vivo in the absence and presence of macrocycle 6b.

To determine whether the isolated macrocycles displayed any target specificity, we assayed macrocycle 6b inhibitory activity against the related zinc-metalloproteases neurolysin (NLN), thimet oligopeptidase (THOP1), and neprilysin (NEP), as well as against the unrelated serine-protease trypsin. Macrocycle, 6b, failed to demonstrate any significant inhibition of these proteases even when assayed at 100 μM (~1,000-times higher than the measured IDE $IC_{50}$) (FIG. 5, upper panel). Slight activation of THOP1 and NLN was observed at higher concentrations. Importantly, when these protease specificity assays were repeated on Ii1 (Inhibitor of IDE 1), a substrate peptide mimetic that is the only previously reported IDE inhibitor ($IC_{50}$=0.6 nM), Ii1 was found to inhibit THOP1 and NLN potently (IC50=6 nM and 150 nM, respectively) (FIG. 5, lower panel), consistent with the known metalloprotease promiscuity of hydroxamates. Taken together these results suggest that 6b is the most selective IDE inhibitor discovered to date.

Figure 7:
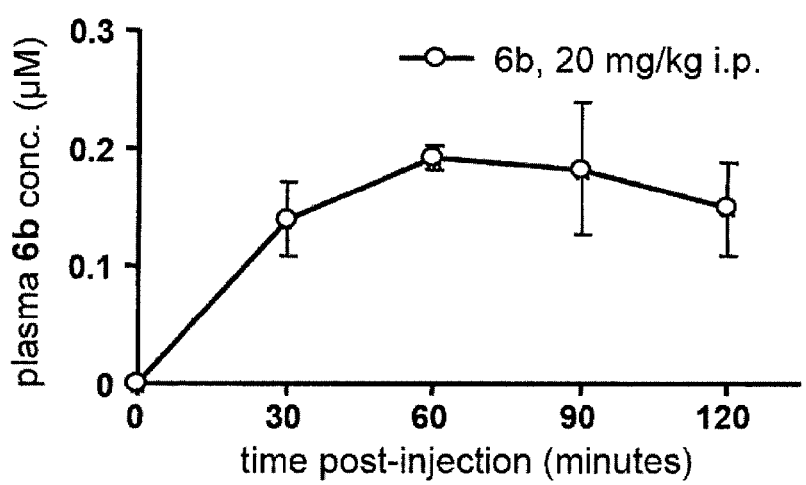
FIG. 7. Plasma concentration of macrocycle 6b at different time points after intraperitoneal injection of 20 mg/kg into mice.

In Vivo Stability, In Vivo Biodistribution, and In Vivo Activity of IDE Inhibitors An LC-MS assay was developed to accurately quantitate 6b and Ii1 in plasma by establishing standard curves that enable the detection of as little as 30 fmoles of both compounds. Macrocyclic peptidomimetics are in general not recognized by proteases, and can exhibit in vivo stability several orders of magnitude higher than a corresponding linear peptide. In preliminary pharmacokinetic experiments, mice were injected intraperitoneally (i.p.) with 20 mg/kg 6b (n=2) in 18:1:1 saline:DMSO:Tween-80. The injections were well tolerated and resulted in a peak blood concentration of 0.2 μM 6b after 60 minutes (FIG. 7).

Figure 8A:
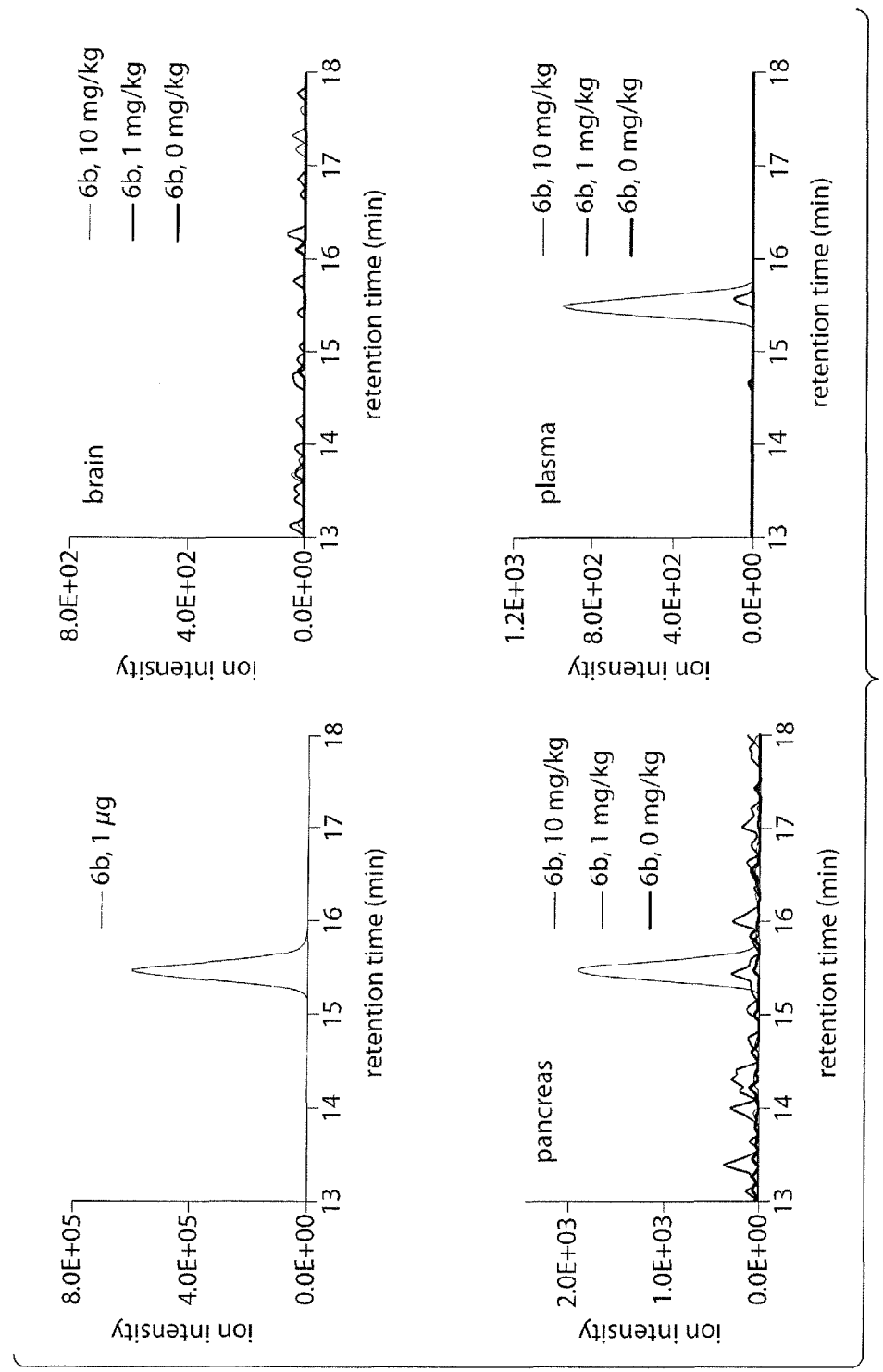
FIG. 8. Biodistribution of macrocycles 6b, 11, and 18 in a mouse. (a) LC-MS analysis of 6b present in brain, pancreas, and plasma after IP injection. (b) LC-MS analysis of 11 present in brain, pancreas, and plasma after IP injection. (c) LC-MS quantification of 18 in brain, pancreas, and plasma after IP injection.
Figure 8B:
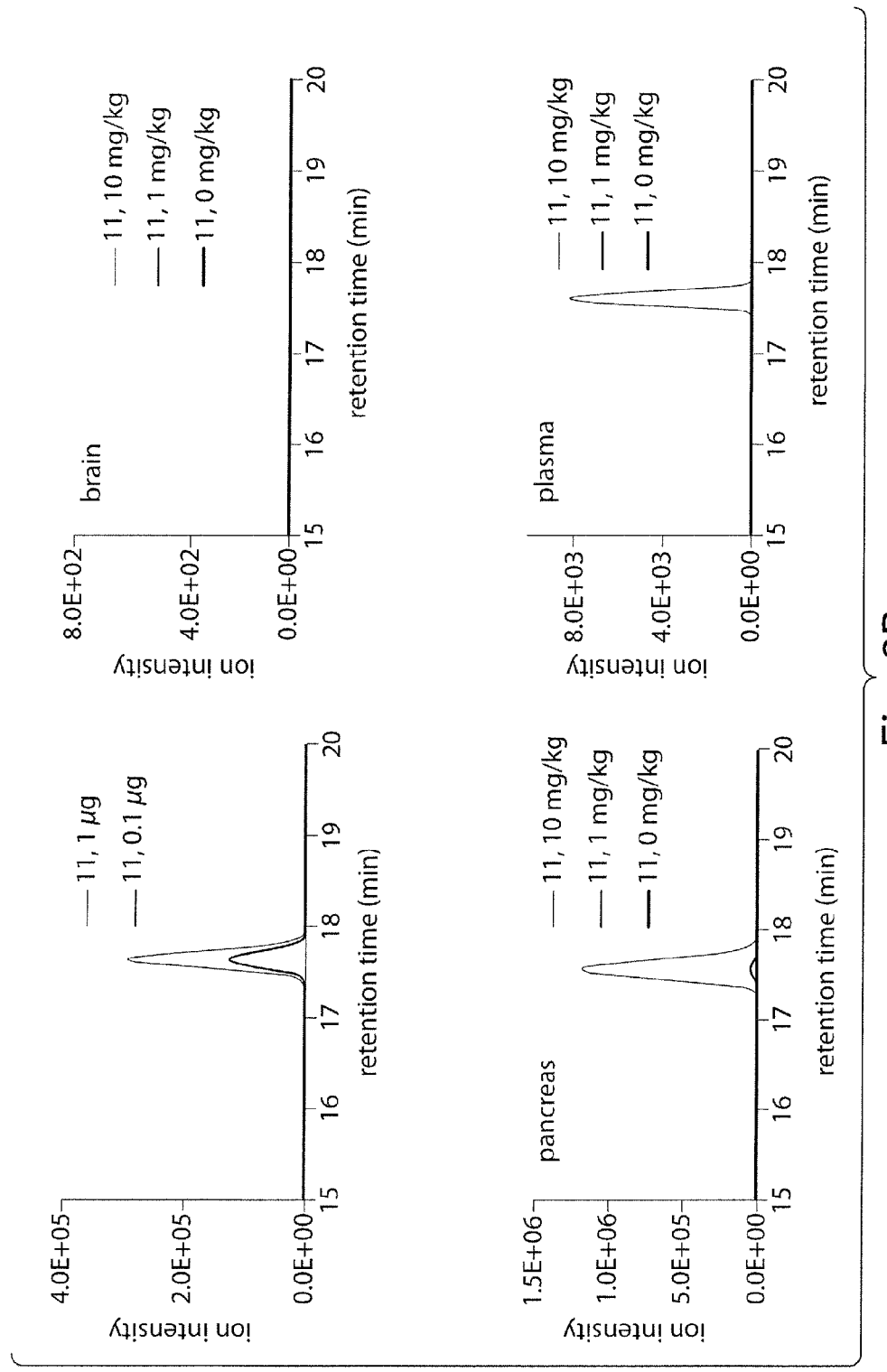
Figure 8C:
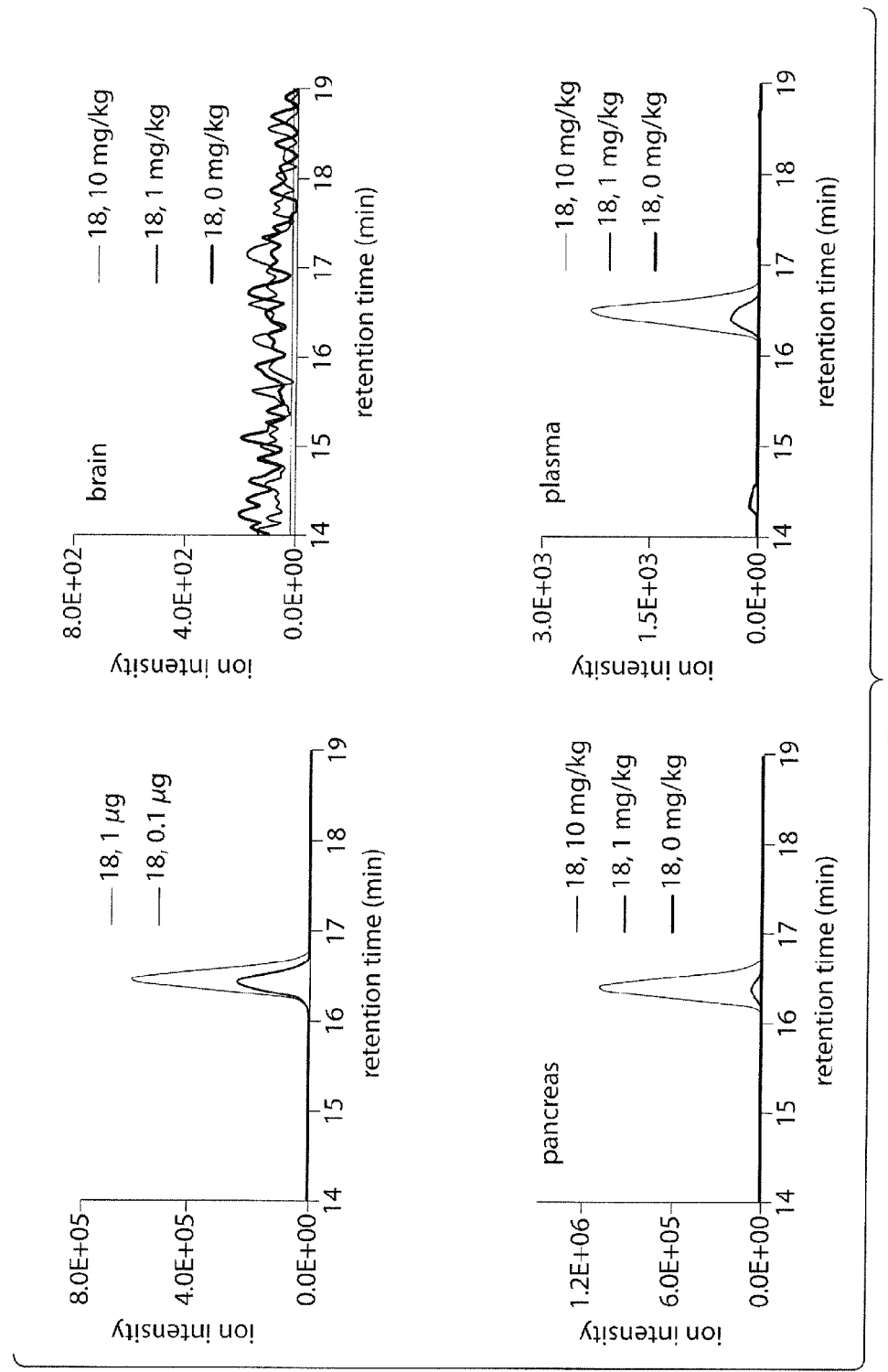

The tissue distribution of enriched macrocycles after i.p. injection was examined. In order to establish that macrocyclic compounds can be delivered to relevant sites of IDE inhibition, we analyzed the biodistribution of our most potent IDE inhibitors, 6b, 11, and 18. Briefly, compounds were injected at different concentrations intraperitoneally into mice, and plasma, brain, and pancreas were harvested after 45 minutes. Vehicle-only injections were performed as negative controls. We determined the relative amount of macrocycle present by extracting the organs with organic solvents and quantifying the amount of compound present by LC-MS analysis. After intraperitoneal injection, none of the three compounds could be detected in the brain (FIG. 8). While blood-brain-barrier-permeable IDE inhibitors may be useful as biological probes, studies have called into question the wisdom of inhibiting IDE in this organ due to its ability to degrade the Alzheimer-related amyloid-beta peptide.[2] In contrast, all three compounds could be detected in plasma and in the pancreas. Macrocycle concentrations in the plasma were comparable for all three compounds. Interestingly, the more hydrophobic compounds 11 and 18 (FIG. 8b and FIG. 8c) showed much higher levels (100-1000-fold greater) in the pancreas than the parent 6b molecule (FIG. 8a), indicating either localization of these compounds to the pancreas, or a reduced ability of 6b to distribute into this region.

These results are significant because they suggest that the investigated macrocycles do not inhibit IDE in the brain, where IDE inhibition is thought to promote amyloid formation and Alzheimer's disease. Moreover, the ability of the macrocycles to inhibit IDE in tissues (plasma and pancreas) in which insulin regulation is important for glucose tolerance, but not in other tissues in which IDE inhibition may be deleterious, highlights a major advantage of small molecule inhibition compared with genetic approaches. In contrast, Ii1 was not detected in blood 30 min after 1 mg/kg injection i.p., consistent with previous indications that Ii1 is not sufficiently stable under physiological conditions for use in vivo.

Figure 9:
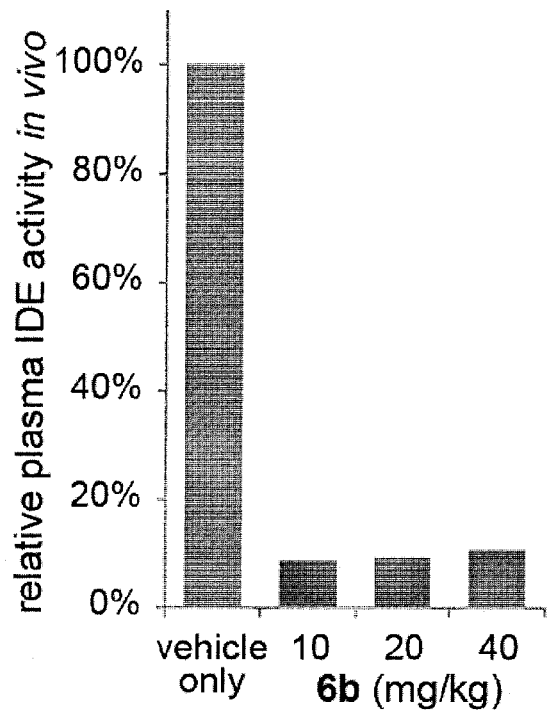
FIG. 9. IDE activity in mice injected with vehicle alone and with 10 mg/kg, 20 mg/kg, or 40 mg/kg 6b.

Finally, we compared plasma IDE activity in mice injected with 6b with plasma IDE activity in control mice injected with vehicle alone (18:1:1, saline:DMSO:Tween-80). Plasma IDE activity 60 min after 10 mg/kg, 20 mg/kg, or 40 mg/kg i.p. injection of 6b was inhibited by ≥90% (FIG. 9). These results indicate that macrocycle 6b is able to substantially inhibit IDE activity in vivo.

CONCLUSION

Figure 10:
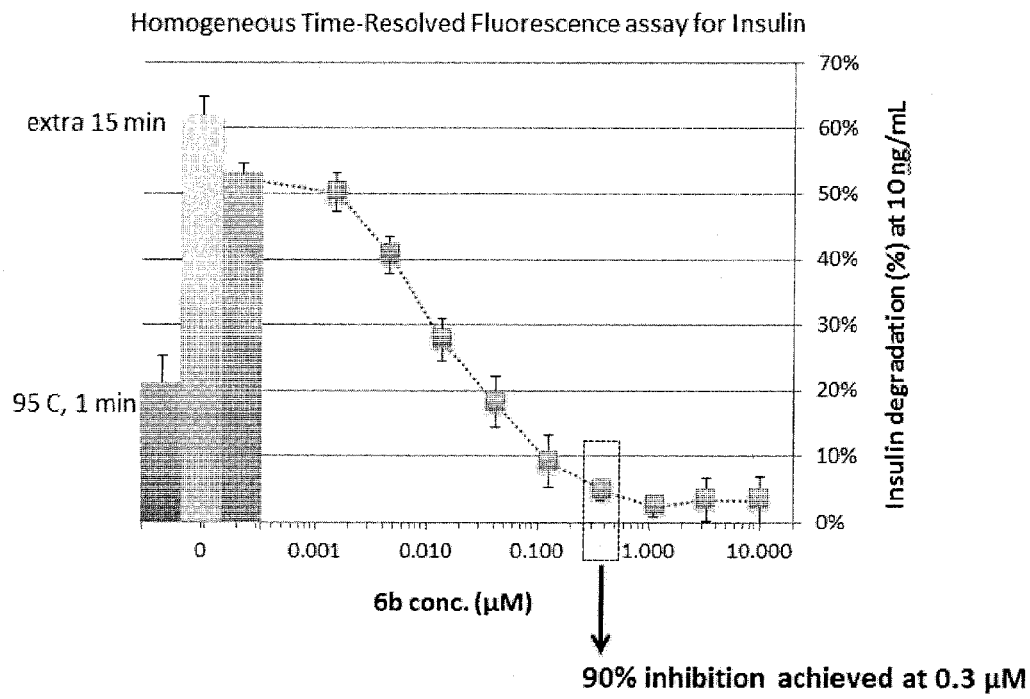
FIG. 10. Inhibition of insulin degradation by IDE in vitro. Incubation: 37° C. for 30 min, insulin at 10 ng/mL=1.7 nM (Km=70 nM).
Figure 11:
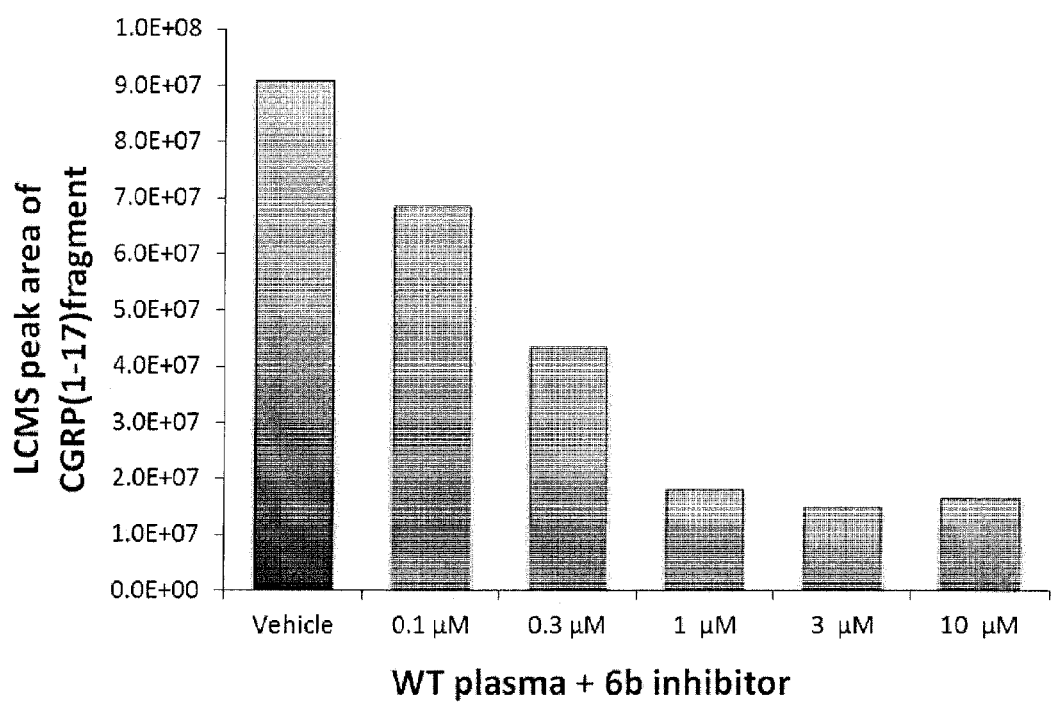
FIG. 11. Inhibition of CGRP degradation by IDE ex vivo in plasma.
Figure 12:
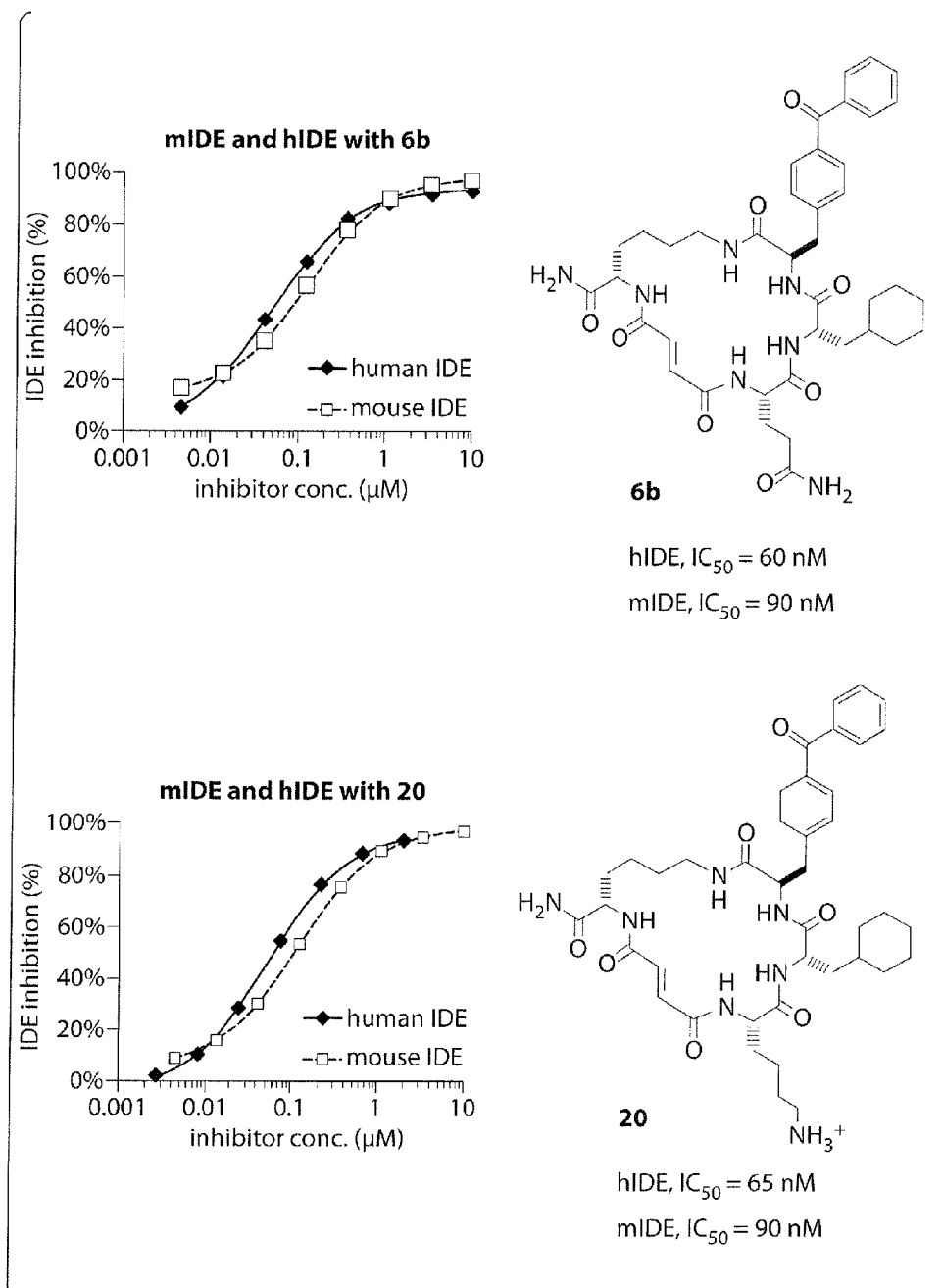
FIG. 12. Similar potency of 6b and 6bK against human and murine IDE.

In vitro selection of a DNA-templated macrocycle library led to the identification of a potent and selective scaffold for IDE inhibition. The discovered IDE-inhibitors display robust structure-activity-relationship (SAR) with potencies as good as 50 nM in vivo or in vitro. Some of the IDE inhibitors disclosed herein are able to achieve >90% IDE inhibition at a concentration of ~1 μM in plasma or in vitro (see, e.g., insulin and CGRP degradation data in FIGS. 10 and 11.). The IDE inhibitors provided herein include water soluble equipotent analogs, (e.g., 20, see FIG. 12, which are highly soluble in water or saline (e.g., up to <0.1M). The inhibitors provided herein display selectivity for IDE over related and unrelated proteases and are able to distribute into the pancreas, but not the brain, after intraperitoneal injection.

REFERENCES

1. Duckworth, W. C., Bennet, R. G. & Hamel, F. G. Insulin degradation: progress and potential. Endocr. Rev. 19, 608-624 (1998).
2. Farris, W. et al. Insulin-degrading enzyme regulates the levels of insulin, amyloid beta-protein, and the beta-amyloid precursor protein intracellular domain in vivo. Proc Natl Acad Sci USA 100, 4162-4167 (2003).
3. Mirsky, I. A. & Broth-Kahn, R. H. The inactivation of insulin by tissue extracts. I. The distribution and properties of insulin inactivating extracts (insulinase). Arch. Biochem. 20, 1-9 (1949).
4. Leissring, M. A. et al. Designed Inhibitors of Insulin-Degrading Enzyme Regulate the Catabolism and Activity of Insulin. PLOS One 5, 1-13 (2010).
5. Shen, Y., Joachimiak, A., Rosner, M. R. & Tang, W. Structures of human insulin-degrading enzyme reveal a new substrate recognition mechanism. Nature 443, 870-874 (2006).
6. Kwon, Y. & Kodadek, T. Quantitative Comparison of the Relative Cell Permeability of Cyclic and Linear Peptides. Chem Biol 14, 671-677 (2007).
7. Becker, A. B. & Roth, R. A. Insulysin and pitrilysin: insulin-degrading enzymes of mammals and bacteria. Methods Enzymol 248, 693-703 (1995).
8. Driggers, E. M., Hale, S. P., Lee, J. & Terrett, N. K. The exploration of macrocycles for drug discovery—an underexploited structural class. Nat. Rev. Drug Discovery 7, 608-624 (2008).
9. Kleiner, R. E., Dumelin, C. E., Tiu, G. C., Sakurai, K. & Liu, D. R. In Vitro Selection of a DNA-Templated Macrocycle Library Reveals a Class of Macrocyclic Kinase Inhibitors. J. Am. Chem. Soc. 132, 11779-11791 (2010).
10. Patick, A. K. & Potts, K. E. Protease Inhibitors as Antiviral Agents. Clin Microbial Rev 11, 614-627 (1998).
11. Maresso, A. & Schneewind, O. Sortase as a Target of Anti-Infective Therapy. Pharmacol Rev 60, 128-141 (2008).

12. Martens, K. et al. PREPL: a putative novel oligopeptidase propelled into the limelight. Biol Chem 387, 879-883 (2006).
13. Johnson, G. D. & Ahn, K. Development of an Internally Quenched Fluorescent Substrate Selective for Endothelin-Converting Enzyme-1. Anal. Biochem. 286, 112-118 (2000).

All publications, patents and sequence database entries mentioned herein, including those items listed above, are hereby incorporated by reference in their entirety as if each individual publication or patent was specifically and individually indicated to be incorporated by reference. In case of conflict, the present application, including any definitions herein, will control.

EQUIVALENTS AND SCOPE

Those skilled in the art will recognize, or be able to ascertain using no more than routine experimentation, many equivalents to the specific embodiments of the invention described herein. The scope of the present invention is not intended to be limited to the above description, but rather is as set forth in the appended claims.

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention also includes embodiments in which more than one, or all of the group members are present in, employed in, or otherwise relevant to a given product or process.

Furthermore, it is to be understood that the invention encompasses all variations, combinations, and permutations in which one or more limitations, elements, clauses, descriptive terms, etc., from one or more of the claims or from relevant portions of the description is introduced into another claim. For example, any claim that is dependent on another claim can be modified to include one or more limitations found in any other claim that is dependent on the same base claim. Furthermore, where the claims recite a composition, it is to be understood that methods of using the composition for any of the purposes disclosed herein are included, and methods of making the composition according to any of the methods of making disclosed herein or other methods known in the art are included, unless otherwise indicated or unless it would be evident to one of ordinary skill in the art that a contradiction or inconsistency would arise.

Where elements are presented as lists, e.g., in Markush group format, it is to be understood that each subgroup of the elements is also disclosed, and any element(s) can be removed from the group. It is also noted that the term "comprising" is intended to be open and permits the inclusion of additional elements or steps. It should be understood that, in general, where the invention, or aspects of the invention, is/are referred to as comprising particular elements, features, steps, etc., certain embodiments of the invention or aspects of the invention consist, or consist essentially of, such elements, features, steps, etc. For purposes of simplicity those embodiments have not been specifically set forth in haec verba herein. Thus for each embodiment of the invention that comprises one or more elements, features, steps, etc., the invention also provides embodiments that consist or consist essentially of those elements, features, steps, etc.

Where ranges are given, endpoints are included. Furthermore, it is to be understood that unless otherwise indicated or otherwise evident from the context and/or the understanding of one of ordinary skill in the art, values that are expressed as ranges can assume any specific value within the stated ranges in different embodiments of the invention, to the tenth of the unit of the lower limit of the range, unless the context clearly dictates otherwise. It is also to be understood that unless otherwise indicated or otherwise evident from the context and/or the understanding of one of ordinary skill in the art, values expressed as ranges can assume any subrange within the given range, wherein the endpoints of the subrange are expressed to the same degree of accuracy as the tenth of the unit of the lower limit of the range.

In addition, it is to be understood that any particular embodiment of the present invention may be explicitly excluded from any one or more of the claims. Where ranges are given, any value within the range may explicitly be excluded from any one or more of the claims. Any embodiment, element, feature, application, or aspect of the compositions and/or methods of the invention, can be excluded from any one or more claims. For purposes of brevity, all of the embodiments in which one or more elements, features, purposes, or aspects is excluded are not set forth explicitly herein.

What is claimed is:
1. A compound of Formula (V):

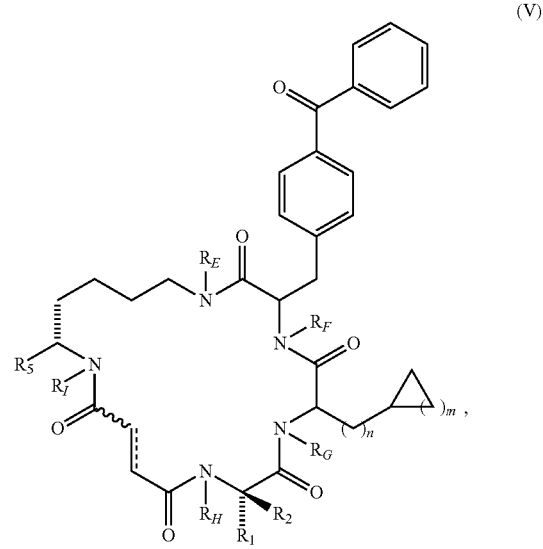

or a pharmaceutically acceptable salt, solvate, hydrate, stereoisomer, polymorph, tautomer, or isotopically enriched form thereof,
wherein:
===== is a single or double C—C bond, wherein when ===== is a double C—C bond, then ⁓⁓⁓ indicates that the adjacent C=C double bond is in a cis or trans configuration;
$R_1$ is —CH$_2$CH$_2$CH$_2$CH$_2$—NH$_2$;
$R_2$ is hydrogen; halogen; substituted or unsubstituted aliphatic; or substituted or unsubstituted heteroaliphatic;
$R_5$ is substituted or unsubstituted aliphatic; substituted or unsubstituted heteroaliphatic; substituted or unsubstituted aryl; substituted or unsubstituted heteroaryl; substituted or unsubstituted amino; —C(=O)—N(R$_J$)$_2$; —C(=O)—OR$_J$; —C(=O)—SR$_J$; or —CH$_2$—C(=O)N(R$_J$)$_2$, wherein each occurrence of R$_J$ is independently hydrogen; a protecting group; substituted or unsubstituted aliphatic; substituted or unsubstituted heteroaliphatic; substituted or unsubstituted acyl; substituted or unsubstituted aryl; or substituted or unsubstituted heteroaryl; or two $R_J$ groups are joined to form a substituted or unsubstituted heterocyclic group;

each instance of $R_E$, $R_F$, $R_G$, $R_H$, and $R_I$ is independently hydrogen; a nitrogen protecting group; substituted or unsubstituted aliphatic; or substituted or unsubstituted heteroaliphatic;

n is 0 or an integer between 1 and 10, inclusive; and m is an integer between 1 and 5, inclusive.

2. The compound of claim 1, wherein the compound is of Formula (VI):

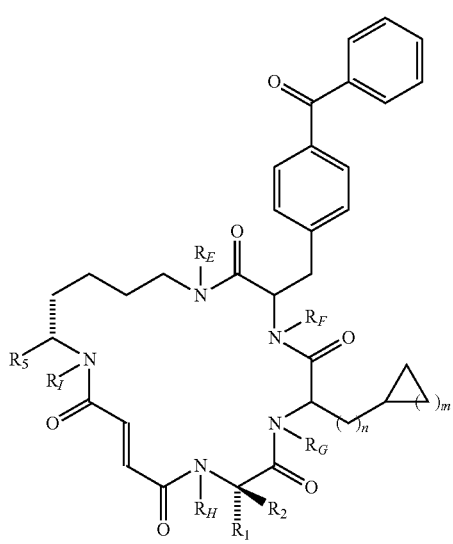

or a pharmaceutically acceptable salt, solvate, hydrate, stereoisomer, polymorph, tautomer, or isotopically enriched form thereof.

3. The compound of claim 1, wherein n is 1.

4. The compound of claim 1, wherein m is 4.

5. The compound of claim 1, wherein the compound is of Formula (H):

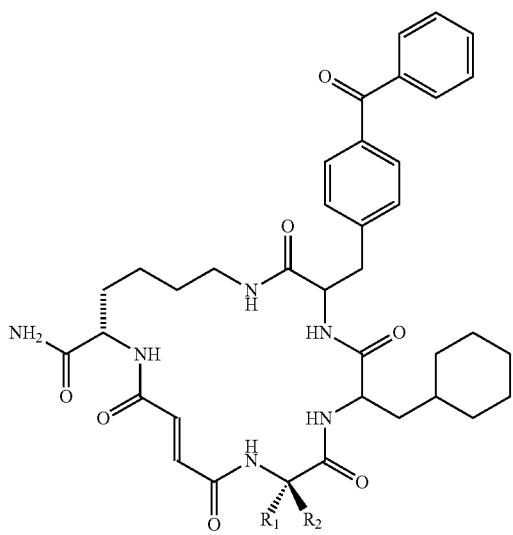

or a pharmaceutically acceptable salt, solvate, hydrate, stereoisomer, polymorph, tautomer, or isotopically enriched form thereof.

6. The compound of claim 1, wherein $R_2$ is hydrogen or $-(CH_2)_q-CH_3$, wherein q is 0 or an integer between 1 and 10, inclusive.

7. The compound of claim 1, wherein $R_5$ is $-C(=O)NH_2$, or $-CH_2-C(=O)NH_2$.

8. The compound of claim 1, wherein ===== represents a double bond.

9. The compound of claim 1, wherein the compound is

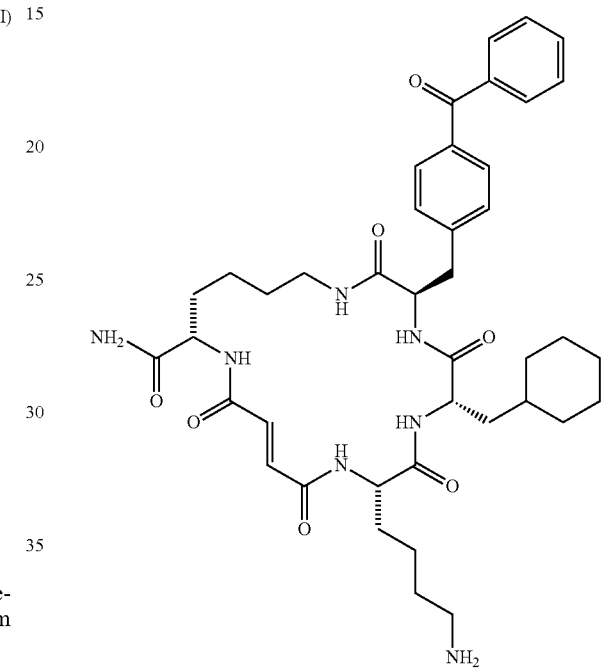

or a pharmaceutically acceptable salt, solvate, hydrate, stereoisomer, polymorph, tautomer, or isotopically enriched form thereof.

10. A pharmaceutical composition comprising a compound of claim 1, or a pharmaceutically acceptable salt, solvate, hydrate, stereoisomer, polymorph, tautomer, or isotopically enriched form thereof, in an amount effective to inhibit IDE in a subject, and optionally a pharmaceutically acceptable carrier.

11. An in vitro method of inhibiting the activity of an insulin degrading enzyme (IDE) comprising contacting an IDE with the compound of claim 1, or a pharmaceutically acceptable salt, solvate, hydrate, stereoisomer, polymorph, tautomer, or isotopically enriched form thereof, in an amount effective to inhibit the activity of IDE.

12. An in vivo method of inhibiting the activity of an insulin degrading enzyme (IDE) comprising contacting an IDE with the compound of claim 1, or a pharmaceutically acceptable salt, solvate, hydrate, stereoisomer, polymorph, tautomer, or isotopically enriched form thereof, in an amount effective to inhibit the activity of IDE.

13. The method of claim 12, wherein the IDE molecule is contacted with the compound, the pharmaceutically acceptable salt, solvate, hydrate, stereoisomer, polymorph, tautomer, or isotopically enriched form thereof, or the composition in a subject.

14. The method of claim 13, wherein the subject exhibits impaired insulin signaling or insulin resistance.

15. The method of claim 14, wherein the subject has diabetes.

16. A method of treating a disease, disorder, or condition associated with impaired insulin signaling or insulin resistance, the method comprising administering a therapeutically effective amount of the compound of claim 1, or a pharmaceutically acceptable salt, solvate, hydrate, stereoisomer, polymorph, tautomer, or isotopically enriched form thereof, to a subject in need thereof.

17. The compound of claim 8, wherein each of $R_E$, $R_F$, $R_G$, and $R_I$ is hydrogen.

18. The compound of claim 17, wherein n is 1 and m is 4.

19. The compound of claim 18, wherein $R_2$ is hydrogen.

20. The compound of claim 19, wherein $R_5$ is —C(=O)—N(R_J)_2.

21. The compound of claim 1, wherein $R_5$ is —C(=O)—N(R_J)_2.

22. The compound of claim 1, wherein the compound is of Formula (VIII):

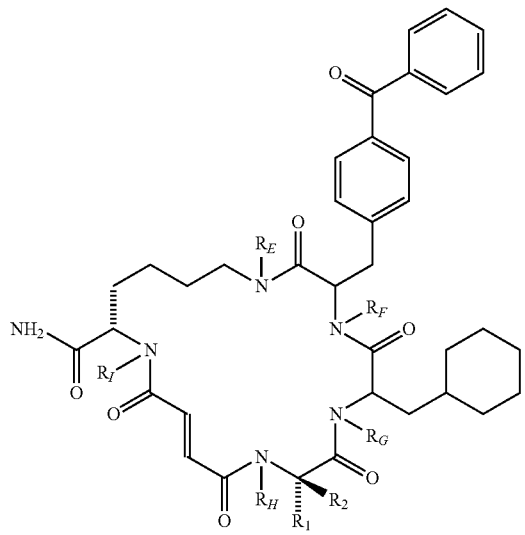

(VIII)

or a pharmaceutically acceptable salt, solvate, hydrate, stereoisomer, polymorph, tautomer, or isotopically enriched form thereof.

23. The method of claim 16, wherein the disease, disorder, or condition is diabetes.

24. The method of claim 16, wherein the disease, disorder, or condition is metabolic syndrome.

* * * * *